US012723268B2

(12) United States Patent
Carson et al.

(10) Patent No.: US 12,723,268 B2
(45) **Date of Patent: *Sep. 1, 2026**

(54) METHODS OF MANUFACTURING CAR-T CELLS

(71) Applicant: CRISPR Therapeutics AG, Zug (CH)

(72) Inventors: Julie Carson, Cambridge, MA (US); Demetrios Kalaitzidis, Cambridge, MA (US); Siyuan Tan, Cambridge, MA (US); Hui Yu, Cambridge, MA (US)

(73) Assignee: CRISPR Therapeutics AG, Zug (CH)

( * ) Notice: Subject to any disclaimer, the term of this patent is extended or adjusted under 35 U.S.C. 154(b) by 284 days.

This patent is subject to a terminal disclaimer.

(21) Appl. No.: 17/098,219

(22) Filed: Nov. 13, 2020

(65) Prior Publication Data

US 2021/0139935 A1 May 13, 2021

Related U.S. Application Data

(60) Provisional application No. 62/934,999, filed on Nov. 13, 2019.

(51) Int. Cl.

| | |
|---|---|
| ***C12N 15/90*** | (2006.01) |
| ***A61K 40/11*** | (2025.01) |
| ***A61K 40/31*** | (2025.01) |
| ***A61K 40/42*** | (2025.01) |
| ***A61K 40/50*** | (2025.01) |
| ***C12N 5/0783*** | (2010.01) |
| ***C12N 9/22*** | (2006.01) |
| ***C12N 15/11*** | (2006.01) |

(52) U.S. Cl.

CPC ............ *C12N 15/907* (2013.01); *A61K 40/11* (2025.01); *A61K 40/31* (2025.01); *A61K 40/4232* (2025.01); *C12N 5/0636* (2013.01); *C12N 9/22* (2013.01); *C12N 15/11* (2013.01); *A61K 40/50* (2025.01); *C12N 2310/20* (2017.05); *C12N 2501/505* (2013.01); *C12N 2750/14144* (2013.01); *C12N 2800/80* (2013.01)

(58) Field of Classification Search

CPC ............................ C12N 5/0636; C12N 15/11; C12N 2501/515; C12N 2510/00; C07K 14/70517; C07K 2317/622

See application file for complete search history.

(56) References Cited

U.S. PATENT DOCUMENTS

| | | | | |
|---|---|---|---|---|
| 7,083,785 | B2 | 8/2006 | Browning et al. | |
| 7,435,596 | B2 | 10/2008 | Campana et al. | |
| 7,446,179 | B2 | 11/2008 | Jensen et al. | |
| 7,446,190 | B2 | 11/2008 | Sadelain et al. | |
| 7,452,981 | B2 | 11/2008 | Wijdenes et al. | |
| 7,491,390 | B2 | 2/2009 | Law et al. | |
| 7,641,903 | B2 | 1/2010 | Law et al. | |
| 7,662,387 | B2 | 2/2010 | Law et al. | |
| 7,700,739 | B2 | 4/2010 | Lacy et al. | |
| 7,741,465 | B1 | 6/2010 | Eshhar et al. | |
| 7,771,720 | B2 | 8/2010 | Staunton et al. | |
| 7,786,282 | B2 * | 8/2010 | Prussak | A61P 35/00 435/325 |
| 7,888,121 | B2 | 2/2011 | Umov et al. | |
| 8,067,546 | B2 | 11/2011 | McDonagh et al. | |
| 8,124,738 | B2 | 2/2012 | Terret et al. | |
| 8,337,838 | B2 | 12/2012 | Law et al. | |
| 8,440,806 | B2 | 5/2013 | Wijdenes et al. | |
| 8,535,678 | B2 | 9/2013 | Law et al. | |
| 8,562,987 | B2 | 10/2013 | McDonagh et al. | |
| 8,609,104 | B2 | 12/2013 | Law et al. | |
| 8,629,257 | B2 | 1/2014 | Lacy et al. | |
| 8,647,624 | B2 | 2/2014 | Law et al. | |
| 8,663,642 | B2 | 3/2014 | Law et al. | |
| 8,673,304 | B2 | 3/2014 | Wijdenes et al. | |
| 8,697,359 | B1 * | 4/2014 | Zhang | C12N 15/85 435/6.13 |
| 8,834,882 | B2 | 9/2014 | Silence et al. | |
| 8,871,908 | B2 | 10/2014 | Liu et al. | |
| 8,956,828 | B2 | 2/2015 | Bonini et al. | |
| 9,023,999 | B2 | 5/2015 | Mori et al. | |
| 9,051,372 | B2 | 6/2015 | Law et al. | |
| 9,102,737 | B2 | 8/2015 | Chen et al. | |
| 9,120,854 | B2 | 9/2015 | Ryan et al. | |
| 9,169,325 | B2 | 10/2015 | Keler et al. | |
| 9,382,319 | B2 | 7/2016 | Tso et al. | |

(Continued)

FOREIGN PATENT DOCUMENTS

| | | | |
|---|---|---|---|
| AU | 2014351557 | A1 | 5/2016 |
| CN | 104910278 | A | 9/2015 |

(Continued)

OTHER PUBLICATIONS

Abdelhakim et al., Role of αβ T cell depletion in Prevention of Graft versus Host Disease, Biomedicines, 2017, vol. 5, Issue 3, pp. 1-14 (Year: 2017).*

Graham et al., Allogenic CAR-T Cells: More than Ease of Access?, 2018, Cells, vol. 7, Issue 10, pp. 1-11 (Year: 2018).*

Rupp et al., CRISPR/Cas9-mediated PD-1 disruption enhances anti-tumor efficacy of human chimeric antigen receptor T cells, 2017, Nature Scientific Reports, vol. 7, Issue 737, pp. 1-10 (Year: 2017).*

Nct00924326, CAR T Cell Receptor Immunotherapy for Patients With B-cell Lymphoma, Sep. 22, 2018, retrieved from clicialtrials.gov (Year: 2018).*

(Continued)

*Primary Examiner* — Jeffrey Stucker
*Assistant Examiner* — Brittney E Donoghue
(74) *Attorney, Agent, or Firm* — Casimir Jones, S.C.; J. Mitchell Jones

(57) ABSTRACT

Aspects of the present disclosure relate to methods for manufacturing genetically engineered T cells expressing a chimeric antigen receptor (CAR) that provide several improvements over conventional manufacturing methods, thereby enabling production of a robust supply of clinically useful CAR T-cell therapies.

43 Claims, 5 Drawing Sheets

Figure 1:
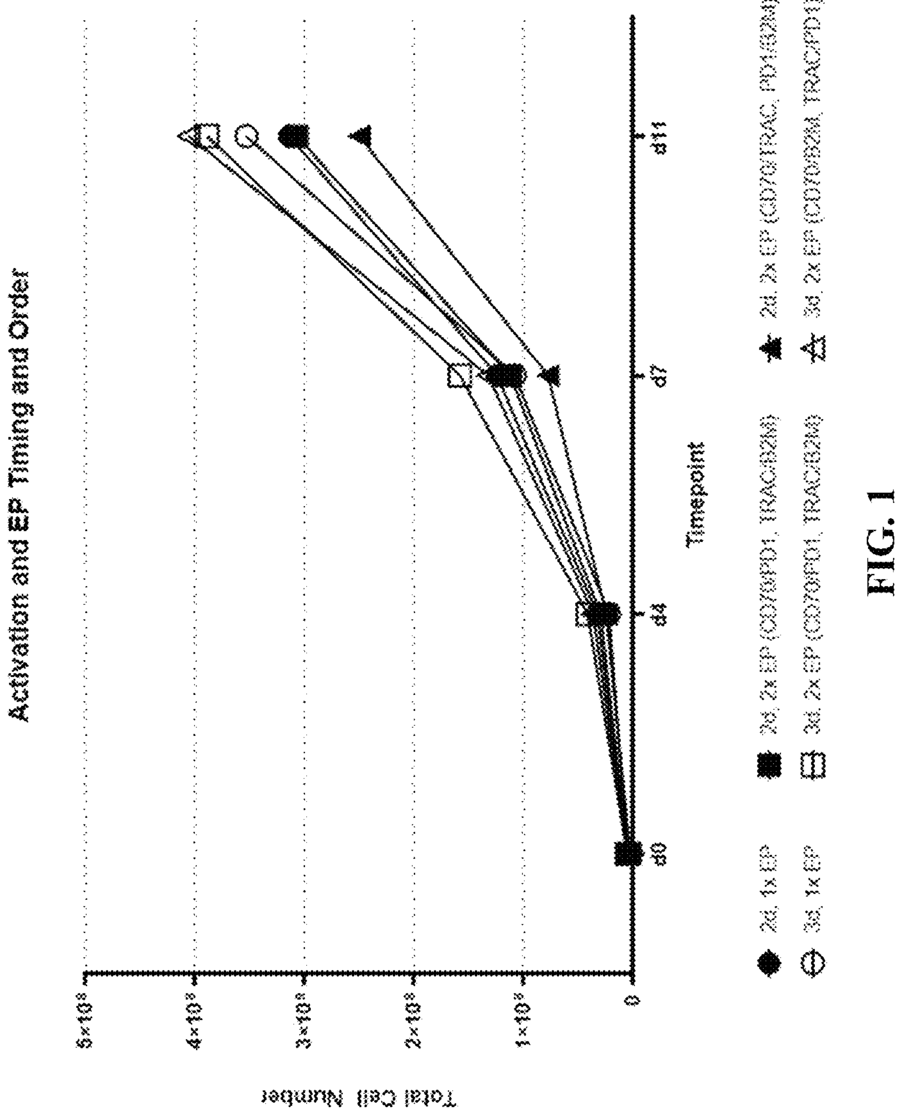

Specification includes a Sequence Listing.

(56) References Cited

U.S. PATENT DOCUMENTS

| | | | |
|---|---|---|---|
| 9,399,074 | B2 | 7/2016 | Liu et al. |
| 9,403,914 | B2 | 8/2016 | Kubota |
| 9,428,585 | B2 | 8/2016 | McDonagh et al. |
| 9,701,752 | B2 | 7/2017 | McDonagh et al. |
| 9,758,581 | B2 | 9/2017 | Wijdenes et al. |
| 9,765,148 | B2 | 9/2017 | Silence et al. |
| 9,765,149 | B2 | 9/2017 | Silence et al. |
| 9,889,160 | B2 | 2/2018 | Jantz et al. |
| 9,937,207 | B2 | 4/2018 | Gregory et al. |
| 10,166,255 | B2 | 1/2019 | Moriarity et al. |
| 10,266,850 | B2 * | 4/2019 | Doudna ................ H01L 21/205 |
| 10,442,849 | B2 | 10/2019 | Baeuerle et al. |
| 10,584,352 | B2 | 3/2020 | Duchateau et al. |
| 10,729,725 | B2 | 8/2020 | Terrett et al. |
| 10,736,919 | B2 | 8/2020 | Terrett et al. |
| 10,857,184 | B2 | 12/2020 | Terrett et al. |
| 10,881,689 | B2 | 1/2021 | Terrett et al. |
| 2006/0051346 | A1 | 3/2006 | Wijdenes |
| 2008/0138343 | A1 | 6/2008 | Law et al. |
| 2009/0081239 | A1 | 3/2009 | Staunton et al. |
| 2009/0148942 | A1 | 6/2009 | McDonagh et al. |
| 2009/0208496 | A1 | 8/2009 | Wijdenes et al. |
| 2010/0129362 | A1 | 5/2010 | Law et al. |
| 2012/0034159 | A1 | 2/2012 | Kindsvogel |
| 2012/0045436 | A1 | 2/2012 | McDonagh et al. |
| 2012/0213771 | A1 | 8/2012 | Keler et al. |
| 2012/0294863 | A1 | 11/2012 | Law et al. |
| 2013/0039911 | A1 | 2/2013 | Bedi et al. |
| 2013/0122020 | A1 | 5/2013 | Liu et al. |
| 2013/0138586 | A1 | 5/2013 | Jung et al. |
| 2013/0287748 | A1 | 10/2013 | June et al. |
| 2014/0105915 | A1 | 4/2014 | Algate et al. |
| 2014/0112942 | A1 | 4/2014 | Van Eenennaam et al. |
| 2014/0178936 | A1 | 6/2014 | McDonagh et al. |
| 2014/0220008 | A1 | 8/2014 | Wijdenes et al. |
| 2014/0242700 | A1 * | 8/2014 | Zhang .................... C12N 15/85 435/325 |
| 2014/0349402 | A1 | 11/2014 | Cooper et al. |
| 2014/0357844 | A1 | 12/2014 | Liu et al. |
| 2015/0176013 | A1 | 6/2015 | Musunuru et al. |
| 2015/0266963 | A1 | 9/2015 | Silence et al. |
| 2015/0284467 | A1 | 10/2015 | Lipp et al. |
| 2015/0337047 | A1 | 11/2015 | Keler et al. |
| 2015/0368351 | A1 | 12/2015 | Vu et al. |
| 2016/0046724 | A1 | 2/2016 | Brogdon et al. |
| 2016/0289675 | A1 | 10/2016 | Ryan et al. |
| 2017/0022282 | A1 | 1/2017 | McDonagh et al. |
| 2017/0107286 | A1 | 4/2017 | Kochenderfer |
| 2017/0157176 | A1 | 6/2017 | Wang et al. |
| 2017/0173080 | A1 | 6/2017 | Lee et al. |
| 2017/0183418 | A1 | 6/2017 | Galetto |
| 2017/0226216 | A1 | 8/2017 | Morgan et al. |
| 2017/0233484 | A1 | 8/2017 | Sussman et al. |
| 2017/0267771 | A1 | 9/2017 | Van Eenennaam et al. |
| 2017/0281766 | A1 | 10/2017 | Wiltzius |
| 2017/0313759 | A1 | 11/2017 | Batuwangala |
| 2017/0320957 | A1 | 11/2017 | Chen et al. |
| 2017/0335281 | A1 | 11/2017 | Loew et al. |
| 2017/0342157 | A1 | 11/2017 | McDonagh et al. |
| 2017/0355776 | A1 | 12/2017 | Xiao et al. |
| 2017/0362297 | A1 | 12/2017 | Marasco |
| 2017/0369581 | A9 | 12/2017 | Silence et al. |
| 2018/0002435 | A1 | 1/2018 | Sasu et al. |
| 2018/0186878 | A1 | 7/2018 | Rosenthal |
| 2018/0201901 | A1 * | 7/2018 | Duchateau ........... C12N 5/0636 |
| 2018/0318435 | A1 | 11/2018 | Pastan et al. |
| 2018/0325955 | A1 * | 11/2018 | Terrett ................... A61K 35/17 |
| 2019/0032049 | A1 * | 1/2019 | Naldini .............. A61K 38/1709 |
| 2019/0048060 | A1 * | 2/2019 | Conway ............... C12N 15/907 |
| 2019/0136230 | A1 * | 5/2019 | Sather .................... C12N 15/11 |
| 2019/0233528 | A1 * | 8/2019 | Srivatsa Srinivasan ..................... A61P 35/04 |
| 2019/0247433 | A1 * | 8/2019 | Kalra ................... C12N 5/0636 |
| 2019/0314413 | A1 | 10/2019 | Terrett et al. |
| 2019/0314414 | A1 | 10/2019 | Terrett et al. |
| 2019/0365808 | A1 | 12/2019 | Terrett et al. |
| 2019/0365809 | A1 | 12/2019 | Terrett et al. |
| 2020/0330518 | A1 | 10/2020 | Terrett et al. |
| 2020/0405761 | A1 | 12/2020 | Terrett et al. |
| 2020/0405764 | A1 | 12/2020 | Terrett et al. |

FOREIGN PATENT DOCUMENTS

| | | | | |
|---|---|---|---|---|
| CN | 106519034 | A | 3/2017 | |
| CN | 106544321 | A | 3/2017 | |
| CN | 107206024 | A | 9/2017 | |
| CN | 108192927 | A * | 6/2018 | ......... A01K 67/0275 |
| JP | 2015-531242 | A | 11/2015 | |
| WO | WO 2004/073656 | A2 | 9/2004 | |
| WO | WO 2006/060878 | A1 | 6/2006 | |
| WO | WO 2006/113909 | A2 | 10/2006 | |
| WO | WO 2008/121420 | A1 | 10/2008 | |
| WO | WO 2011/059836 | A2 | 5/2011 | |
| WO | WO 2011/130434 | A2 | 10/2011 | |
| WO | WO 2012/004367 | A1 | 1/2012 | |
| WO | WO 2012/058460 | A2 | 5/2012 | |
| WO | WO 2012/079000 | A1 | 6/2012 | |
| WO | WO 2013/074916 | A1 | 5/2013 | |
| WO | WO 2013/138586 | A1 | 9/2013 | |
| WO | WO 2013/154760 | A1 | 10/2013 | |
| WO | WO 2013/176915 | A1 | 11/2013 | |
| WO | WO 2014/068079 | A1 | 5/2014 | |
| WO | WO 2014/122143 | A1 | 8/2014 | |
| WO | WO 2014/140374 | A2 | 9/2014 | |
| WO | WO 2014/158821 | A1 | 10/2014 | |
| WO | WO 2014/165119 | A1 | 10/2014 | |
| WO | WO 2014/165825 | A2 | 10/2014 | |
| WO | WO 2014/191128 | A1 | 12/2014 | |
| WO | WO 2015/120096 | A2 | 8/2015 | |
| WO | WO 2015/121454 | A1 | 8/2015 | |
| WO | WO 2015/134877 | A1 | 9/2015 | |
| WO | WO 2015/136001 | A1 | 9/2015 | |
| WO | WO 2015/158671 | A1 | 10/2015 | |
| WO | WO 2015/161276 | A2 | 10/2015 | |
| WO | WO 2015/164594 | A1 | 10/2015 | |
| WO | WO 2015/187528 | A1 | 12/2015 | |
| WO | WO 2015/188056 | A1 | 12/2015 | |
| WO | WO 2016/014789 | A2 | 1/2016 | |
| WO | WO 2016/025454 | A2 | 2/2016 | |
| WO | WO 2016/063264 | A1 | 4/2016 | |
| WO | WO 2016/069282 | A1 | 5/2016 | |
| WO | WO 2016/069283 | A1 | 5/2016 | |
| WO | WO 2016/073955 | A2 | 5/2016 | |
| WO | WO 2016/090320 | A1 | 6/2016 | |
| WO | WO 2016/094304 | A2 | 6/2016 | |
| WO | WO 2016/100985 | A2 | 6/2016 | |
| WO | WO-2016115179 | A1 * | 7/2016 | ............ C12M 35/00 |
| WO | WO 2016/120216 | A1 | 8/2016 | |
| WO | WO 2016/151315 | A1 | 9/2016 | |
| WO | WO 2016/160721 | A1 | 10/2016 | |
| WO | WO 2016/164356 | A1 | 10/2016 | |
| WO | WO 2016/174652 | A1 | 11/2016 | |
| WO | WO 2016/183041 | A2 | 11/2016 | |
| WO | WO 2017/058850 | A1 | 4/2017 | |
| WO | WO 2017/062451 | A1 | 4/2017 | |
| WO | WO 2017/070429 | A1 | 4/2017 | |
| WO | WO 2017/075537 | A1 | 5/2017 | |
| WO | WO 2017/083511 | A1 | 5/2017 | |
| WO | WO 2017/093969 | A1 | 6/2017 | |
| WO | WO 2017/100176 | A1 | 6/2017 | |
| WO | WO 2017/106528 | A1 | 6/2017 | |
| WO | WO 2017/112859 | A2 | 6/2017 | |
| WO | WO 2017/130223 | A1 | 8/2017 | |
| WO | WO 2017/143069 | A1 | 8/2017 | |
| WO | WO 2017/149515 | A1 | 9/2017 | |
| WO | WO 2017/156484 | A1 | 9/2017 | |
| WO | WO 2017/177137 | A1 | 10/2017 | |
| WO | WO 2017/180993 | A1 | 10/2017 | |
| WO | WO 2017/186928 | A1 | 11/2017 | |
| WO | WO 2017/189959 | A1 | 11/2017 | |
| WO | WO 2017/193107 | A2 | 11/2017 | |
| WO | WO 2017/210617 | A2 | 12/2017 | |
| WO | WO 2017/211900 | A1 | 12/2017 | |
| WO | WO 2017/222398 | A1 | 12/2017 | |

(56) References Cited

FOREIGN PATENT DOCUMENTS

| | | | | |
|---|---|---|---|---|
| WO | WO 2017/222593 A1 | | 12/2017 | |
| WO | WO 2018/068257 A1 | | 4/2018 | |
| WO | WO 2018/073391 A2 | | 4/2018 | |
| WO | WO 2018/073393 A2 | | 4/2018 | |
| WO | WO 2018/115887 A1 | | 6/2018 | |
| WO | WO 2018/132479 A1 | | 7/2018 | |
| WO | WO-2018157072 A1 | * | 8/2018 | ........... C12N 5/0031 |
| WO | WO 2019/097305 A2 | | 5/2019 | |
| WO | WO 2019/152742 A1 | | 8/2019 | |
| WO | WO 2019/215500 A1 | | 11/2019 | |

OTHER PUBLICATIONS

Stemcell Technologies, Optimization of Human T Cell Expansion Protocol: Effects of Early Cell Dilution, 2018, Version 1.0.0, Retrieved from: https://www.stemcell.com/optimization-of-human-t-cell-expansion-protocol-effects-ofearly-cell-dilution.html (Year: 2018).*

Wang and Riviere, Clinical manufacturing of CAR T cells: foundation of a promising therapy, 2016, Molecular Therapy Oncolytics, vol. 3, pp. 1-8 (Year: 2016).*

Tey et al., Inducible caspase 9 suicide gene to improve the safety of allodepleted T cells after haploidentical stem cell transplantation, 2007, Biology of Blood and Marrow Transplantation, vol. 13, Issue 8, pp. 1-22 (Year: 2007).*

Life Technologies, Dynabeads Human T-Activator CD3/CD28, 2011, pp. 1-2, retrieved from: https://assets.fishersci.com/TFS-Assets/LSG/manuals/11131D_32D_61D.pdf (Year: 2011).*

Coeshott et al., Large-scale expansion and characterization of CD3+ T-cells in the Quantum Cell Expansion System, 2019, Journal of Translational Medicine, vol. 17, Issue 258, pp. 1-13 (Year: 2019).*

Ling et al., High-Efficiency Transduction of Primary Human Hematopoietic Stem/Progenitor Cells by AAV6 Vectors: Strategies for Overcoming Donor-Variation and Implications in Genome Editing, 2016, Nature Scientific Reports, vol. 6, Article 35495, pp. 1-8 (Year: 2016).*

Mali et al., RNA-Guided Human Genome Engineering via Cas9, 2013, Science, vol. 339, pp. 823-826 (Year: 2013).*

Hendel et al., Chemically modified guide RNAs enhance CRISPR-Cas genome editing in human primary cells, 2015, Nature Biotechnology, vol. 33, No. 9, pp. 985-991 (Year: 2015).*

Ren et al., A versatile system for rapid multiplex genome-edited CAR T cell generation, 2017, Oncotarget, vol. 8, No. 10, pp. 17002-17011 (Year: 2017).*

Varshney et al., High-throughput gene targeting and phenotyping in zebrafish using CRIPSR/Cas9, 2015, Genome Research, vol. 25, pp. 1030-1042 (Year: 2015).*

Kumar et al., The CRISPR-Cas system for plant genome editing: advances and opportunities, 2015, Journal of Experimental Botany, vol. 66, No. 1, pp. 47-57 (Year: 2015).*

Ren et al., Multiplex Genome Editing to Generate Universal CAR T Cells Resistant to PD1 Inhibition, 2017, Clinical Cancer Research, vol. 23, Issue 9, pp. 2255-2266 (Year: 2017).*

Behr et al., In vivo delivery of CRISPR-Cas9 therapeutics: Progress and challenges, 2021, Chinese Pharmaceutical Association, vol. 11, Issue 8, pp. 2150-2171 (Year: 2021).*

Innovative Genomics Institute (IGI), Ribonucleoprotein complex (RNP), 2017, ages 1-4, retrieved from: https://innovativegenomics.org/glossary/ribonucleoprotein-complex-rnp/ (Year: 2017).*

Vocabulary, introduce, 2016, pp. 1-5, retrieved from: https://www.vocabulary.com/dictionary/introduce (Year: 2016).*

Thompson et al., The future of multiplexed eukaryotic genome engineering, 2018, ACS Chem Biol., vol. 13, Issue 2, pp. 313-325 (Year: 2018).*

Dai et al., One-step generation of modular CAR-T cells with AAV-Cpf1, 2019, Nature Methods, vol. 16, pp. 247-254 (Year: 2019).*

Eyquem et al., Targeting a CAR to the TRAC locus with CRISPR/Cas9 enhances tumour rejection. Nature. Mar. 2, 2017;543(7643):113-117. Epub Feb. 22, 2017.

Fraiietta et al., Determinants of response and resistance to CD19 chimeric antigen receptor (CAR) T cell therapy of chronic lymphocytic leukemia. Nature Medicine. 2018;24(5):563-71.

Jaspers et al., Development of CAR T cells designed to improve antitumor efficacy and safety. Pharmacol Ther. Oct. 2017;178:83-91. Epub Mar. 22, 2017.

Liu et al., CRISPR-Cas9-mediated multiplex gene editing in CAR-T cells. Cell Res. Jan. 2017;27(1):154-157. Epub Dec. 2, 2016.

Macleod et al., Integration of a CD19 CAR into the TCR alpha chain locus streamlines production of alleogenic gene-edited CAR T cells. Molecular Therapy. 2017;25(4):949-61.

Maude et al., Chimeric antigen receptor T cells for sustained remissions in leukemia. The New England Journal of Medicine. 2014;371:1507-17.

Osborn et al., Evaluation of TCR gene editing achieved by TALENs, CRISPR/Cas9, and megaTAL nucleases. Molecular Therapy. 2016;24(3):570-81.

Poirot et al., Multiplex genome-edited T-cell manufacturing platform for "off-the-shelf" adoptive T-cell immunotherapies. Cancer Research. 2015;75(18):3853-64.

Ren et al., A versatile system for rapid multiplex genome-edited CAR T cell generation. Oncotarget. 2017;8 (10):17002-11.

Ren et al., Advancing chimeric antigen receptor T cell therapy with CRISPR/Cas9. Protein Cell. Sep. 2017;8(9):634-643. Epub Apr. 22, 2017.

Ren et al., Multiplex Genome Editing to Generate Universal CAR T Cells Resistant to PD1 Inhibition. Clin Cancer Res. May 1, 2017;23(9):2255-2266. Epub Nov. 4, 2016.

Torikai et al., A foundation for universal T-cell based immunotherapy: T cells engineered to express a CD19-specific chimeric-antigen-receptor and eliminate expression of endogenous TCR. Blood. Jun. 14, 2012;119(24):5697-705. Epub Apr. 24, 2012. Erratum in: Blood. Nov. 26, 2015;126(22):2527. Rabinovitch, Brian [corrected to Rabinovich, Brian].

Zah et al., T Cells Expressing CD19/CD20 Bispecific Chimeric Antigen Receptors Prevent Antigen Escape by Malignant B Cells. Cancer Immunol Res. Jun. 2016;4(6):498-508. doi: 10.1158/2326-6066.CIR-15-0231. Epub Apr. 8, 2016.

[No Author Listed], Medarex. Preclinical Data Demonstrating Potent Anti-Tumor Activity of Anti-CD19 and Anti-CD70 Antibody-Drug Conjugates in Cancer Animal Models. Accessible at pipelinereview.com/index.php/2007041811096/Antibodies/Medarex-Presents-Preclinical-Data-Demonstrating-Potent-Anti-Tumor-Activity-of-Anti-CD19-and-Anti-CD70-Antibody-Drug-Conjugates-in-Cancer-Animal-Models.html. Apr. 18, 2007. 2 pages.

Lee et al., 323. Efficient Generation of CART Cells by Homology Directed Transgene Integration into the TCR-Alpha Locus. Mol Ther. May 2016;24(Supplement 1):S130. 1 page.

Macleod et al., Generation of a Novel Allogeneic CAR T Cell Platform Utilizing an Engineered Meganuclease and AAV Donor Template to Achieve Efficient Disruption of T Cell Receptor Expression and Simultaneous Homology-Directed Insertion of a CD19 CAR. Mol Ther. May 2016;24(Supplement 1): S156. 1 page.

Whisenant et al., The Activation-Induced Assembly of an RNA/Protein Interactome Centered on the Splicing Factor U2AF2 Regulates Gene Expression in Human CD4 T Cells. PLoS One. Dec. 7, 2015;10(12):e0144409.

International Search Report and Written Opinion for International Application No. PCT/IB2020/060722, mailed Jan. 18, 2021, 10 Pages.

* cited by examiner

METHODS OF MANUFACTURING CAR-T CELLS

CROSS-REFERENCE TO RELATED APPLICATIONS

This application claims the benefit of priority to U.S. Provisional Patent Application No. 62/934,999, filed Nov. 13, 2019, which is hereby incorporated by reference in its entirety.

SEQUENCE LISTING

The application contains a Sequence Listing that has been filed electronically in the form of a text file, created Nov. 13, 2020, and named "095136-0147-003US1_SEQ.TXT" (61,206 bytes), the contents of which are incorporated by reference herein in their entirety.

BACKGROUND

Chimeric antigen receptor (CAR) T-cell therapy has shown promising therapeutic effects in treating hematologic cancer. Typically, CAR-T cells are generated by genetic engineering of either patient immune cells (autologous) or immune cells from unrelated human donors (allogenic). Production of high-quality, clinical grade CAR-T cells is a prerequisite for the wide application of this technology. It is therefore of great interest to develop efficient manufacturing processes for large-scale production of CAR-T cells.

SUMMARY OF THE INVENTION

The present disclosure is based, at least in part, on the development of methods for manufacturing genetically engineered T cells expressing a chimeric antigen receptor (CAR) that provide several improvements over conventional manufacturing methods. Such improvements include, but are not limited to, improvements in consistency and efficiency of genetic modifications (e.g., improvements in consistency and efficiency of triple genome editing) described herein, which allows production of a robust supply of clinically useful CAR T-cell therapies.

Accordingly, one aspect of the present disclosure provides a method for manufacturing genetically engineered T cells, the method comprising (i) providing a first population of T cells; (ii) introducing into the first population of T cells a first ribonucleoprotein (RNP) complex comprising a first Cas9 enzyme and a first guide RNA (gRNA) targeting a CD70 gene to produce a second population of T cells, wherein the second population of T cells comprises T cells having the CD70 gene disrupted; (iii) introducing into the second population of T cells a second RNP complex comprising a second Cas9 enzyme and a second gRNA targeting a T cell receptor alpha chain constant region (TRAC) gene, and a third RNP complex comprising a third Cas9 enzyme and a third gRNA targeting a beta-2 microglobulin (β2M) gene to produce a third population of T cells, wherein the third population of T cells comprises activated T cells having the CD70 gene disrupted, the TRAC gene disrupted, and the β2M gene disrupted; (iv) incubating the third population of T cells with an adeno-associated viral (AAV) vector to produce a fourth population of T cells, wherein the AAV vector comprises a nucleic acid sequence encoding a chimeric antigen receptor (CAR) and wherein the nucleic acid sequence is flanked by homologous sequences to the TRAC gene, and wherein the fourth population of T cells comprises activated T cells expressing the CAR and having the CD70 gene disrupted, the TRAC gene disrupted, and the β2M gene disrupted; (v) expanding the fourth population of T cells thereby producing an expanded T cell population; (vi) removing $TCR\alpha\beta^+$ T cells from the expanded T cell population to produce a population of genetically engineered T cells, wherein the population of genetically engineered T cells comprises activated T cells expressing the CAR and having the CD70 gene disrupted, the TRAC gene disrupted, and the β2M gene disrupted; and (vii) harvesting the population of genetically engineered T cells.

In some embodiments, the first population of T cells is derived from cryopreserved T cells enriched from human blood cells. In some embodiments, the first population of T cells is prepared by a process comprising: (a) obtaining blood cells from a human donor; and (b) enriching $CD4^+$ T cells and/or $CD8^+$ T cells from the blood cells. In some embodiments, step (b) is performed using magnetic beads conjugated with anti-CD4 and/or anti-CD8 antibodies. In some embodiments, the first population of T cells has a cell viability of at least about 80% and/or a purity of at least about 80% of CD4+ and $CD8^+$ T cells. In some embodiments, methods further comprises (c) cryopreserving the enriched $CD4^+$ T cells and $CD8^+$ T cells produced in step (b).

In some embodiments, step (ii) is performed by electroporation. In some embodiments, the concentration of the first Cas9 enzyme is about 0.15 mg/mL and the concentration of the first gRNA targeting the CD70 gene is about 0.16 mg/mL. In some embodiments, the cell concentration in step (ii) is about $100\times10^6$ cells/mL to about $400\times10^6$ cells/mL. In some embodiments, the cell concentration in step (ii) is about $100\times10^6$ cells/mL to about $350\times10^6$ cells/mL. In some embodiments, the cell concentration in step (ii) is about $300\times10^6$ cells/mL.

In some embodiments, the methods further comprise after step (ii) and before step (iii), a step of incubating the second population of T cells in the presence of a T cell activating agent in a cell culture vessel to produce an activated population of T cells, wherein the activated population of T cells comprises activated T cells having the CD70 gene disrupted. The T cell activating agent can comprise a CD3 agonist and a CD28 agonist, and wherein the CD3 agonist and CD28 agonist are attached to a nanomatrix particle. The incubating of the second population of T cells in the presence of a T cell activating agent in a cell culture vessel can be done at a cell seeding density of about $2\times10^6/cm^2$ and a cell concentration of about $2\times10^6$ cells/mL for about 72 hours. In some embodiments, the ratio of the T cell activating agent to medium in the mixture is about 1:12.5 (v/v). In still other embodiments, the methods disclosed herein may further comprise diluting the T cell activating agent in the activated population of T cells after incubating the second population of T cells in the presence of a T cell activating agent to reduce activation and to allow cells to recover before step (iii).

In some embodiments, step (iii) is performed by electroporation. In some embodiments, step (iii) involves one electroporation event. In some embodiments, the second RNP complex and the third RNP complex are introduced into the activated T cells in the one electroporation event. In some embodiments, the amount of the second Cas9 enzyme in the second RNP complex is the same as the amount of the third Cas9 enzyme in the third RNA complex. In some embodiments, the concentration of the second Cas9 enzyme is about 0.3 mg/mL, the concentration of the third Cas9 enzyme is about 0.3 mg/mL, the concentration of the second gRNA targeting the TRAC gene is about 0.08 mg/mL, and the concentration of the third gRNA targeting the β2M gene is about 0.2 mg/mL. In some embodiments, the cell concentration in step (iii) is about $100\times10^6$ cells/mL to about $400\times10^6$ cells/mL. In some embodiments, the cell concentration in step (iii) is about $300\times10^6$ cells/mL. In other embodiments, the total cell number in each vessel used in step (iii) (e.g., electroporation) can be about $5\times10^8$ to about $2.5\times10^9$ cells, for example, about $7\times10^8$ cells. In some examples, multiple vessels may be used in step (iii) (e.g., electroporation), for example, about 5-10 vessels. In specific examples, as many as 7 vessels may be used in step (iii), which may contain about $1.5\times10^9$ to about $3\times10^9$ cells (e.g., about $2.1\times10^9$ cells or about $2.7\times10^9$ cells), e.g., for electroporation.

In some embodiments, the AAV vector has a multiplicity of infection (MOI) value of about 10,000 to about 80,000. In some embodiments, the MOI of the AAV vector is about 20,000. In some embodiments, the AAV vector is AAV serotype 6 (AAV6) vector.

In some embodiments, step (v) is performed by culturing the fourth population of T cells in a cell culture vessel at a seeding density of about $2\times10^5$ cells/cm$^2$ to about $5\times10^5$ cells/cm$^2$ for about 7 days to about 12 days. In some embodiments, the fourth population of T cells may be seeded in a cell culture vessel at a seeding density of about 150,000 cells/cm$^2$ to about 600,000 cells/cm$^2$. In some embodiments, the fourth population of T cells is cultured at a seeding density of about $3\times10^5$ cells/cm$^2$ to about $5\times10^5$ cells/cm$^2$. In some embodiments, the cell culture vessel is a static cell culture vessel (also referred interchangeably herein as a static culture vessel) allowing for cell expansion for about 10 days to about 12 days without medium change.

In some embodiments, step (vi) is performed by contacting the expanded cells to beads on which anti-TCRαβ antibodies are immobilized, and collecting unbound cells.

In some embodiments, the first Cas9 enzyme, the second Cas9 enzyme, and/or the third Cas9 enzyme is a Cas9 enzyme from Cas9 from *Streptococcus pyogenes* (spCas9). In some embodiments, the first Cas9 enzyme, the second Cas9 enzyme, and the third Cas9 enzyme are the same. In some embodiments, the first Cas9 enzyme, the second Cas9 enzyme, and the third Cas9 enzyme comprise the amino acid sequence of SEQ ID NO: 1.

In some embodiments, the first gRNA targeting the CD70 gene comprises a spacer sequence of SEQ ID NO: 4. In some embodiments, the first gRNA targeting the CD70 gene comprises the nucleotide sequence of SEQ ID NO: 2.

In some embodiments, the second gRNA targeting the TRAC gene comprises a spacer sequence of SEQ ID NO: 8. In some embodiments, the second gRNA targeting the TRAC gene comprises the nucleotide sequence of SEQ ID NO: 6.

In some embodiments, the third gRNA targeting the β2M gene comprises a spacer sequence of SEQ ID NO: 12. In some embodiments, the third gRNA targeting the β2M gene comprises the nucleotide sequence of SEQ ID NO: 10.

In some embodiments, the first gRNA, the second gRNA, the third gRNA, and/or a combination thereof, comprise one or more 2'-O-methyl phosphorothioate modification.

In some embodiments, the CAR comprises an extracellular domain targeting a cancer antigen, a transmembrane domain, a co-stimulatory domain, and a CD3 cytoplasmic signaling domain. In some embodiments, the extracellular domain comprises a single-chain variable fragment (scFv), the transmembrane domain is derived from CD8a, and/or the co-stimulatory domain is derived from 4-1 BB. In some embodiments, the scFv fragment binds CD70. In some embodiments, the CAR comprises the amino acid sequence of SEQ ID NO: 46.

Accordingly, one aspect of the present disclosure provides a method for manufacturing genetically engineered T cells, the method comprising (i) providing a first population of T cells; (ii) introducing into the first population of T cells a first ribonucleoprotein (RNP) complex comprising a first Cas9 enzyme and a first guide RNA (gRNA) targeting a CD70 gene to produce a second population of T cells, wherein the second population of T cells comprises T cells having the CD70 gene disrupted; (iii) incubating the second population of T cells in the presence of a T cell activating agent in a cell culture vessel to produce a third population of T cells, wherein the third population of T cells comprises activated T cells having the CD70 gene disrupted; (iv) introducing into the third population of T cells a second RNP complex comprising a second Cas9 enzyme and a second gRNA targeting a T cell receptor alpha chain constant region (TRAC) gene, and a third RNP complex comprising a third Cas9 enzyme and a third gRNA targeting a beta-2 microglobulin (β2M) gene to produce a fourth population of T cells, wherein the fourth population of T cells comprises activated T cells having the CD70 gene disrupted, the TRAC gene disrupted, and the β2M gene disrupted; (v) incubating the fourth population of T cells with an adeno-associated viral (AAV) vector to produce a fifth population of T cells, wherein the AAV vector comprises a nucleic acid sequence encoding a chimeric antigen receptor (CAR) and wherein the nucleic acid sequence is flanked by homologous sequences to the TRAC gene, and wherein the fifth population of T cells comprises activated T cells expressing the CAR and having the CD70 gene disrupted, the TRAC gene disrupted, and the β2M gene disrupted; (vi) expanding the fifth population of T cells thereby producing an expanded T cell population; (vii) removing TCRαβ$^+$ T cells from the expanded T cell population to produce a population of genetically engineered T cells, wherein the population of genetically engineered T cells comprises activated T cells expressing the CAR and having the CD70 gene disrupted, the TRAC gene disrupted, and the β2M gene disrupted; and (viii) harvesting the population of genetically engineered T cells.

In some embodiments, a genetically engineered T cell population, which is produced by a method described herein.

The details of one or more embodiments of the invention are set forth in the description below. Other features or advantages of the present invention will be apparent from the following drawings and detailed description of several embodiments, and also from the appended claims.

DETAILED DESCRIPTION OF THE DRAWINGS

FIG. 1 is a graph showing T cell expansion post editing of T cells prepared in a small scale manufacturing process. RNP complexes are indicated in parentheses. 2 d: T cells activated for 2 days (48 hours); 3 d: T cells activated for 3 days (72 hours); 1×EP: single electroporation; 2×EP: two-step electroporation.

Figure 2A:
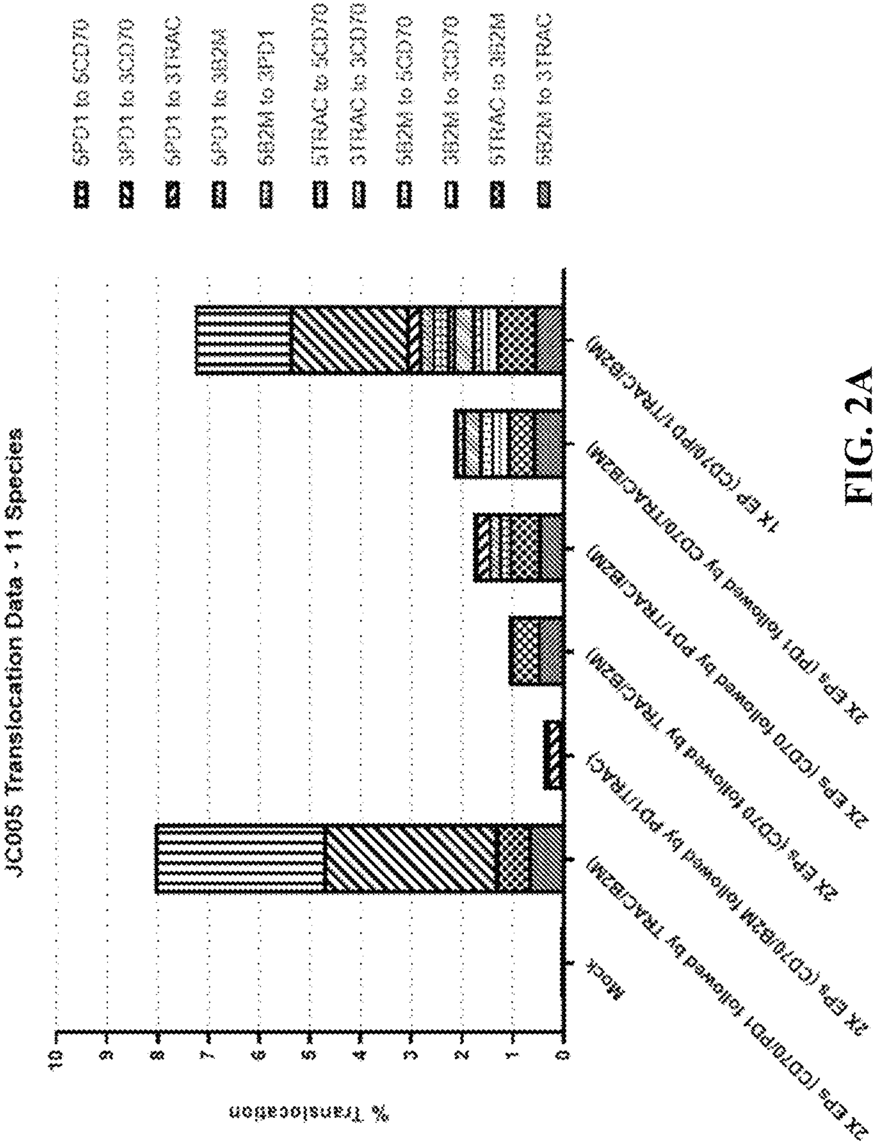
Figure 2B:
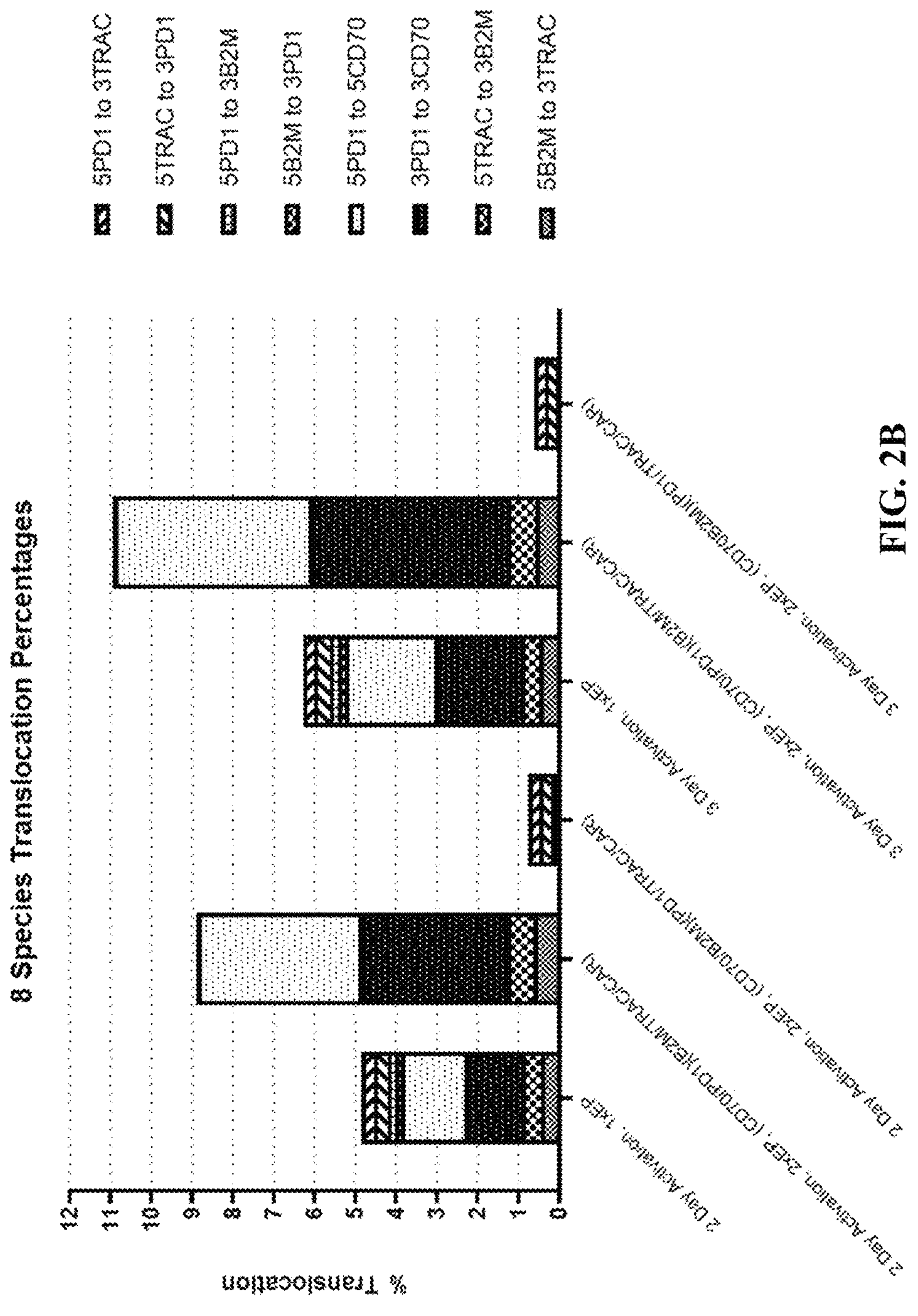

FIGS. 2A-2B include graphs showing effects of a single electroporation or a two-step electroporation on translocation rates. FIG. 2A: a graph showing percent translocations of 11 indicated translocations. FIG. 2B: a graph showing percent translocations of 8 indicated translocations.

Figure 3A:
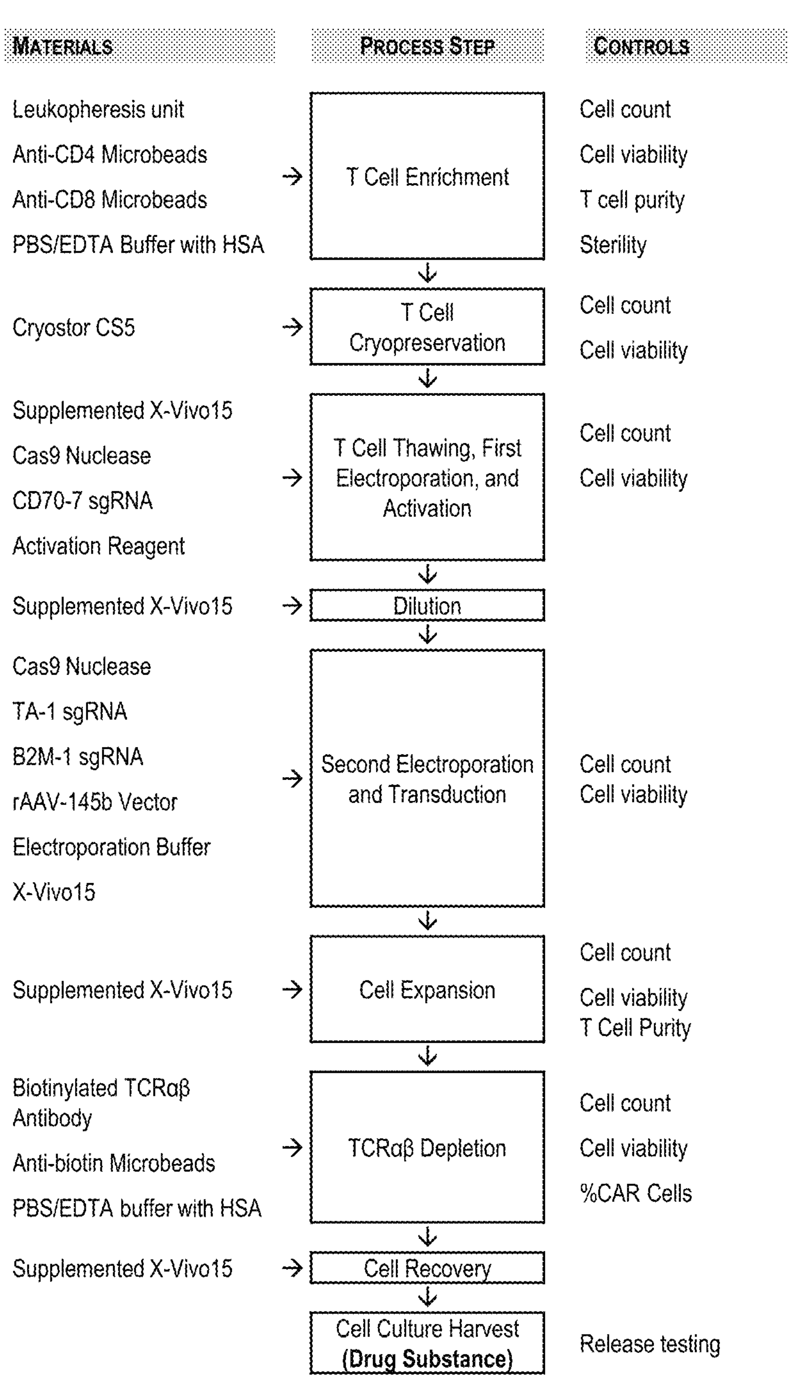
Figure 3B:
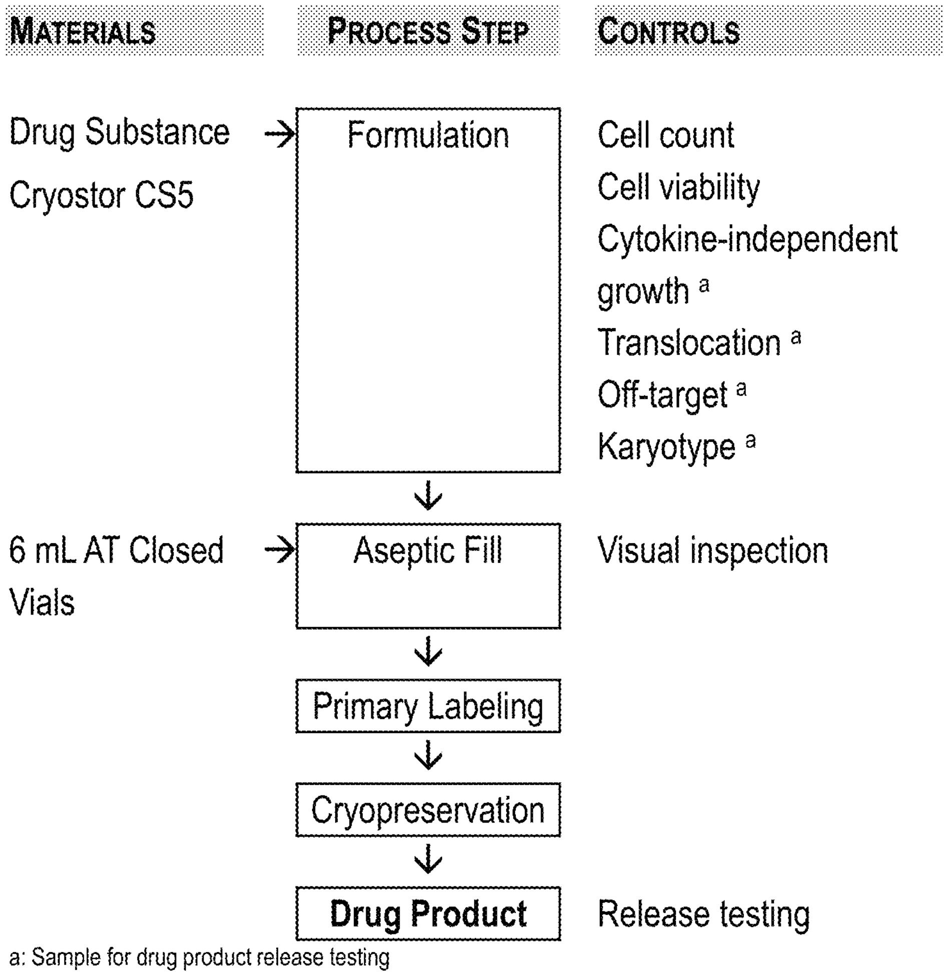

FIGS. 3A-3B include flow charts of methods for making CTX130 T cells, which express an anti-CD70 CAR and have genetically disrupted CD70, 132M, and TRAC genes. FIG.

3A includes a flow chart of an illustrative manufacturing process for making T cells expressing an anti-CD70 CAR, in accordance with some embodiments of the technology described herein. CAR: Chimeric antigen receptor; EDTA: Ethylenediaminetetraacetic acid; HSA: Human serum albumin; IL: Interleukin; PBS: Phosphate buffered saline; rAAV: Recombinant adeno-associated virus; sgRNA: Single guide ribonucleic acid; TCRαβ: T cell receptor alpha chain and T cell receptor beta chain; Supplemented X-VIVO™ 15: X-VIVO™ 15 with 5% male human serum AB, 100 IU/mL rhIL-2 and 100 IU/mL rhIL-7. FIG. 3B includes a flow chart of an illustrative manufacturing process for making a drug product comprising T cells expressing an anti-CD70 CAR, in accordance with some embodiments of the technology described herein.

DETAILED DESCRIPTION OF THE INVENTION

The present disclosure is based, at least in part, on the development of improved manufacturing processes for producing CAR-T cells, particularly allogenic CAR-T cells, including improved conditions for one or more steps of the manufacturing processes. The improved manufacturing processes disclosed herein led to at least the following advantageous outcomes:

(a) Increased % $CAR^+$ expression and attenuated cell loss after electroporation resulting from the improved T cell activation conditions provided herein.

(b) Improved consistency and improved efficiency of β2M gene disruption in T cells resulting from the improved CRISPR-Cas9-mediated gene editing of activated T cells conditions provided herein.

(c) Lower translocation rates resulting from the improved T cell electroporation conditions provided herein.

(d) Increased supply of CAR T-cell therapy resulting from decreased production times and decreased production costs provided by the improved manufacturing processes described herein.

(e) Reduced variability of manufactured drug product resulting from production of uniform and high quality CAR T-therapies using the improved manufacturing processes described herein.

(f) Simplified AAV transduction conditions while maintaining high CAR expression levels in T cells.

Accordingly, provided herein are methods for manufacturing genetically engineered T cells expressing a CAR construct, such as a CAR construct targeting a cancer antigen, for example, CD70, and having CD70, TRAC and β2M genes knocked-out. The genetically engineered T cell populations produced by methods described herein, and therapeutic uses thereof are also within the scope of the present disclosure.

I. Manufacturing Genetically Engineered T Cells

Aspects of the present disclosure provide methods for manufacturing genetically engineered T cells comprising a disrupted cluster of differentiation 70 (CD70) gene, a disrupted beta-2-microglobulin (β2M) gene, and a disrupted T cell receptor alpha chain constant region (TRAC) gene, and an inserted nucleic acid encoding a chimeric antigen receptor (CAR).

Disruption of the CD70 gene prevents cell-to-cell fratricide during manufacturing of genetically engineered T cells. Alternatively, or in addition, disruption of the CD70 gene enables increased health and function (e.g., extended proliferation, reduced exhaustion) of the genetically engineered T cells. Disruption of the β2M gene and the TRAC gene renders the genetically engineered T cell non-alloreactive and suitable for allogeneic transplantation. Insertion of a nucleic acid encoding a CAR enables the genetically engineered T cell to express the CAR on its surface where it targets the genetically engineered T cell to cancer cells.

Accordingly, methods for manufacturing genetically engineered T cells disclosed herein, in some embodiments, involve the use of CRISPR-Cas9 gene editing to disrupt expression of CD70, TRAC, and β2M genes, and the use of adeno-associated virus (AAV) transduction to insert a nucleic acid encoding a CAR.

In general, the method for manufacturing CAR-T cells disclosed herein may comprise: (i) enriching $CD4\pm/CD8^+$ T cells from a suitable human immune cell source, (ii) activating the enriched $CD4\pm/CD8^+$ T cells; (iii) genetically engineering the activated T cells to produce CAR-T cells having disrupted CD70, TRAC, and β2M genes; and harvesting the genetically engineered T cells for therapeutic uses. When needed, the enriched $CD4\pm/CD8^+$ T cells may be stored via cryopreservation for future use. Alternatively, or in addition, the genetically engineered T cells may be expanded in vitro prior to harvesting. $TCR\alpha\beta^+$ T cells may be depleted from the CAR-T cell population thus produced.

(i) T Cell Enrichment

Any of the manufacturing methods disclosed herein may use human blood cells as the starting material. For example, T cells can be obtained from a unit of blood collected from a subject using techniques known to a skilled person, such as sedimentation, e.g., FICOLL™ separation. Alternatively, the T cells for use in making the genetically engineered T cells may be derived from stem cells (e.g., HSCs or iPSCs) via in vitro differentiation. In some embodiments, blood cells can be obtained from an individual human donor. In other embodiments, blood cells can be obtained from multiple human donors (e.g., 2, 3, 4, or 5 human donors).

In some examples, leukopak samples from suitable a human donor may be used. As known in the art, a leukopak sample is an enriched leukapheresis product collected from peripheral blood. It typically contains a variety of blood cells including monocytes, lymphocytes, platelets, plasma, and red cells. The human donor preferably is a healthy human donor. For example, a human donor candidate may be subject to screening for HBV, HCV, HIV, HTLV, WNV, *Trypanosoma cruzi*, and/or CMV. A human subject showing negative results in the screening may be used as a donor for blood cells.

The sources of T-cells that find use in the present methods is not particularly limited. In some embodiments, T cells from a T cell bank can be used as the starting material in any of the manufacturing methods disclosed herein. A T cell bank may comprise T cells with genetic editing of certain genes (e.g., genes involved in cell self renewal, apoptosis, and/or T cell exhaustion or replicative senescence) to improve T cell persistence in cell culture. A T cell bank may be produced from bonafide T cells, for example, non-transformed T cells, terminally differentiated T cells, T cells having stable genome, and/or T cells that depend on cytokines and growth factors for proliferation and expansion. Alternatively, such a T cell bank may be produced from precursor cells such as hematopoietic stem cells (e.g., iPSCs), e.g., in vitro culture. In some examples, the T cells in the T cell bank may comprise genetic editing of one or more genes involved in cell self-renewal, one or more genes involved in apoptosis, and/or one or more genes involved in T cell exhaustion, so as to disrupt or reduce expression of such genes, leading to improved persistence in culture. Examples of the edited genes in a T cell bank include, but are not limited to, Tet2, Fas, CD70, Regnase-1, or a combination thereof. Compared with the non-edited T counterpart, T cells in a T cell bank may have enhanced expansion capacity in culture, enhanced proliferation capacity, greater T cell activation, and/or reduced apoptosis levels.

Suitable T cells can be enriched from human blood cells using conventional methods or methods disclosed herein. T cells for use in making the genetically engineered T cells may express one or more of the T cell markers, including, but not limited to a CD4+, CD8+, or a combination thereof. In some embodiments, $CD4^+$ T cells can be enriched from human blood cells. In other embodiments, $CD8^+$ T cells can be enriched. In specific examples, both CD4+ and $CD8^+$ T cells are purified from human blood cells.

$CD4^+$ T cells and/or $CD8^+$ T cells can be isolated from a suitable blood cell source, such as those described herein, using any method known in the art or those disclosed herein, for example, using antibodies capable of binding to specific cell-surface biomarkers for the target T cells, e.g., antibodies specific to CD4 and/or antibodies specific to CD8. In some embodiments, enriching $CD4^+$ T cells and $CD8^+$ T cells can be performed using anti-CD4 and anti-CD8 antibodies conjugated to magnetic beads. A cell population comprising CD4+ and $CD8^+$ T cells can be incubated with such magnetic beads under suitable conditions for a suitable period allowing for binding of the target T cells to the magnetic beads via the antibodies conjugated to the beads. Non-bound cells can be washed and CD4+ and $CD8^+$ T cells bound to the beads can be collected using routine methods.

The enriched T cells (e.g., $CD4^+$ T cells and $CD8^+$ T cells) may be evaluated for features such as cell viability and/or purity of the target T cells following routine practice. In some embodiments, the T cell population from the enrichment step disclosed here may have a cell viability of at least about 80% (e.g., at least about 85%, at least about 90%, at least about 95%, or above). Alternatively or in addition to, the enriched T cell population may have a purity of at least about 80% of the target T cells (e.g., CD4+ and/or $CD8^+$ T cells), for example, at least about 85%, at least about 90%, at least about 95%, at least about 97%, about 98% or higher. Alternatively or in addition to, the enriched T cell population may have a purity of at least about 70% of the target T cells (e.g., CD4+ and/or $CD8^+$ T cells), for example, at least about 75%, at least about 80%, at least about 85%, at least about 90%, at least about 95%, at least about 97%, about 98% or higher.

The term “about” or “approximately” means within an acceptable error range for the particular value as determined by one of ordinary skill in the art, which will depend in part on how the value is measured or determined, i.e., the limitations of the measurement system. For example, “about” can mean within an acceptable standard deviation, per the practice in the art. Alternatively, “about” can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term “about” is implicit and in this context means within an acceptable error range for the particular value.

The enriched T cell population (which is also within the scope of the present disclosure) may be used immediately for further processing as disclosed herein. Alternatively, the enriched T cell population may be stored under suitable conditions for future use, for example, via cryopreservation. Prior to further processing, cryopreserved T cells can be thawed following routine procedures. Cell viability of the thawed cells can be assessed to determine whether the thawed cells are suitable for further processing.

(ii) CRISPR-CAS9-Mediated Gene Editing of Enriched T Cells

The enriched T cells prepared by any of the procedures disclosed herein may be subjected to gene editing to knock out CD70, via, for example, CRISPR-Cas9 gene editing technology. Knockout of the CD70 gene in a first electroporation step followed by knockout of the TRAC and the β2M genes in a second electroporation step significantly increased editing efficiency and reduced the number of translocations produced during gene editing. See Examples below.

The CD70 gene encodes a member of the tumor necrosis factor superfamily and its expression is restricted to activated T lymphocytes and B lymphocytes and mature dendritic cells. CD70 is implicated in tumor cell and regulatory T cell survival through interaction with its ligand, CD27. Disruption of the CD70 gene minimizes the risk cell-to-cell fratricide during manufacturing of genetically engineered T cells, and enables increased health and function of the manufactured genetically engineered T cells.

CRISPR-Cas9-Mediated Gene Editing System

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an acronym for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see, e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

(a) Cas9

In some embodiments, the Cas9 (CRISPR associated protein 9) endonuclease is used in a CRISPR method for making the genetically engineered T cells as disclosed herein. The Cas9 enzyme may be one from *Streptococcus pyogenes*, although other Cas9 homologs may also be used. It should be understood, that wild-type Cas9 may be used or modified versions of Cas9 may be used (e.g., evolved versions of Cas9, or Cas9 orthologues or variants), as provided herein. In some embodiments, Cas9 comprises a *Streptococcus pyogenes*-derived Cas9 nuclease protein that has been engineered to include C- and N-terminal SV40 large T antigen nuclear localization sequences (NLS). The resulting Cas9 nuclease (sNLS-spCas9-sNLS) is a 162 kDa protein that is produced by recombinant *E. coli* fermentation and purified by chromatography. The spCas9 amino acid sequence can be found as UniProt Accession No. Q99ZW2, which is provided herein as SEQ ID NO: 1.

(b) Guide RNAs (gRNAs)

CRISPR-Cas9-mediated gene editing as described herein includes the use of a guide RNA or a gRNA. As used herein, a "gRNA" refers to a genome-targeting nucleic acid that can direct the Cas9 to a specific target sequence within a CD70 gene or a TRAC gene or a β2M gene for gene editing at the specific target sequence. A guide RNA comprises at least a spacer sequence that hybridizes to a target nucleic acid sequence within a target gene for editing, and a CRISPR repeat sequence.

An exemplary gRNA targeting a CD70 gene is provided in SEQ ID NO: 2. See also International Application No. PCT/IB2019/000500, filed May 10, 2019, now published as WO2019/215500, the relevant disclosures of which are incorporated by reference herein for the subject matter and purpose referenced herein. Other gRNA sequences may be designed using the CD70 gene sequence located on chromosome 19 (GRCh38: chromosome 19: 6,583,183-6,604, 103; Ensembl; ENSG00000125726).

In some embodiments, gRNAs targeting the CD70 genomic region and Cas9 create breaks in the CD70 genomic region resulting Indels in the CD70 gene disrupting expression of the mRNA or protein. In some embodiments, gRNAs targeting the CD70 genomic region create Indels in the CD70 gene comprising at least one nucleotide sequence selected from the sequences in Table 11. In some embodiments, gRNA (SEQ ID NO: 2) targeting the CD70 genomic region creates Indels in the CD70 gene comprising at least one nucleotide sequence selected from the sequences in Table 11.

An exemplary gRNA targeting a TRAC gene is provided in SEQ ID NO: 6. See also International Application No. PCT/IB2018/001619, filed May 11, 2018, which published as WO2019/097305A2, the relevant disclosures of which are incorporated by reference herein for the subject matter and purpose referenced herein. Other gRNA sequences may be designed using the TRAC gene sequence located on chromosome 14 (GRCh38: chromosome 14: 22,547,506-22, 552,154; Ensembl; ENSG00000277734).

In some embodiments, gRNAs targeting the TRAC genomic region and Cas9 create breaks in the TRAC genomic region resulting Indels in the TRAC gene disrupting expression of the mRNA or protein. In some embodiments, gRNAs targeting the TRAC genomic region create Indels in the TRAC gene comprising at least one nucleotide sequence selected from the sequences in Table 9. In some embodiments, gRNA (SEQ ID NO: 6) targeting the TRAC genomic region creates Indels in the TRAC gene comprising at least one nucleotide sequence selected from the sequences in Table 9.

An exemplary gRNA targeting a β2M gene is provided in SEQ ID NO: 10. See also International Application No. PCT/IB2018/001619, filed May 11, 2018, which published as WO2019/097305A2, the relevant disclosures of which are incorporated by reference herein for the purpose and subject matter referenced herein. Other gRNA sequences may be designed using the β2M gene sequence located on Chromosome 15 (GRCh38 coordinates: Chromosome 15: 44,711,477-44,718,877; Ensembl: ENSG00000166710).

In some embodiments, gRNAs targeting the 132M genomic region and RNA-guided nuclease create breaks in the β2M genomic region resulting in Indels in the β2M gene disrupting expression of the mRNA or protein. In some embodiments, gRNAs targeting the 132M genomic region create Indels in the β2M gene comprising at least one nucleotide sequence selected from the sequences in Table 10. In some embodiments, gRNA (SEQ ID NO: 10) targeting the 132M genomic region creates Indels in the β2M gene comprising at least one nucleotide sequence selected from the sequences in Table 10.

In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA molecules. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins. A single-molecule guide RNA in a Type V system comprises, in the 5' to 3' direction, a minimum CRISPR repeat sequence and a spacer sequence.

The "target sequence" is in a target gene that is adjacent to a PAM sequence and is the sequence to be modified by Cas9. The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence.

For example, if the CD70 target sequence is 5'-GCTTTGGTCCCATTGGTCGC-3' (SEQ ID NO: 15), then the gRNA spacer sequence is GCUUUGGUCCCAUUGGUCGC-3' (SEQ ID NO: 5). In another example, if the TRAC target sequence is 5'-AGAGCAACAGTGCTGTGGCC-3' (SEQ ID NO: 17), then the gRNA spacer sequence is 5'-AGAGCAACAGUGCUGUGGCC-3' (SEQ ID NO: 9). In yet another example, if the 132M target sequence is 5'-GCTACTCTCTCTTTCTGGCC-3' (SEQ ID NO: 19), then the gRNA spacer sequence is 5'-GCUACUCUCUCUUUCUGGCC-3' (SEQ ID NO: 13). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM recognizable by a Cas9 enzyme used in the system. The spacer may perfectly match the target sequence or may have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence is the *S. pyogenes* PAM.

A spacer sequence in a gRNA is a sequence (e.g., a 20 nucleotide sequence) that defines the target sequence (e.g., a DNA target sequences, such as a genomic target sequence) of a target gene of interest. An exemplary spacer sequence of a gRNA targeting a CD70 gene is provided in SEQ ID NO: 4. An exemplary spacer sequence of a gRNA targeting a TRAC gene is provided in SEQ ID NO: 8. An exemplary spacer sequence of a gRNA targeting a β2M gene is provided in SEQ ID NO: 12.

The guide RNA disclosed herein may target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene is 100% complementary. In other embodiments, the spacer sequence of the guide RNA and the target sequence in the target gene may contain up to 10 mismatches, e.g., up to 9, up to 8, up to 7, up to 6, up to 5, up to 4, up to 3, up to 2, or up to 1 mismatch.

Non-limiting examples of gRNAs that may be used as provided herein are provided in PCT/IB2018/001619, filed May 11, 2018, which published as WO2019/097305A2, and PCT/IB2019/000500, filed May 10, 2019, now published as WO2019/215500, the relevant disclosures of each of the prior applications are herein incorporated by reference for the purposes and subject matter referenced herein. For any of the gRNA sequences provided herein, those that do not explicitly indicate modifications are meant to encompass both unmodified sequences and sequences having any suitable modifications.

The length of the spacer sequence in any of the gRNAs disclosed herein may depend on the CRISPR/Cas9 system and components used for editing any of the target genes also disclosed herein. For example, different Cas9 proteins from different bacterial species have varying optimal spacer sequence lengths. Accordingly, the spacer sequence may have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence may have 18-24 nucleotides in length. In some embodiments, the targeting sequence may have 19-21 nucleotides in length. In some embodiments, the spacer sequence may comprise 20 nucleotides in length.

In some embodiments, the gRNA can be a sgRNA, which may comprise a 20 nucleotide spacer sequence at the 5' end of the sgRNA sequence. In some embodiments, the sgRNA may comprise a less than 20 nucleotide spacer sequence at the 5' end of the sgRNA sequence. In some embodiments, the sgRNA may comprise a more than 20 nucleotide spacer sequence at the 5' end of the sgRNA sequence. In some embodiments, the sgRNA comprises a variable length spacer sequence with 17-30 nucleotides at the 5' end of the sgRNA sequence. Examples are provided in Table 8 in Example 5.

In some embodiments, the sgRNA comprises no uracil at the 3' end of the sgRNA sequence. In other embodiments, the sgRNA may comprise one or more uracil at the 3' end of the sgRNA sequence. For example, the sgRNA can comprise 1-8 uracil residues, at the 3' end of the sgRNA sequence, e.g., 1, 2, 3, 4, 5, 6, 7, or 8 uracil residues at the 3' end of the sgRNA sequence.

Any of the gRNAs disclosed herein, including any of the sgRNAs, may be unmodified. Alternatively, it may contain one or more modified nucleotides and/or modified backbones. For example, a modified gRNA such as an sgRNA can comprise one or more 2'-O-methyl phosphorothioate nucleotides, which may be located at either the 5' end, the 3' end, or both.

In certain embodiments, more than one guide RNAs can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

It should be understood that more than one suitable Cas9 and more than one suitable gRNA can be used in methods described herein, for example, those known in the art or disclosed herein. In some embodiments, methods comprise a Cas9 enzyme and/or a gRNA known in the art. Examples can be found in, e.g., PCT/IB2018/001619, filed May 11, 2018, which published as WO 2019/097305A2, and PCT/IB2019/000500, filed May 10, 2019, now published as WO2019/215500, the relevant disclosures of each of the prior applications are herein incorporated by reference for the purposes and subject matter referenced herein.

Gene Editing of CD70, TRAC and β2M Genes

In some embodiments, the enriched T cells as disclosed herein may be subjected to gene editing of the CD70 gene, the TRAC gene, and the (32M gene via CRISPR-Cas9-mediated gene editing under conditions disclosed herein, which would result in higher and more consistent gene editing efficiencies and lower translocation rates compared to those provided by conventional conditions.

In specific examples, the RNP complex targeting the CD70 gene may comprise about 0.15 mg/ml Cas9 (e.g., the Cas9 of SEQ ID NO:1) and about 0.16 mg/ml of a gRNA targeting the CD70 gene (e.g., the gRNA of CD70-7). RNPs are useful for gene editing, at least because they minimize the risk of promiscuous interactions in a nucleic acid-rich cellular environment and protect the RNA from degradation. Methods for forming RNPs are known in the art.

RNPs targeting CD70 disclosed herein may be introduced into the enriched T cells by mixing the RNPs with a suitable amount of the enriched T cells and the mixture thus formed is subject to electroporation under suitable conditions allowing for delivery of the RNPs into the cells. In some instances, a suitable amount of the enriched T cells may range from about $100\times10^6$ cells/mL to about $400\times10^6$ cells/mL. For example, a suitable amount of the T cells for the first electroporation step may range from about $200\times10^6$ cells/mL to about $350\times10^6$ cells/mL. In some embodiments, the concentration of the enriched T cells may be about $100\times10^6$ cells/mL. In some embodiments, the concentration of enriched T cells may be about $200\times10^6$ cells/mL. In some embodiments, the concentration of enriched T cells may be about $300\times10^6$ cells/mL or about $350\times10^6$ cells/mL.

After electroporation, the T cells having the CD70 gene disrupted may be cultured in a fresh medium for a suitable period for recovery. Gene editing efficiency may be performed following routine practice. The genetically edited T cells thus produced may be subjected to a T cell activation step to improve downstream gene editing efficiencies and T cell expansion step.

The TRAC gene encodes a component of the TCR complex. Disruption of the TRAC gene leads to loss of function of the TCR and renders the engineered T cell non-alloreactive and suitable for allogeneic transplantation, minimizing the risk of graft versus host disease. The β2M gene encodes a common (invariant) component of the major histocompatibility complex (MHC) I complexes. Disrupting the β2M gene can prevent host versus therapeutic allogeneic T cells responses. Knocking out both the TRAC gene and the β2M gene would result in production of allogeneic T cells for use in cell therapy.

In some embodiments, the manufacturing methods disclosed herein may comprise multiple gene editing steps to sequentially edit the target genes (CD70, TRAC, and β2M) in the T cells and to introduce the CAR-coding nucleic acid into the T cells for expression. Each gene editing step may involve an electroporation step for introducing into the T cells guide RNAs, Cas9 enzyme(s), and/or CAR-coding nucleic acids for genetic editing the target genes (CD70, TRAC, and 132M) and for CAR expression in the T cells.

In some embodiments, CD70 is edited in a first electroporation event, and β2M/TRAC are edited in a second electroporation event. See, e.g., FIG. 3A. However, it is not intended that the methods described herein to be limited to that sequence of steps. The data provided in FIGS. 2A and 2B suggest that both the guides for CD70 and β2M delivered in the first electroporation beneficially led to lower translocation rates. Thus, in other embodiments, both CD70 and 132M can be targeted in the first electroporation event.

In some instances, one or more guide RNAs targeting the CD70 gene and a Cas9 enzyme may be introduced into the T cells to disrupt the CD70 gene in a first electroporation step, and one or more guide RNAs targeting the TRAC and 132M genes, a Cas9 enzyme, and a CAR-coding nucleic acid may be introduced into the T cells in a second electroporation step, following the first electroporation step, to disrupt the TRAC and 132M genes and to introduce the CAR-coding nucleic acid into the T cells. In some examples, the T cells may be subject to activation using one or more T cell activating agents, e.g., those described herein after the $1^{st}$ electroporation step and prior to the $2^{nd}$ electroporation step. As shown in Example 3 below, this design allows for effective genetic editing of at least the 132M gene in the second electroporation step, while maintaining a high level of T cells having a disrupted CD70 gene resulting from the first electroporation step.

In a first gene editing step, a first RNP complex comprising a first Cas9 enzyme and a first gRNA targeting a CD70 gene is introduced into enriched T cells to produce T cells having the CD70 gene disrupted. Such T cells may be activated prior to performing a second gene editing step to attenuate cell loss resulting from the first gene editing step.

In a second gene editing step, a second RNP complex comprising a second Cas9 enzyme and a second gRNA targeting a TRAC gene, and a third RNP complex comprising a third Cas9 enzyme and a third gRNA targeting a β2M gene are introduced into T cells to produce T cells having the CD70, the TRAC, the β2M genes disrupted. The Cas9 enzyme and the gRNAs targeting the TRAC gene and β2M gene may form one or more ribonucleoprotein (RNP) complexes, which can be delivered into the activated T cells having the CD70 gene disrupted as disclosed herein.

In some embodiments, the second RNP complex and the third RNP complex introduced into the T cells having a disrupted CD70 gene, which may optionally activated, may contain the same amount of the Cas9 enzyme. For example, both the second RNP complex and the third RNP complex may comprise about 0.1-0.3 mg/ml (e.g., about 0.1-0.2 mg/mi) of the Cas9 enzyme (e.g., the Cas9 enzyme of SEQ ID NO:1). In some examples, each of the second RNP complex and the third RNP complex may comprise about 0.15 mg/ml of the Cas9 enzyme, which may be the Cas9 enzyme of SEQ ID NO:1.

In other embodiments, the second RNP complex and the third RNP complex may contain different amounts of the Cas9 enzyme. In some examples, the second RNP complex targeting the TRAC gene may comprise a higher amount of the Cas9 enzyme relative to the third RNP complex targeting the β2M gene. Alternatively, the second RNP complex targeting the β2M gene may comprise a higher amount of the Cas9 enzyme relative to the third RNP complex targeting the TRAC gene.

The second RNP complex and the third RNP complex may comprise the same amount of the gRNAs (one targeting TRAC and the other targeting β2M). Alternatively, the second RNP complex and the third RNP complex may comprise different amounts of the gRNAs. For example, the amount of the gRNA targeting the TRAC gene may range from about 0.035 mg/ml to about 0.8 mg/ml, for example, about 50 μg/ml to about 80 μg/ml. In specific examples, the amount of the gRNA targeting the TRAC gene is about 0.08 mg/ml. Alternatively, or in addition, the amount of the gRNA targeting the β2M gene may range from about 0.075 mg/ml to about 0.3 mg/ml, for example, about 0.1 mg/ml to about 0.3 mg/ml. In specific examples, the amount of the gRNA targeting the β2M gene is about 0.2 mg/ml.

In specific examples, the RNP complex targeting the TRAC gene may comprise about 0.15 mg/ml Cas9 (e.g., the Cas9 of SEQ ID NO:1) and about 0.08 mg/ml of a gRNA targeting the TRAC gene (e.g., the gRNA of TA-1). Alternatively or in addition, the RNP complex targeting the β2M gene may comprise about 0.15 mg/ml Cas9 (e.g., the Cas9 of SEQ ID NO:1) and about 0.2 mg/ml of a gRNA targeting the β2M gene (e.g., the gRNA of β2M-1).

In some embodiments, the second RNP complex and the third RNP complex may be introduced into the activated T cell via electroporation sequentially, i.e., via two electroporation events. Alternatively, the second RNP complex and the third RNP complex may be introduced into the activated T cells simultaneously, i.e., via one electroporation event. In this case, the second RNP complex and the third RNP complex may be combined to form a mixture prior to the electroporation event.

Any of the RNPs disclosed herein may be introduced into the activated T cells by mixing the RNP(s) with a suitable amount of the activated T cells and the mixture thus formed is subject to electroporation under suitable conditions allowing for delivery of the RNPs into the cells. In some instances, the suitable amount of the activated T cells may range from about $100\times10^6$ cells/mL to about $300\times10^6$ cells/mL. For example, suitable amount of the T cells for the electroporation step may range from about $200\times10^6$ cells/mL to about $300\times10^6$ cells/mL. In some examples, the concentration of the activated T cells may be about $100\times10^6$ cells/mL. In some embodiments, the concentration of activated T cells may be about $200\times10^6$ cells/mL. In some embodiments, the concentration of activated T cells may be about $300\times10^6$ cells/mL.

In some embodiments, the suitable amount of the activated T cells may range from about $1\times10^8$ to about $1\times10^{10}$ cells, e.g., about $5\times10^8$ to about $8\times10^9$ cells, about $1\times10^9$ to about $5\times10^9$ cells, or about $1\times10^9$ to about $3\times10^9$ cells.

The T cells for use in electroporation may be placed in multiple cell cassettes, depending upon the electroporation instrument used. Suitable electroporation instruments are known to those skilled in the art and could include static and flow electroporators, including the Lonza Nucleofector, Maxcyte GT, and MaxCyte GTx. In some instances, multiple cell cassettes may be used in an electroporation process. More details are provided in Example 6 below.

In specific examples, the second RNP complex and the third RNP complex disclosed above, comprising about 0.3 mg/ml of the Cas9 enzyme in total (e.g., the Cas9 enzyme of SEQ ID NO:1), about 0.08 mg/ml of the gRNA of TA-1, and about 0.2 mg/ml of the gRNA of β2M-1, may be mixed with the activated T cells in the amount of about $100\times10^6$ cells/mL to about $400\times10^6$ cells/mL (e.g., about $300\times10^6$ cells/mL). The mixture is then subject to electroporation for delivery of the RNPs into the T cells.

In some examples, the first Cas9 enzyme, the second Cas9 enzyme and the third Cas9 enzyme are the same, e.g., Cas9 from *Streptococcus pyogenes* (spCas9) or a Cas9 enzyme comprising the amino acid sequence of SEQ ID NO: 1.

After electroporation, the cells may be cultured in a fresh medium for a suitable period for recovery. Gene editing efficiency may be determined following routine practice. The genetically edited T cells thus produced may be subjected to viral vector transduction for delivery of a nucleic acid configured for CAR expression.

(iii) T Cell Activation

Any of the T cells disclosed herein, for example, the T cells having the CD70 gene disrupted resulting from the 1" electroporation step, may be subjected to an activation step to allow for T cell proliferation and T cell expansion. T cell activation conditions disclosed herein provide high T cell activation efficiency, high % $CAR^+$ expression, and attenuate cell loss resulting from editing of the CD70 gene. Further, T cell activation conditions disclosed herein provided higher gene editing efficiencies and greater rates of T cell expansion post editing compared to conventional conditions. See Examples below.

In some embodiments, T cell activation can be achieved using T cell activating agents, for example, agents that stimulates a CD3/TCR-mediated signaling pathway and/or a co-stimulatory molecule (e.g., CD28) mediated signaling pathway. For example, a T cell activating agent may be a CD3 agonist (e.g., an agonistic anti-CD3 antibody) and activates the CD3/TCR-mediated cell signaling pathway. Alternatively or in addition, a T cell activating agent may be a CD28 agonist (e.g., an anti-CD28 antibody) and activates the co-stimulatory signaling pathway mediated by CD28. Any of the T cell activating agents for use in the method disclosed herein may be conjugated to a support member, such as a nanomatrix particle. In such situations, the T cell activating agents may be conjugated to the same support member. Alternatively, each T cell activating agent may be conjugated to a different support member. In specific examples, the T cell activating agent for use in the method disclosed herein may comprise an anti-CD3 antibody and an anti-CD28 antibody, which may be conjugated to nanomatrix particles. In some embodiments, the T cell activating agent comprises a CD3 agonist and a CD28 agonist attached to a nanomatrix particle. In some embodiments, the CD3 agonist and a CD28 agonist are attached to the same nanomatrix particle. In some embodiments, the CD3 agonist and a CD28 agonist are attached to different nanomatrix particles.

To achieve T cell activation, the T cells having the CD70 gene disrupted as disclosed herein may be placed in a cell culture vessel at a suitable cell seeding density and a suitable cell concentration and incubated in the presence of any of the T cell activating agents disclosed herein for a suitable period to induce T cell activation.

In some instances, ratios of the T cell activating agent to the cell culture medium in the cell culture vessel may range from about 1:10 (v/v) to about 1:15 (v/v). In some examples, the ratio of the T cell activating agent to the cell culture medium in the cell culture vessel may be about 1:10 (v/v), about 1:10.5 (v/v), about 1:11 (v/v), about 1:11.5 (v/v), about 1:12 (v/v), about 1:12.5 (v/v), about 1:13 (v/v), about 1:13.5 (v/v), about 1:14 (v/v), about 1:14.5 (v/v), or about 1:15 (v/v). In specific examples, the ratio of the T cell activating agent to the culture medium in the cell culture vessel is about 1:12.5 (v/v).

Alternatively or in addition, a suitable cell seeding density may be about $1.0\times10^6$ to $2.5\times10^6$ (e.g., $2\times10^6/cm^2$) and a suitable cell concentration may be about $1.0\times10^6$ to $2.5\times10^6$ (e.g., $2\times10^6$/ml). The T cells having the CD70 gene disrupted may be incubated with the T cell activating agent for about 60-80 hours, for example, about 66 hours or about 72 hours.

Alternatively or in addition, a suitable cell seeding density may be about $1.5\times10^6$ to $2.5\times10^6$ (e.g., $2\times10^6/cm^2$) and a suitable cell concentration may be about $1.5\times10^6$ to $2.5\times10^6$ (e.g., $2\times10^6$/ml). The T cells having the CD70 gene disrupted may be incubated with the T cell activating agent for about 66-80 hours, for example, about 72 hours.

In some embodiments, the cell culture vessel may be a static culture vessel, which would allow for relatively large-scale production of the genetically engineered T cells as disclosed herein. Compared to conventional cell culture flasks, static cell culture vessels allow T cells to reside on a highly gas permeable membrane submerged under medium that supplies oxygen and nutrients to the T cells without mixing or shaking. Static culture vessels allow T cell manufacturing without medium change. Accordingly, in some embodiments, the T cell activation process in any of the methods disclosed herein may involve no medium change.

When needed, the activating agent may be removed from the cell culture vessel or diluted prior to the downstream gene editing events to minimize any potential impact that the activating agent may confer during gene editing. In some embodiments, the activating agent can be removed from the cell culture vessel using routine methods, e.g., centrifugation. Alternatively, the activating agent may be diluted in the cell culture vessel prior to gene editing, e.g., diluted by addition of media to the cell culture vessel.

In some embodiments, the activated T cells having the CD70 gene disrupted derived from any of the T cell activation processes disclosed herein may be cultured overnight (e.g., about 16 hours) to allow T cells to recover prior to gene editing. In some instances, a culture of activated T cells having the CD70 gene disrupted may still contain the T cell activating agent. In other instances, the culture of activated T cells having the CD70 gene disrupted may have little or no presence of the T cell activating agent.

(iv) T Cell Transduction

The genetically edited T cells, having CD70, TRAC, and/or β2M genes knocked out, may be subject to transduction with a viral vector such as an adeno-associated viral (AAV) vector that comprises a nucleic acid sequence encoding a chimeric antigen receptor (CAR) to produce a population of T cells expressing the CAR.

Chimeric Antigen Receptor (CAR)

A chimeric antigen receptor (CAR) refers to an artificial immune cell receptor that is engineered to recognize and bind to an antigen expressed by undesired cells, for example, disease cells such as cancer cells. A T cell that expresses a CAR polypeptide is referred to as a CAR T cell. CARs have the ability to redirect T-cell specificity and reactivity toward a selected target in a non-MHC-restricted manner. The non-MHC-restricted antigen recognition gives CAR-T cells the ability to recognize an antigen independent of antigen processing, thus bypassing a major mechanism of tumor escape. Moreover, when expressed on T-cells, CARs advantageously do not dimerize with endogenous T-cell receptor (TCR) alpha and beta chains.

There are various generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional co-stimulatory domain, e.g., CD28, 4-1 BB (41 BB), or ICOS, to supply a costimulatory signal. Third-generation CARs contain two costimulatory domains (e.g., a combination of CD27, CD28, 4-1 BB, ICOS, or OX40) fused with the TCR CD3ζ chain. Maude et al., Blood. 2015; 125(26):4017-4023; Kakarla and Gottschalk, Cancer J. 2014; 20(2):151-155). Any of the various generations of CAR constructs is within the scope of the present disclosure.

Generally, a CAR is a fusion polypeptide comprising an extracellular domain that recognizes a target antigen (e.g., a single-chain variable fragment (scFv) of an antibody or other antibody fragment) and an intracellular domain comprising a signaling domain of the T-cell receptor (TCR) complex (e.g., CD3ζ) and, in most cases, a co-stimulatory domain. (Enblad et al., Human Gene Therapy. 2015; 26(8): 498-505). A CAR construct may further comprise a hinge and transmembrane domain between the extracellular domain and the intracellular domain, as well as a signal peptide at the N-terminus for surface expression. Examples of signal peptides include MLLLVTSLLLCELPHPAFLLIP (SEQ ID NO: 52) and MALPVTALLLPLALLLHAARP (SEQ ID NO: 53). Other signal peptides may be used.

(a) Antigen Binding Extracellular Domain

The antigen-binding extracellular domain is the region of a CAR polypeptide that is exposed to the extracellular fluid when the CAR is expressed on cell surface. In some instances, a signal peptide may be located at the N-terminus to facilitate cell surface expression. In some embodiments, the antigen binding domain can be a single-chain variable fragment (scFv, which may include an antibody heavy chain variable region ($V_H$) and an antibody light chain variable region ($V_L$) (in either orientation). In some instances, the $V_H$ and $V_L$ fragment may be linked via a peptide linker. The linker, in some embodiments, includes hydrophilic residues with stretches of glycine and serine for flexibility as well as stretches of glutamate and lysine for added solubility. The scFv fragment retains the antigen-binding specificity of the parent antibody, from which the scFv fragment is derived. In some embodiments, the scFv may comprise humanized $V_H$ and/or $V_L$ domains. In other embodiments, the $V_H$ and/or $V_L$ domains of the scFv are fully human.

The antigen-binding extracellular domain may be specific to a target antigen of interest, for example, a pathologic antigen such as a tumor antigen. In some embodiments, a tumor antigen is a "tumor associated antigen," referring to an immunogenic molecule, such as a protein, that is generally expressed at a higher level in tumor cells than in non-tumor cells, in which it may not be expressed at all, or only at low levels. In some embodiments, tumor-associated structures, which are recognized by the immune system of the tumor-harboring host, are referred to as tumor-associated antigens. In some embodiments, a tumor-associated antigen is a universal tumor antigen, if it is broadly expressed by most types of tumors. In some embodiments, tumor-associated antigens are differentiation antigens, mutational antigens, overexpressed cellular antigens or viral antigens. In some embodiments, a tumor antigen is a "tumor specific antigen" or "TSA," referring to an immunogenic molecule, such as a protein, that is unique to a tumor cell. Tumor specific antigens are exclusively expressed in tumor cells, for example, in a specific type of tumor cells.

In some examples, the CAR constructs disclosed herein comprise a scFv extracellular domain capable of binding to CD70. In some examples, the CAR constructs disclosed herein comprise a scFv extracellular domain capable of binding to CD19. In some examples, the CAR constructs disclosed herein comprise a scFv extracellular domain capable of binding to BCMA. An example of an anti-CD70 CAR is provided in Examples below.

(b) Transmembrane Domain

The CAR polypeptide disclosed herein may contain a transmembrane domain, which can be a hydrophobic alpha helix that spans the membrane. As used herein, a "transmembrane domain" refers to any protein structure that is thermodynamically stable in a cell membrane, preferably a eukaryotic cell membrane. The transmembrane domain can provide stability of the CAR containing such.

In some embodiments, the transmembrane domain of a CAR as provided herein can be a CD8 transmembrane domain. In other embodiments, the transmembrane domain can be a CD28 transmembrane domain. In yet other embodiments, the transmembrane domain is a chimera of a CD8 and CD28 transmembrane domain. Other transmembrane domains may be used as provided herein. In some embodiments, the transmembrane domain is a CD8a transmembrane domain containing the sequence of

```
                                  (SEQ ID NO: 54)
FVPVFLPAKPTTTPAPRPPTPAPTIASQPLSLRPEACRPAAGG

AVHTRGLDFACDIYIWAPLAGTCGVLLLSLVITLYCNHRNR
or

                                  (SEQ ID NO: 55)
IYIWAPLAGTCGVLLLSLVITLY.
```

Other transmembrane domains may be used.

(c) Hinge Domain

In some embodiments, a hinge domain may be located between an extracellular domain (comprising the antigen binding domain) and a transmembrane domain of a CAR, or between a cytoplasmic domain and a transmembrane domain of the CAR. A hinge domain can be any oligopeptide or polypeptide that functions to link the transmembrane domain to the extracellular domain and/or the cytoplasmic domain in the polypeptide chain. A hinge domain may function to provide flexibility to the CAR, or domains thereof, or to prevent steric hindrance of the CAR, or domains thereof.

In some embodiments, a hinge domain may comprise up to 300 amino acids (e.g., 10 to 100 amino acids, or 5 to 20 amino acids). In some embodiments, one or more hinge domain(s) may be included in other regions of a CAR. In some embodiments, the hinge domain may be a CD8 hinge domain. Other hinge domains may be used.

(d) Intracellular Signaling Domains

Any of the CAR constructs contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3ζ contains three (3) immunoreceptor tyrosine-based activation motif (ITAM)s, which transmit an activation signal to the T cell after the T cell is engaged with a cognate antigen. In many cases, CD3ζ provides a primary T cell activation signal but not a fully competent activation signal, which requires a co-stimulatory signaling.

In some embodiments, the CAR polypeptides disclosed herein may further comprise one or more co-stimulatory signaling domains. For example, the co-stimulatory domains of CD28 and/or 4-1 BB may be used to transmit a full proliferative/survival signal, together with the primary signaling mediated by CD3ζ. In some examples, the CAR disclosed herein comprises a CD28 co-stimulatory molecule. In other examples, the CAR disclosed herein comprises a 4-1 BB co-stimulatory molecule. In some embodiments, a CAR includes a CD3ζ signaling domain and a CD28 co-stimulatory domain. In other embodiments, a CAR includes a CD3ζ signaling domain and 4-1 BB co-stimulatory domain. In still other embodiments, a CAR includes a CD3 signaling domain, a CD28 co-stimulatory domain, and a 4-1 BB co-stimulatory domain.

It should be understood that methods described herein encompasses more than one suitable CAR that can be used to produce genetically engineered T cells expressing the CAR, for example, those known in the art or disclosed herein. Examples can be found in, e.g., PCT/IB2018/001619, filed May 11, 2018, which published as WO 2019/097305A2, and PCT/IB2019/000500, filed May 10, 2019, the relevant disclosures of each of the prior applications are herein incorporated by reference for the purposes and subject matter referenced herein.

For example, the CAR binds CD70 (also known as a "CD70 CAR" or an "anti-CD70 CAR"). The amino acid sequence of an exemplary CAR that binds CD70 is provided in SEQ ID NO: 46 (see Table 12 in Example 5 below).

AAV Vectors for Delivery of CAR Constructs to T Cells

A nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV for use in delivering the CAR-coding nucleic acid is AAV serotype 6 (AAV6).

Adeno-associated viruses are among the most frequently used viruses for gene therapy for several reasons. First, AAVs do not provoke an immune response upon administration to mammals, including humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

A nucleic acid encoding a CAR can be designed to insert into a genomic site of interest in the host T cells. In some embodiments, the target genomic site can be in a safe harbor locus.

In some embodiments, a nucleic acid encoding a CAR (e.g., via a donor template, which can be carried by a viral vector such as an adeno-associated viral (AAV) vector) can be designed such that it can insert into a location within a TRAC gene to disrupt the TRAC gene in the genetically engineered T cells and express the CAR polypeptide. Disruption of TRAC leads to loss of function of the endogenous TCR. For example, a disruption in the TRAC gene can be created with an endonuclease such as those described herein and one or more gRNAs targeting one or more TRAC genomic regions. Any of the gRNAs specific to a TRAC gene and the target regions can be used for this purpose, e.g., those disclosed herein.

In some examples, a genomic deletion in the TRAC gene and replacement by a CAR coding segment can be created by homology directed repair or HDR (e.g., using a donor template, which may be part of a viral vector such as an adeno-associated viral (AAV) vector). In some examples, the gRNA target sequence, or portion thereof, is deleted (eg: SEQ ID NO: 17). In some embodiments, a disruption in the TRAC gene can be created with an endonuclease as those disclosed herein and one or more gRNAs targeting one or more TRAC genomic regions, and inserting a CAR coding segment into the TRAC gene.

A donor template as disclosed herein can contain a coding sequence for a CAR. In some examples, the CAR-coding sequence may be flanked by two regions of homology to allow for efficient HDR at a genomic location of interest, for example, at a TRAC gene using CRISPR-Cas9 gene editing technology. In this case, both strands of the DNA at the target locus can be cut by a CRISPR Cas9 enzyme guided by gRNAs specific to the target locus. HDR then occurs to repair the double-strand break (DSB) and insert the donor DNA coding for the CAR. For this to occur correctly, the donor sequence is designed with flanking residues which are complementary to the sequence surrounding the DSB site in the target gene (hereinafter "homology arms"), such as the TRAC gene. These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced into a cell as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

A donor template, in some embodiments, can be inserted at a site nearby an endogenous promoter (e.g., downstream or upstream) so that its expression can be driven by the endogenous promoter. In other embodiments, the donor template may comprise an exogenous promoter and/or enhancer, for example, a constitutive promoter, an inducible promoter, or tissue-specific promoter to control the expression of the CAR gene. In some embodiments, the exogenous promoter is an EF1$\alpha$ promoter. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

T Cell Transduction

A suitable amount of any of the viral vectors such as an AAV vector, which encodes a CAR construct disclosed herein (e.g., an anti-CD70 CAR) may be incubated with a suitable amount of T cells, such as the genetically edited T cells disclosed herein for a suitable period to allow for entry of the viral vector into the T cells. For example, the transduction process may involve the use of a range of optimized multiplicity of infection (MOI) that increases percentages of CAR$^+$ T cells. In some instances, the MOI of an AAV vector in the transduction process may range from about 1,000 to about 150,000, such as from about 10,000 to about 80,000. In some examples, the MOI of the AAV vector used in the transduction process may be about 1,000 to about 150,000, about 5,000 to about 100,000, about 10,000 to about 100,000, about 10,000 to about 90,000, about 10,000 to about 80,000, about 10,000 to about 70,000, about 10,000 to about 60,000, about 10,000 to about 50,000, about 10,000 to about 40,000, about 10,000 to about 30,000, about 10,000 to about 20,000, about 20,000 to about 80,000, about 30,000 to about 80,000, about 40,000 to about 80,000, about 50,000 to about 80,000, about 60,000 to about 80,000, or about 70,000 to about 80,000. In some examples, the MOI of the AAV vector used in the transduction process may be about 1,000, about 2,500, about 5,000, about 10,000, about 15,000, about 20,000, about 25,000, about 30,000, about 31,000, about 32,000, about 33,000, about 34000, about 35,000, about 40,000, about 50,000, about 60,000, about 70,000, about 80,000, about 90,000, about 100,000, about 110,000, about 120,000, about 130,000, about 140,000, or about 150,000.

In some embodiments, the AAV vector encodes an anti-CD70 CAR (e.g., as disclosed in Table 12 in Example 5 below) and the MOI of such an AAV vector for use in the transduction process is about 20,000. In other embodiments, the AAV vector encodes an anti-CD19 CAR and the MOI of such an AAV vector for use in the transduction process is about 20,000. In other embodiments, the AAV vector encodes an anti-BCMA CAR and the MOI of such an AAV vector for use in the transduction process is about 20,000.

After transduction, the T cells may be cultured in a suitable cell culture medium for a suitable period for recovery. The genetically engineered T cells, having CD70, TRAC, and β2M genes knocked-out and expressing the CAR, may be expanded in vitro as disclosed below.

(v) T Cell Expansion

The genetically engineered T cells as disclosed herein may be expanded in vitro under suitable conditions to produce a population of genetically engineered T cells to a clinically relevant scale. Cell culture conditions used in this expansion step intend to, at least in part, achieve higher final cell densities in shorter incubation periods (thereby reducing manufacturing cost) and higher potent T cells for use in cell therapy. Potency may be indicated by various T cell functions, e.g., proliferation, target cell killing, cytokine production, activation, migration, and combinations thereof.

In some embodiments, the T cell expansion step may be performed by seeding a population of T cells (e.g., the genetically engineered T cells as disclosed herein) in a cell culture vessel at a seeding density of about 150,000 cells/$cm^2$ to about 600,000 cells/$cm^2$ in a cell vessel. For example, the T cells may be seeded at about 300,000 cells/$cm^2$ to about 500,000 cells/$cm^2$, in a cell vessel. In some aspects, the T cell expansion is performed by seeding a population of T cells in a cell culture vessel at a seeding density of at least about 60,000 cells/$cm^2$, at least about 62,500 cells/$cm^2$, or at least about 83,000 cells/$cm^2$. In some aspects, the T cell expansion is performed by seeding a population of T cells in a cell culture vessel at a seeding density of at least about 150,000 cells/$cm^2$, or at least about 250,000 cells/$cm^2$, or at least about 300,000 cells/$cm^2$, or at least about 400,000 cells/$cm^2$, or at least about 500,000 cells/$cm^2$, or at least about 600,000 cells/$cm^2$. In some aspects, the seeding density is about 250,000 cells/$cm^2$. In other aspects, the seeding density is about 500,000 cells/$cm^2$. In other aspects, the seeding density is about 600,000 cells/$cm^2$.

In some embodiments, the T cell expansion step may be performed by seeding a population of T cells (e.g., the genetically engineered T cells as disclosed herein) in a cell culture vessel at a seeding density of about $2\times10^5$ cells/$cm^2$ to about $7\times10^5$ cells/$cm^2$, and culturing the cells for about 6 days to about 12 days. In some examples, the T cell expansion is performed by seeding a population of T cells in a cell culture vessel at a seeding density of about $2\times10^5$ cells/$cm^2$ to about $7\times10^5$ cells/$cm^2$, about $2\times10^5$ cells/$cm^2$ to about $5\times10^5$ cells/$cm^2$, about $2\times10^5$ cells/$cm^2$ to about $4\times10^5$ cells/$cm^2$, $2\times10^5$ cells/$cm^2$ to about $3\times10^5$ cells/$cm^2$, $3\times10^5$ cells/$cm^2$ to about $5\times10^5$ cells/$cm^2$, or $4\times10^5$ cells/$cm^2$ to about $5\times10^5$ cells/$cm^2$, and culturing the cells for about 6 days to about 12 days, about 6 days to about 11 days, about 6 days to about 10 days, about 6 days to about 9 days, about 6 days to about 8 days, about 6 days to about 7 days, about 7 days to about 12 days, about 7 days to about 11 days, about 7 days to about 10 days, about 7 days to about 9 days, about 7 days to about 8 days, about 8 days to about 12 days, about 8 days to about 9 days, about 9 days to about 12 days, about 10 days to about 12 days, or about 11 days to about 12 days. In some embodiments, the T cell expansion is performed by seeding a population of T cells in a cell culture vessel at a seeding density of about $3\times10^5$ cells/$cm^2$ to about $5\times10^5$ cells/$cm^2$ and culturing the cells for about 7 days to about 9 days.

In some embodiments, the T cell expansion step may include replating the cell culture (i.e., splitting the cell culture into new culture vessels). In some embodiments, the cell culture can be replated at day 3, 4, 5, 6, or 7 post editing at a 1:4 ratio (1 vessel split into 4 new vessels) for further expansion.

T cell expansion may be performed in a static culture vessel, which allows expansion of the T cells without medium change. For example, T cells can be expanded in a static culture vessel for at about 7 days to about 12 days, or at about 7 days to about 9 days without medium change.

(vi) Depletion of $TCR\alpha\beta^+$ T Cells

In some embodiments, $TCR\alpha\beta^+$ T cells may be depleted from the expanded T cell population disclosed herein to produce a population of allogenic T cells for use in cell therapy. As used herein, "$TCR\alpha\beta^+$ T cell depletion" refers to depleting $TCR\alpha\beta^+$ T cells from a population of cells comprising such. Following $TCR\alpha\beta^+$ T cell depletion, the resultant T cell population may have a substantially low level of $TCR\alpha\beta^+$ T cell (e.g., less than 3% in the total cell population, or less than 2%, less than 1%, or less than 0.5% in the total cell population). In some examples, the resultant T cell population may be free of $TCR\alpha\beta^+$ T cell, i.e., presence of $TCR\alpha\beta^+$ T cell is not dateable via a conventional method (e.g., in an immune assay using an antibody binding to $TCR\alpha\beta^+$ or by flow cytometry).

$TCR\alpha\beta^+$ T cell depletion may be performed using an agent that recognizes $TCR\alpha\beta^+$ T cells to capture the $TCR\alpha\beta^+$ T cells, thereby separating them from those lacking $TCR\alpha\beta^+$, e.g., by performing a magnetic cell separation. Such methods may be carried out by contacting the expanded T cells disclosed above to beads on which anti-$TCR\alpha\beta$ antibodies are immobilized, and collecting unbound cells. Unbound cells (those lacking $TCR\alpha\beta\pm$) thus collected may be cultured to allow cell recovery prior, for example, unbound cells may be cultured overnight to allow cells to recover.

(vii) Harvest of Genetically Engineered T Cells

The genetically engineered T cells produced by any of the methods disclosed herein can then be harvested for therapeutic uses using conventional methods known in the art. For example, harvesting genetically engineered T cells may comprise collecting cells from which $TCR\alpha\beta^+$ has been depleted. The harvested population of genetically engineered T cells may be used as the drug substance. As used herein, a "drug substance" refers to a population of genetically engineered T cells that may be administered to patients. The drug substance may be formulated for therapeutic uses, e.g., formulated in storage media (e.g., CryoStor CS5) and cryopreserved for future use.

Drug substance may be tested for one or more contaminants, e.g., *Mycoplasma*, human viruses (e.g., HIV, HBV, HCV, CMV), and bacterial endotoxins. Alternatively, or in addition to, drug substance may be tested for sterility. Contamination free drug substance may be aliquoted into individual patient doses. Alternatively, or in addition to, contamination free drug substance may be stored for therapeutic use.

Accordingly, aspects of the present disclosure provide a population of genetically engineered T cells (drug substance). The population of genetically engineered T cells has a disrupted CD70 gene, a disrupted TRAC gene, a disrupted β2M gene, and a nucleic acid encoding a CAR, e.g., those described herein. In some embodiments, the CAR binds an antigen expressed on a pathological cell. In some embodiments, the CAR binds CD70. In some embodiments, the CAR binds CD19. In some embodiments, the CAR binds BCMA.

In some embodiments, at least 30%, at least 40%, at least 50%, at least 60%, at least 70%, at least 80%, at least 90%, or at least 95% of the population of genetically engineered T cells produced by the methods described herein express a CAR. In other aspects, these cells that express a CAR further do not express a detectable level of surface CD70 and/or a detectable level of surface TCR and/or a detectable level of surface β2M.

In other embodiments, where at least 30% of the population of genetically engineered T cells produced by methods described herein express a CAR, that population of cells comprises not more than about 5%, not more than about 2%, or not more than about 1%, T cells that express surface CD70.

In other embodiments, where at least 30% of the population of genetically engineered T cells produced by methods described herein express a CAR, that population of cells comprises not more than about 1.0%, not more than about 0.5%, not more than about 0.4%, or not more than about 0.15% T cells that express surface TCR (e.g., TCRα/β+ cells).

In other embodiments, where at least 30% of the population of genetically engineered T cells produced by methods described herein express a CAR, that population of cells comprises not more than about 50%, not more than about 40%, or not more than about 30%, T cells that express surface β2M.

Also within the scope of the present disclosure is a genetically engineered T cell population produced by methods described herein comprising a Cas9 enzyme, a gRNA targeting a CD70 gene, a gRNA targeting a TRAC gene, a gRNA targeting a β2M gene, and an AAV vector comprising a nucleic acid sequence encoding a CAR (e.g., a CD70 CAR or a CD19 CAR or a BCMA CAR).

II. Therapeutic Applications

A population of genetically engineered T cells produced by methods described herein may be administered to a subject for therapeutic purposes, for example, treatment of a cancer targeted by the CAR construct expressed by the population of genetically engineered T cells.

A subject may be any subject for whom diagnosis, treatment, or therapy is desired. In some embodiments, the subject is a mammal. In some embodiments, the subject is a human.

Non-limiting examples of cancers that may be treated using a genetically engineered T cell population produced by methods described herein include, but are not limited to, multiple myeloma, leukemia (e.g., T cell leukemia, B-cell acute lymphoblastic leukemia (B-ALL), and/or chronic lymphocytic leukemia (C-CLL)), lymphoma (e.g., B-cell non-Hodgkin's lymphoma (B-NHL), Hodgkin's lymphoma, and/or T cell lymphoma), and/or clear cell renal cell carcinoma (ccRCC), pancreatic cancer, gastric cancer, ovarian cancer, cervical cancer, breast cancer, renal cancer, thyroid cancer, nasopharyngeal cancer, non-small cell lung (NSCLC), glioblastoma, and/or melanoma.

Administering may include placement (e.g., transplantation) of the genetically engineered T cell population into a subject by a method or route that results in at least partial localization of the genetically engineered T cell population at a desired site, such as a tumor site, such that a desired effect(s) can be produced. The genetically engineered T cell population can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of the genetically engineered T cell population can be administered via a systemic route of administration, such as an intraperitoneal or intravenous route.

In some embodiments, the genetically engineered T cell population is administered systemically, which refers to the administration of a population of cells other than directly into a target site, tissue, or organ, such that it enters, instead, the subject's circulatory system and, thus, is subject to metabolism and other like processes. Suitable modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

An effective amount refers to the amount of a genetically engineered T cell population needed to prevent or alleviate at least one or more signs or symptoms of a medical condition (e.g., cancer), and relates to a sufficient amount of a genetically engineered T cell population to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

An effective amount of a genetically engineered T cell population may comprise at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof.

The efficacy of a treatment using the genetically engineered T cell population manufactured as described herein can be determined by a person of ordinary skill in the art. A treatment is considered "effective", if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

Genetically engineered T cell populations manufactured as described herein may also be used in combination therapies. For example, the genetically engineered T cell population manufactured as described herein may be co-used with other therapeutic agents, for treating the same indication, or for enhancing efficacy of the genetically engineered T cell population and/or reducing side effects of the genetically engineered T cell population.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); *Current Protocols in Immunology* (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985; *Transcription and Translation* (B. D. Hames & S. J. Higgins, eds. (1984; Animal Cell Culture (R. I. Freshney, ed. (1986; *Immobilized Cells and Enzymes* (1RL Press, (1986; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described may be more fully understood, the following examples are set forth. The examples described in this application are offered to illustrate the methods and compositions provided herein and are not to be construed in any way as limiting their scope.

Example 1: Identification of Optimized Conditions for T Cell Enrichment

This Example reports identification of optimized conditions for T cell enrichment, using an automated cell processing system to enrich CD4+ and $CD8^+$ T cells from leukopaks.

Methods

Leukopak and Buffer Preparation

Human leukopaks were collected from HemaCare or Stem Express and processed for T cells enrichment. PBS/EDTA Buffer (phosphate buffered saline, pH 7.2, supplemented with 1 mM EDTA) was supplemented with 0.5% Human Serum Albumin (HSA) and used for processing, priming, washing, and elution during T cell selection.

The leukopak donors were screened for the following:

Hepatitis B Surface Antigen (HBsAg EIA)

Hepatitis C Virus Antibody (Anti-HCV EIA)

Human Immunodeficiency Virus Antibody (HIV 1/2 plus O)

Human T-Lymphotropic Virus Antibody (HTLV-I/II)

HIV-1/HCV/HBV Nucleic Acid Testing

WNV Nucleic Acid Testing

*Trypanosoma cruzi* Antibody (Selective Chagas Disease Testing, a single lifetime test per donor)

HIV/HBV/HCV

CMV

IDS

Donors showing positive results of any of the above tests were excluded.

Demographic information of the donors used in the Examples disclosed herein is shown in Table 1.

TABLE 1

Donor demographic and hematology parameters. All donors were male.

| Batch | Supplier | Donor source ID | Age | Donor weight (lb) | BMI | Ethnicity | ABO/ Rh | Product volume (mL) | WBC ($\times 10^9$) | Lymphocyte % |
|---|---|---|---|---|---|---|---|---|---|---|
| 1 | HemaCare | D327083 | 26 | 144 | 19.0 | Hispanic/ Latino | O- POS | 279 | 9.77 | 79 |
| 2 | HemaCare | 141402 | 29 | 160 | 22.9 | Caucasian | A- POS | 302 | 13.59 | 75.9 |
| 3 | HemaCare | 141121 | 26 | 154 | 24.8 | Hispanic | O- POS | 250 | 8.75 | 74.7 |
| 4 | HemaCare | 136723 | 20 | 130 | 20.9 | Caucasian | A- POS | 305 | 12.81 | 70.1 |
| 5 | HemaCare | D64140 | 28 | 272 | 42.6 | Hispanic/ Latino | A- POS | 339 | 21.36 | 81.1 |
| 6 | Stem Express | D001003864 | 33 | 176 | 24.0 | Caucasian | A- POS | 140 | 8.14 | 70.9 |

TABLE 1-continued

Donor demographic and hematology parameters. All donors were male.

| Batch | Supplier | Donor source ID | Age | Donor weight (lb) | BMI | Ethnicity | ABO/Rh | Product volume (mL) | WBC ($\times 10^9$) | Lymphocyte % |
|---|---|---|---|---|---|---|---|---|---|---|
| 7 | HemaCare | 141722 | 20 | 135 | 19.9 | Hispanic | O-POS | 308 | 13.24 | 78.5 |
| 8 | HemaCare | D327737 | 36 | 200 | 26.4 | African American | B-POS | 310 | 14.57 | 81.3 |
| 9 | HemaCare | D326737 | 31 | 225 | 29.7 | African American | AB-POS | 314 | 10.99 | 77.9 |

Leukopak Hematology Analysis with Sysmex

Samples from incoming leukopaks were processed for hematology analysis with Sysmex XP300 (Sysmex, Serial No: B0628) following manufacturer's instructions. White blood cell (WBC) count was used to calculate the total cell mass loaded into the automated cell processing system.

T Cell Enrichment

Process buffer, leukopak, CD4 microbeads, and CD8 microbeads were loaded in the automated cell processing system prior to starting the run. Cells were washed and labeled in the chamber and directed to the magnet column for separation. CD4+ and $CD8^+$ T cells were captured and further eluted into the target bag in processing buffer.

Cell Count and Viability

Cell count and viability assessment were performed with COUNTESS® II (Life Technologies, Cat: AMQAX1000) using a default profile. Cells (20 μL) were mixed with Trypan blue (20 μL) by pipetting up and down a few times without introducing bubbles. Cell/Trypan blue mixture (10 μL) was loaded into COUNTESS® II cell counting chamber slides.

Flow Cytometry

About $1\times10^6$ total nuclei cells were blocked with 5 μL of human TruStain FcX™ in 95 μL of staining buffer (0.5% Bovine Serum Albumin (BSA)/DPBS)) at room temperature (RT) for 10 minutes. Cells were further incubated with Pacific blue-conjugated anti-human CD45 antibody (1:50), BV510-conjugated anti-human CD3 antibody (1:50), APC-Cy7-conjugated anti-human CD4 antibody (1:50), PE-Cy7-conjugated anti-human CD8 antibody (1:50), APC-conjugated anti-human CD19 antibody (1:50), FITC-conjugated anti-human CD56 antibody (1:50) and PE-conjugated anti-human CD33 antibody (1:50) at 4° C. for 30 minutes. Then, 1 mL of Ammonium-Chloride-Potassium (ACK) lysis buffer containing 5 μL 7-amino-actinomycin D (7-AAD) viability staining solution was applied to each sample. After incubation with ACK lysing buffer at RT for 10 minutes, cells were acquired with NovoCyte-3000 flow cytometer.

Results

White Blood Cells (WBCs) in Leukopak Samples

WBC in the tested leukopaks ranged from $8.14\times10^9$ to $21.36\times10^9$ cells with lymphocyte number ranging from $5.77\times10^9$ to $17.32\times10^9$.

CD4 and CD8 Enrichment—Purity, Viability, Cell Recovery, and Yield

Among the 9 batches tested, four were evaluated with program A and five were evaluated with program B. All batches yielded T cells with >90% purity and with >90% viability (Table 2). Cell recovery from program A was 31% whereas cell recovery from program B was 55.69%.

TABLE 2

CD4 and CD8 enrichment results

| Batch | Program | Leukopak CD3% | Non-Target Cell CD3% | Target Cell: Cell Number ($\times 10^9$) | Target Cell: CD3% | Target Cell: Viability (%) | Target Cell: Recovery (%) |
|---|---|---|---|---|---|---|---|
| 1 | A | 73.20 | 50.80 | 1.32 | 96.20 | 96.50 | 29.24 |
| 2 | | 72.30 | 60.40 | 2.76 | 96.30 | 93.50 | 27.00 |
| 3 | | 64.90 | 46.00 | 2.32 | 96.80 | 95.00 | 39.15 |
| 4 | | 63.50 | 55.00 | 2.59 | 89.70 | 94.00 | 30.77 |
| | Avg (A) | 68.48 | 53.05 | 2.25 | 94.75 | 94.75 | 31.54 |
| 5 | B | 70.30 | 15.70 | 6.00 | 94.50 | 93.00 | 39.75 |
| 6 | | 56.00 | 3.17 | 2.14 | 92.80 | 96.00 | 47.10 |
| 7 | | 69.00 | 16.80 | 4.68 | 96.60 | 93.00 | 49.10 |
| 8 | | 59.40 | 15.20 | 6.82 | 92.60 | 96.00 | 75.87 |
| 9 | | 55.50 | 11.20 | 3.88 | 93.60 | 98.00 | 61.65 |
| | Avg (B) | 62.04 | 12.41 | 4.70 | 94.02 | 95.20 | 54.69 |

Taken together, these results demonstrate that T cells from healthy donor (HD) leukopaks were enriched with high purity (>90%) and high viability (>90%) for CD4+ and $CD8^+$ T cells.

Example 2: Identification of Optimized Conditions for T Cell Activation

This Example reports identification of optimized conditions for T cell activation using a colloidal polymeric nanomatrix conjugated to recombinant humanized CD3 and CD28 agonists. Gene editing and/or CAR expression levels were examined on T cells activated at different conditions to identify the optimized T cell activation conditions that achieve superior gene editing and/or CAR expression levels. In brief, genetically engineered T cells were manufacturing in a small scale process in which enriched T cells were thawed and subsequently activated for 48 hours or 72 hours with one electroporation or two electroporations prior to activation, and % CAR$^+$ expression was determined 7 days post-transduction by flow cytometry.

To begin the small scale manufacturing process, cryovials were retrieved from liquid nitrogen storage and were thawed in a water bath until a small amount of frozen material remained. Cells were then added dropwise to a 10×volume of full growth medium (X-VIVO™ 15, 5% Human AB Serum, 50 ng/mL IL7 and 10 ng/mL IL2), and pelleted by centrifugation at 300 g for 10 minutes at room temperature. Cells were resuspended to a concentration of $1\times10^6$ cells/mL and subjected to colloidal polymeric nanomatrix conjugated to recombinant humanized CD3 and CD28 agonists-mediated activation, which improved downstream modification, or electroporated to introduce components for CRISPR-Cas9 dependent gene editing.

Isolated T cells were activated with recombinant CD3 and CD28 covalently attached to a colloidal polymeric nanomatrix. The colloidal polymeric nanomatrix conjugated to recombinant humanized CD3 and CD28 agonists was applied to cells at a 1:12.5 ratio or 40 μL per $1\times10^6$ cells in a nontreated flask. Cells were maintained with colloidal polymeric nanomatrix conjugated to recombinant humanized CD3 and CD28 agonists in an incubator at 37° C., 5% $CO_2$ for 48 hours or 72 hours. Following incubation, cells are centrifuged at 300 g for 10 minutes at room temperature. Cell pellets were then resuspended in full growth media and cultured overnight at a concentration of $1\times10^6$ cells/mL prior to gene modification.

For electroporation, total cell numbers and cell viability were quantified by addition of Trypan blue and counting on the COUNTESS® cytometer. Then, cells were centrifuged at 300 g for 10 minutes at room temperature. Cell pellets were washed in 10 mL of electroporation buffer and centrifuged again. While cells were being centrifuged, ribonucleoprotein (RNP) complexes were prepared. RNP complexes are formed separately and then combined together if performing multiple edits. Four separate RNP complexes were formed using gRNAs and Cas9 at the indicated concentrations (Table 3). Each RNP complex was formed with Cas9 comprising SEQ ID NO: 1. See also Example 5 for Cas9 and gRNA sequences.

TABLE 3

RNP Complexes Containing gRNA and Cas9.

| RNP Complex | Concentration of gRNA (μg/mL) | Sequence of gRNA | Concentration of Cas9 (μg/mL) |
|---|---|---|---|
| CD70 gRNA + Cas9 | 160 | G*C*U*UUGGUCCCAUUGGUCGCguuuu agagcuagaaauagcaaguuaaaauaag gcuaguccguuaucaacuugaaaaagug gcaccgagucggugcU*U*U*U (SEQ ID NO: 2) | 150-170 |
| TRAC gRNA + Cas9 | 80 | A*G*A*GCAACAGUGCUGUGGCCguuuu agagcuagaaauagcaaguuaaaauaag gcuaguccguuaucaacuugaaaaagug gcaccgagucggugcU*U*U*U (SEQ ID NO: 6) | 150 |
| β2M gRNA + Cas9 | 200 | G*C*U*ACUCUCUCUUUCUGGCCguuuu agagcuagaaauagcaaguuaaaauaag gcuaguccguuaucaacuugaaaaagug gcaccgagucggugcU*U*U*U (SEQ ID NO: 10) | 150 |
| PD1 gRNA + Cas9 | 160 | C*U*G*CAGCUUCUCCAACACAUguuuu agagcuagaaauagcaaguuaaaauaag gcuaguccguuaucaacuugaaaaagug gcaccgagucggugcU*U*U*U (SEQ ID NO: 66) | 170 |

Cells were electroporated using a transfection system based on flow electroporation. Once each individual cuvette was electroporated, the cell and RNP solution was aliquoted into a non-treated 12-well plate, with each well containing 500 μL of X-VIVO™ 15 media (without Human AB serum, IL2 or IL7). Cells were allowed to rest for 20 minutes in the incubator. Total cell numbers and cell viability were quantified by addition of Trypan blue and counting on the COUNTESS® cytometer.

Based on total cell numbers after resting, cells may need to be further diluted with X-VIVO™ 15 (without Human AB serum, IL2 or IL7) to reach the desired concentration. Total cell numbers are needed to calculate the volume of AAV needed to perform the transduction.

$$\mu L \text{ of AAV needed}=(\text{Total cell numbers})(\text{desired MOI (i.e., 20K)})/(\text{virus vgc/mL (i.e., } 1.5\times10^{13}))$$

AAV and cell suspension was mixed and allowed to incubate in a non-treated flask at 37° C. and 5% $CO_2$ for 1 hour. The entire volume, including AAV, was added to a static culture vessel containing 100 mL of full media. The static culture vessel was incubated for 3 days to allow cell expansion.

After electroporation, each well of a static culture vessel was filled with 100 mL of full growth media. Gene modified cells were seeded at a concentration of $5\times10^5$ cells/mL to $1\times10^6$ cells/mL in 100 mL of full growth media. The static culture vessel was incubated for three to four days to allow cell expansion. IL2 and IL7 were replenished every three to four days to a final working concentration of 100 U/mL or 10 ng/mL IL2 and 50 ng/mL IL7. Total cell numbers were quantified every three to four days by addition of Trypan blue and counting on the COUNTESS® cytometer. Cells were maintained in culture for nine to twelve days after electroporation to achieve maximal total cell numbers.

(i) Optimized Conditions for T Cell Activation Increased % CAR$^+$ Expression

Electroporation was used to introduce gRNA and Cas9 into T cells for CRISPR-Cas9 dependent gene editing of four target genes including CD70, PD1, β2M, and TRAC genes. A single electroporation was performed to target all four genes at once. When performing two electroporations, RNP complexes targeting CD70 and PD1 genes were introduced into T cells in a first electroporation and RNP complexes targeting β2M and TRAC genes in were introduced into those T cells in a second electroporation.

As shown in Table 4, T cells activated for 48 hours prior to one electroporation or two electroporations showed % CAR$^+$ expression of 54.7% and 57.5%, respectively. T cells activated for 72 hours exhibited approximately 10% more total % CAR$^+$ expression than T cells activated for 48 hours, regardless of whether T cells were electroporated once or twice (Table 4).

TABLE 4

% CAR$^+$ Expression of T cells Activated for 48 hours or 72 hours.

| Activation Condition (hours) | % CAR$^+$ Expression | |
|---|---|---|
| | 1 × Electroporation (CD70, PD1, β2M, TRAC) | 2 × Electroporation (1) CD70, PD1 (2) β2M, TRAC |
| 48 | 54.7% | 57.5% |
| 72 | 63.0% | 68.4% |

These results demonstrated that T cell activation for 72 hours increased % CAR$^+$ expression compared to that provided by 48 hours of T cell activation. Similar results were observed when RNP complex targeting PD1 was not included in the electroporation.

(ii) Optimized Conditions for T Cell Activation Attenuated Cell Loss from Electroporation The first electroporation step was performed on T cells to introduce components for CRISPR-Cas9 dependent editing of the CD70 gene and the PD1 gene. Cell numbers were determined before and after T cell activation for 48 hours or 72 hours.

As shown in Table 5, when T cells were activated for 48 hours, cell counts obtained prior to the second electroporation were less than the number of cells initially seeded for activation. By contrast, when T cells were activated for 72 hours, cell counts obtained prior to the second electroporation were greater than the number of cells initially seeded for activation (Table 5).

TABLE 5

Cell Number Before and After T Cell Activation for 48 hours or 72 hours.

| | Duration of T Cell Activation | |
|---|---|---|
| | 48 hours | 72 hours |
| Cell Number at Start of Activation | $16.8 \times 10^6$ | $16.8 \times 10^6$ |
| Cell Number at End of Activation | $10.7 \times 10^6$ | $36 \times 10^6$ |

These results demonstrated that T cell activation for 72 hours attenuated cell loss after the first electroporation that was observed when T cells were activated for only 48 hours. Similar results were observed when RNP complex targeting PD1 was not included in the electroporation.

Example 3: Identification of Optimized Conditions for Knockout of β2M

This Example reports identification of optimized conditions for knockout of (32M using CRISPR-Cas9 dependent gene editing. Knockout of (32M may be performed in either the first electroporation or the second electroporation. Knockout of TCR is generally performed in the second electroporation or prior to transduction to ensure HDR-mediated insertion of the CD70 CAR. Knockout of CD70 is generally performed in an initial electroporation to prevent possible cell-to-cell fratricide prior to insertion of the CD70 CAR.

In brief, genetically engineered T cells were manufacturing in a small scale process in which RNP complexes targeting (32M were formed, and introduced into T cells via a single electroporation or a two-step electroporation process. See Example 2 above for details.

For knockout of (32M in the first electroporation, RNP complexes targeting CD70 and β2M genes were introduced into T cells in a first electroporation, and RNP complexes targeting PD1 and TRAC genes were introduced into T cells in a second electroporation. For knockout of β2M in the second electroporation, RNP complexes targeting CD70 and PD1 genes were introduced into T cells in a first electroporation, and RNP complexes targeting β2M and TRAC genes were introduced into T cells a second electroporation. T cells were also electroporated in a single electroporation event with RNP complexes targeting CD70, PD1, β2M and TRAC genes.

As shown in Table 6, when a RNP complex targeting β2M was included in the first electroporation, residual β2M$^+$ expression was about 60% at 7 days post-transduction, regardless of whether T cells were activated for 48 hours or 72 hours. Residual β2M$^+$ expression was about 20% when the RNP complex targeting β2M was included in a single electroporation or in the second electroporation (Table 6). Residual CD70$^+$ expression was undetectable at 7 days post-transduction (Table 7). Residual CD70$^+$ expressing cells may have been eliminated by knockout with a RNP complex targeting CD70 or eliminated by CD70 CAR$^+$ cells. Similar T cell growth and T cell viability was observed for each of the β2M knockout conditions tested (FIG. 1).

TABLE 6

Effect of β2M Knockout Conditions on β2M Expression.

| Activation Condition (hours) | β2M$^+$ Expression | | |
|---|---|---|---|
| | 1 × Electroporation (CD70, PD1, β2M, TRAC) | 2 × Electroporation (1) CD70, PD1 (2) β2M, TRAC | 2 × Electroporation (1) CD70, β2M (2) PD1, TRAC |
| 48 | 26.0% | 19.5% | 64.2% |
| 72 | 27.8% | 21.6% | 64.7% |

TABLE 7

Effect of β2M Knockout Conditions on CD70 Expression.

| Activation Condition (hours) | CD70$^+$ Expression | | |
|---|---|---|---|
| | 1 × Electroporation (CD70, PD1, β2M, TRAC) | 2 × Electroporation (1) CD70, PD1 (2) β2M, TRAC | 2 × Electroporation (1) CD70, β2M (2) PD1, TRAC |
| 48 | 0.29% | 0.41% | 0.30% |
| 72 | 0.19% | 0.43% | 0.26% |

These results demonstrated that introducing a RNP complex targeting β2M in the second electroporation step provided superior knockout of β2M while maintaining efficient knockout of CD70, or cell growth and cell viability. Similar results were observed when RNP complex targeting PD1 was not included in the electroporation.

Example 4: Identification of Optimized Conditions for T Cell Electroporation This Example reports identification of optimized conditions for introducing multiple RNP complexes for CRISPR-Cas9 dependent gene editing into T cells via electroporation.

In brief, genetically engineered T cells were manufacturing in a small scale process in which RNP complexes were introduced into T cells via a single electroporation or a two-step electroporation process. See Example 2 above for details. Translocation rates were determined by ddPCR.

T cells genetically engineered with one electroporation showed significantly higher translocation rates than those electroporated in two steps, except when RNP complexes targeting PD1 and CD70 were combined together in the first electroporation (FIG. 2A). Translocation rates were less than 2% when the gRNA targeting CD70 was delivered in the first electroporation (via an RNP complex). See FIGS. 2A and 2B. Cytogenetic analysis of T cells electroporated with the four RNP complexes together revealed that translocations likely occurred in chromosomes that house PD1 (chromosome 2), β2M (chromosome 15), TCR (chromosome 14), and CD70 (chromosome 19) (data not shown).

Taken together, these results demonstrated that lower translocation rates may be achieved by introducing RNP complexes via electroporation performed in two steps. Similar results were observed when RNP complex targeting PD1 was not included in the electroporation.

Example 5: Manufacturing Process Development for Making Genetically Engineered T Cells Expressing an Anti-CD70 CAR and Having Genetically Disrupted CD70, TRAC and β2M Genes (CTX130)

Overview

CTX130 is a CD70-directed T cell immunotherapy comprised of allogeneic T cells that are genetically modified ex vivo using CRISPR/Cas9 (Clustered Regularly Interspaced Short Palindromic Repeats/CRISPR associated protein 9) gene editing components (sgRNA and Cas9 nuclease).

The modifications include targeted disruption of T cell receptor alpha constant (TRAC), β2M, and CD70. The disruption of the TRAC locus results in loss of expression of the T cell receptor (TCR) and is intended to reduce the probability of Graft versus Host Disease (GvHD), while the disruption of the β2M locus results in lack of expression of the major histocompatibility complex type I (MHC I) proteins and is intended to improve persistence by reducing the probability of host rejection. The disruption of CD70 results in loss of expression of CD70, which prevents possible cell-to-cell fratricide prior to insertion of the CD70 CAR. The addition of the anti-CD70 CAR directs the modified T cells towards CD70-expressing tumor cells.

The anti-CD70 CAR is composed of an anti-CD70 single-chain variable fragment (scFv) specific for CD70, followed by a CD8 hinge and transmembrane domain that is fused to an intracellular co-signaling domain of 4-1 BB and a CD3 signaling domain.

An exemplary manufacturing process for CTX130 is depicted in FIG. 3A.

Evolution of Manufacturing Process

Based on the conditions determined by the optimized processes described in Examples 1-4, the CTX130 manufacturing process was performed at three production scales including research scale, development scale, and clinical scale. The Research Scale Process was performed at small scale, and the Research Scale Process was scaled up and transferred for Development Scale Process and Clinical Scale Process. Initial campaigns (4 lots) were conducted using laboratory-grade starting materials for the drug substance for feasibility and adjustment of the operating parameters. Subsequently, use of GMP-sourced starting materials (sgRNAs, Cas9 and rAAV-145b) and quantitative acceptance criteria were implemented for the Clinical Scale Process, which is operationally identical to the Development Scale Process.

Selection of the Starting Materials

The starting materials for production of CTX130 include:
- leukopaks collected from healthy donors,
- bacterially-derived Cas9 nuclease,
- three single guide RNAs (sgRNA), CD70-7 sgRNA which targets the CD70 locus, TA-1 which targets the TRAC locus, and β2M-1 which targets the β2M locus, and
- the recombinant AAV-6 vector (rAAV-145b), which encodes the anti-CD70 CAR gene.

Structure information for the components used in making the genetic modifications of CTX110, as well as edited TRAC and β2M gene loci, is provided below:

```
Amino acid sequence of Cas9 nuclease
(SEQ ID NO: 1):
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK
```

-continued

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

-continued

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

TABLE 8 sgRNA Sequences and Target Gene Sequences.

| | | | SEQ ID NO: |
|---|---|---|---|
| **sgRNA Sequences** | | | |
| CD70 sgRNA (CD70-7) | Modified | G*C*U*UUGGUCCCAUUGGUCGCguuuuagagcuagaaauagcaaguuaaaauaaggcuaguccguuaucaacuugaaaaaguggcaccgagucggugcU*U*U*U | 2 |
| | Unmodified | GCUUUGGUCCCAUUGGUCGCguuuuagagcuagaaauagcaaguuaaaauaaggcuaguccguuaucaacuugaaaaaguggcaccgagucggugcUUUU | 3 |
| CD70 sgRNA spacer | Modified | G*C*U*UUGGUCCCAUUGGUCGC | 4 |
| | Unmodified | GCUUUGGUCCCAUUGGUCGC | 5 |
| TRAC sgRNA (TA-1) | Modified | A*G*A*GCAACAGUGCUGUGGCCguuuuagagcuagaaauagcaaguuaaaauaaggcuaguccguuaucaacuugaaaaaguggcaccgagucggugcU*U*U*U | 6 |
| | Unmodified | AGAGCAACAGUGCUGUGGCCguuuuagagcuagaaauagcaaguuaaaauaaggcuaguccguuaucaacuugaaaaaguggcaccgagucggugcUUUU | 7 |
| TRAC sgRNA spacer | Modified | A*G*A*GCAACAGUGCUGUGGCC | 8 |
| | Unmodified | AGAGCAACAGUGCUGUGGCC | 9 |
| β2M sgRNA (β2M-1) | Modified | G*C*U*ACUCUCUCUUUCUGGCCguuuuagagcuagaaauagcaaguuaaaauaaggcuaguccguuaucaacuugaaaaaguggcaccgagucggugcU*U*U*U | 10 |
| | Unmodified | GCUACUCUCUCUUUCUGGCCguuuuagagcuagaaauagcaaguuaaaauaaggcuaguccguuaucaacuugaaaaaguggcaccgagucggugcUUUU | 11 |
| β2M sgRNA spacer | Modified | G*C*U*ACUCUCUCUUUCUGGCC | 12 |
| | Unmodified | GCUACUCUCUCUUUCUGGCC | 13 |
| **Target Sequences (PAM)** | | | |
| CD70 sgRNA | GCTTTGGTCCCATTGGTCGC (GGG) | | 14 |
| CD70 sgRNA | GCTTTGGTCCCATTGGTCGC | | 15 |
| TRAC sgRNA | AGAGCAACAGTGCTGTGGCC (TGG) | | 16 |
| TRAC sgRNA | AGAGCAACAGTGCTGTGGCC | | 17 |
| β2M sgRNA | GCTACTCTCTCTTTCTGGCC (TGG) | | 18 |
| β2M sgRNA | GCTACTCTCTCTTTCTGGCC | | 19 |
| **Exemplary sgRNA Formulas** | | | |
| sgRNA sequence | Nnnnnnnnnnnnnnnnnnnnguuuuagagcuagaaauagcaaguuaaaauaaggcuaguccguuaucaacuugaaaaaguggcaccgagucggugcuuuu | | 20 |
| sgRNA sequence | Nnnnnnnnnnnnnnnnnnnnguuuuagagcuagaaauagcaaguuaaaauaaggcuaguccguuaucaacuugaaaaaguggcaccgagucggugc | | 21 |

TABLE 8-continued

| sgRNA Sequences and Target Gene Sequences. | | SEQ ID NO: |
|---|---|---|
| sgRNA sequence | $n_{(17-30)}$guuuuagagcuagaaauagcaaguuaaaauaaggcuaguccguuauca acuugaaaaaguggcaccgagucggugcu$_{(1-8)}$ | 22 |

*indicates a nucleotide with a 2'-O-methyl phosphorothioate modification.
"n" refers to the spacer sequence at the 5' end.

TABLE 9

Edited TRAC Gene Sequence.

| Description | Sequence (Deletions indicated by dashes (-); insertions indicated by bold) | SEQ ID NO: |
|---|---|---|
| TRAC gene edit | AA---------------------GAGCAACAAATCTGACT | 23 |
| TRAC gene edit | AAGAGCAACAGTGCTGT-GCCTGGAGCAACAAATCTGACT | 24 |
| TRAC gene edit | AAGAGCAACAGTG-------CTGGAGCAACAAATCTGACT | 25 |
| TRAC gene edit | AAGAGCAACAGT------GCCTGGAGCAACAAATCTGACT | 26 |
| TRAC gene edit | AAGAGCAACAGTG---------------------CTGACT | 27 |
| TRAC gene edit | AAGAGCAACAGTGCTGT**G**GGCCTGGAGCAACAAATCTGACT | 28 |
| TRAC gene edit | AAGAGCAACAGTGC--TGGCCTGGAGCAACAAATCTGACT | 29 |
| TRAC gene edit | AAGAGCAACAGTGCTGT**T**GCCTGGAGCAACAAATCTGACT | 30 |

TABLE 10

Edited β2M Gene Sequence.

| Description | Sequence (Deletions indicated by dashes (-); insertions indicated by bold) | SEQ ID NO: |
|---|---|---|
| β2M gene-edit | CGTGGCCTTAGCTGTGCTCGCGCTACTCTCTCTTTCT- GCCTGGAGGCTATCCAGCGTGAGTCTCTCCTACCCTCCCGCT | 31 |
| β2M gene-edit | CGTGGCCTTAGCTGTGCTCGCGCTACTCTCTCTTTC-- GCCTGGAGGCTATCCAGCGTGAGTCTCTCCTACCCTCCCGCT | 32 |
| β2M gene-edit | CGTGGCCTTAGCTGTGCTCGCGCTACTCTCTCTTT----- CTGGAGGCTATCCAGCGTGAGTCTCTCCTACCCTCCCGCT | 33 |
| β2M gene-edit | CGTGGCCTTAGCTGTGCTCGCGCTACTCTCTCTTTCTG**GATA**GCCTGGAGGC TATCCAGCGTGAGTCTCTCCTACCCTCCCGCT | 34 |
| β2M gene-edit | CGTGGCCTTAGCTGTGCTCGC------------------------- GCTATCCAGCGTGAGTCTCTCCTACCCTCCCGCT | 35 |
| β2M gene-edit | CGTGGCCTTAGCTGTGCTCGCGCTACTCTCTCTTTC**TG**TGGCCTGGAGGCTA TCCAGCGTGAGTCTCTCCTACCCTCCCGCT | 36 |

TABLE 11

Edited CD70 Gene Sequence.

| Description | Sequence (Deletions indicated by dashes (-); insertions indicated by bold) | SEQ ID NO: |
|---|---|---|
| CD70 gene-edit | CACACCACGAGGCAGATCACCAAGCCCGCG--CAATGGGACCAAAGCAGCCCGCAGGACG | 37 |
| CD70 gene-edit | CACACCACGAGGCAGATCACCAAGCCCGCG**A**ACCAATGGGACCAAAGCAGCCCGCAGGACG | 38 |
| CD70 gene-edit | CACACCACGAGGCAGATC------------ACCAATGGGACCAAAGCAGCCCGCAGGACG | 39 |
| CD70 gene-edit | CACACCACGAGGCAGATCACCAAGCCCGCG-CCAATGGGACCAAAGCAGCCCGCAGGACG | 40 |
| CD70 gene-edit | CACACCACGAGGCAGATCACCAAGCCCGC-ACCAATGGGACCAAAGCAGCCCGCAGGACG | 41 |
| CD70 gene-edit | CACACCACGAGGCAGATCACCA-------------------------AGCCCGCAGGACG | 42 |

TABLE 12

Sequences of Anti-CD70 CAR Construct Components.

| Description | Sequence | SEQ ID NO: |
|---|---|---|
| CD70 rAAV (CD70B scFV with 41BB) | CCTGCAGGCAGCTGCGCGCTCGCTCGCTCACTGAGGCCGCCCGGGCGTCGG<br>GCGACCTTTGGTCGCCCGGCCTCAGTGAGCGAGCGAGCGCGCAGAGAGGGA<br>GTGGCCAACTCCATCACTAGGGGTTCCTGCGGCCGCACGCGTGAGATGTAA<br>GGAGCTGCTGTGACTTGCTCAAGGCCTTATATCGAGTAAACGGTAGTGCTG<br>GGGCTTAGACGCAGGTGTTCTGATTTATAGTTCAAAACCTCTATCAATGAG<br>AGAGCAATCTCCTGGTAATGTGATAGATTTCCCAACTTAATGCCAACATAC<br>CATAAACCTCCCATTCTGCTAATGCCCAGCCTAAGTTGGGGAGACCACTCC<br>AGATTCCAAGATGTACAGTTTGCTTTGCTGGGCCTTTTTCCCATGCCTGCC<br>TTTACTCTGCCAGAGTTATATTGCTGGGGTTTTGAAGAAGATCCTATTAAA<br>TAAAAGAATAAGCAGTATTATTAAGTAGCCCTGCATTTCAGGTTTCCTTGA<br>GTGGCAGGCCAGGCCTGGCCGTGAACGTTCACTGAAATCATGGCCTCTTGG<br>CCAAGATTGATAGCTTGTGCCTGTCCCTGAGTCCCAGTCCATCACGAGCAG<br>CTGGTTTCTAAGATGCTATTTCCCGTATAAAGCATGAGACCGTGACTTGCC<br>AGCCCCACAGAGCCCCGCCCTTGTCCATCACTGGCATCTGGACTCCAGCCT<br>GGGTTGGGGCAAAGAGGGAAATGAGATCATGTCCTAACCCTGATCCTCTTG<br>TCCCACAGATATCCAGAACCCTGACCCTGCCGTGTACCAGCTGAGAGACTC<br>TAAATCCAGTGACAAGTCTGTCTGCCTATTCACCGATTTTGATTCTCAAAC<br>AAATGTGTCACAAAGTAAGGATTCTGATGTGTATATCACAGACAAAACTGT<br>GCTAGACATGAGGTCTATGGACTTCAGGCTCCGGTGCCCGTCAGTGGGCAG<br>AGCGCACATCGCCCACAGTCCCCGAGAAGTTGGGGGGAGGGGTCGGCAATT<br>GAACCGGTGCCTAGAGAAGGTGGCGCGGGGTAAACTGGGAAAGTGATGTCG<br>TGTACTGGCTCCGCCTTTTTCCCGAGGGTGGGGGAGAACCGTATATAAGTG<br>CAGTAGTCGCCGTGAACGTTCTTTTTCGCAACGGGTTTGCCGCCAGAACAC<br>AGGTAAGTGCCGTGTGTGGTTCCCGCGGGCCTGGCCTCTTTACGGGTTATG<br>GCCCTTGCGTGCCTTGAATTACTTCCACTGGCTGCAGTACGTGATTCTTGA<br>TCCCGAGCTTCGGGTTGGAAGTGGGTGGGAGAGTTCGAGGCCTTGCGCTTA<br>AGGAGCCCCTTCGCCTCGTGCTTGAGTTGAGGCCTGGCCTGGGCGCTGGGG<br>CCGCCGCGTGCGAATCTGGTGGCACCTTCGCGCCTGTCTCGCTGCTTTCGA<br>TAAGTCTCTAGCCATTTAAAATTTTTGATGACCTGCTGCGACGCTTTTTTT<br>CTGGCAAGATAGTCTTGTAAATGCGGGCCAAGATCTGCACACTGGTATTTC<br>GGTTTTTGGGGCCGCGGGCGGCGACGGGGCCCGTGCGTCCCAGCGCACATG<br>TTCGGCGAGGCGGGGCCTGCGAGCGCGGCCACCGAGAATCGGACGGGGGTA<br>GTCTCAAGCTGGCCGGCCTGCTCTGGTGCCTGGCCTCGCGCCGCCGTGTAT<br>CGCCCCGCCCTGGGCGGCAAGGCTGGCCCGGTCGGCACCAGTTGCGTGAGC<br>GGAAAGATGGCCGCTTCCCGGCCCTGCTGCAGGGAGCTCAAAATGGAGGAC<br>GCGGCGCTCGGGAGAGCGGGCGGGTGAGTCACCCACACAAAGGAAAAGGGC<br>CTTTCCGTCCTCAGCCGTCGCTTCATGTGACTCCACGGAGTACCGGGCGCC<br>GTCCAGGCACCTCGATTAGTTCTCGAGCTTTTGGAGTACGTCGTCTTTAGG<br>TTGGGGGGAGGGGTTTTATGCGATGGAGTTTCCCCACACTGAGTGGGTGGA<br>GACTGAAGTTAGGCCAGCTTGGCACTTGATGTAATTCTCCTTGGAATTTGC<br>CCTTTTTGAGTTTGGATCTTGGTTCATTCTCAAGCCTCAGACAGTGGTTCA<br>AAGTTTTTTTCTTCCATTTCAGGTGTCGTGACCACCATGGCGCTTCCGGTG<br>ACAGCACTGCTCCTCCCCTTGGCGCTGTTGCTCCACGCAGCAAGGCCGCAG<br>GTCCAGTTGGTGCAAAGCGGGGCGGAGGTGAAAAAACCCGGCGCTTCCGTG<br>AAGGTGTCCTGTAAGGCGTCCGGTTATACGTTCACGAACTACGGGATGAAT<br>TGGGTTCGCCAAGCGCCGGGGCAGGGACTGAAATGGATGGGGTGGATAAAT<br>ACCTACACCGGCGAACCTACATACGCCGACGCTTTTAAAGGGCGAGTCACT<br>ATGACGCGCGATACCAGCATATCCACCGCATACATGGAGCTGTCCCGACTC<br>CGGTCAGACGACACGGCTGTCTACTATTGTGCTCGGGACTATGGCGATTAT<br>GGCATGGACTACTGGGGTCAGGGTACGACTGTAACAGTTAGTAGTGGTGGA<br>GGCGGCAGTGGCGGGGGGGGAAGCGGAGGAGGGGGTTCTGGTGACATAGTT<br>ATGACCCAATCCCCAGATAGTTTGGCGGTTTCTCTGGGCGAGAGGGCAACG<br>ATTAATTGTCGCGCATCAAAGAGCGTTTCAACGAGCGGATATTCTTTTATG<br>CATTGGTACCAGCAAAAACCCGGACAACCGCCGAAGCTGCTGATCTACTTG<br>GCTTCAAATCTTGAGTCTGGGGTGCCGGACCGATTTTCTGGTAGTGGAAGC | 43 |

TABLE 12-continued

Sequences of Anti-CD70 CAR Construct Components.

| Description | Sequence | SEQ ID NO: |
|---|---|---|
| | GGAACTGACTTTACGCTCACGATCAGTTCACTGCAGGCTGAGGATGTAGCG<br>GTCTATTATTGCCAGCACAGTAGAGAAGTCCCCTGGACCTTCGGTCAAGGC<br>ACGAAAGTAGAAATTAAAAGTGCTGCTGCCTTTGTCCCGGTATTTCTCCCA<br>GCCAAACCGACCACGACTCCCGCCCCGCGCCCTCCGACACCCGCTCCCACC<br>ATCGCCTCTCAACCTCTTAGTCTTCGCCCCGAGGCATGCCGACCCGCCGCC<br>GGGGGTGCTGTTCATACGAGGGGCTTGGACTTCGCTTGTGATATTTACATT<br>TGGGCTCCGTTGGCGGGTACGTGCGGCGTCCTTTTGTTGTCACTCGTTATT<br>ACTTTGTATTGTAATCACAGGAATCGCAAACGGGGCAGAAAGAAACTCCTG<br>TATATATTCAAACAACCATTTATGAGACCAGTACAAACTACTCAAGAGGAA<br>GATGGCTGTAGCTGCCGATTTCCAGAAGAAGAAGAAGGAGGATGTGAACTG<br>CGAGTGAAGTTTTCCCGAAGCGCAGACGCTCCGGCATATCAGCAAGGACAG<br>AATCAGCTGTATAACGAACTGAATTTGGGACGCCGCGAGGAGTATGACGTG<br>CTTGATAAACGCCGGGGGAGAGACCCGGAAATGGGGGGTAAACCCCGAAGA<br>AAGAATCCCCAAGAAGGACTCTACAATGAACTCCAGAAGGATAAGATGGCG<br>GAGGCCTACTCAGAAATAGGTATGAAGGGCGAACGACGACGGGGAAAAGGT<br>CACGATGGCCTCTACCAAGGGTTGAGTACGGCAACCAAAGATACGTACGAT<br>GCACTGCATATGCAGGCCCTGCCTCCCAGATAATAATAAAATCGCTATCCA<br>TCGAAGATGGATGTGTGTTGGTTTTTTGTGTGTGGAGCAACAAATCTGACT<br>TTGCATGTGCAAACGCCTTCAACAACAGCATTATTCCAGAAGACACCTTCT<br>TCCCCAGCCCAGGTAAGGGCAGCTTTGGTGCCTTCGCAGGCTGTTTCCTTG<br>CTTCAGGAATGGCCAGGTTCTGCCCAGAGCTCTGGTCAATGATGTCTAAAA<br>CTCCTCTGATTGGTGGTCTCGGCCTTATCCATTGCCACCAAAACCCTCTTT<br>TTACTAAGAAACAGTGAGCCTTGTTCTGGCAGTCCAGAGAATGACACGGGA<br>AAAAAGCAGATGAAGAGAAGGTGGCAGGAGAGGGCACGTGGCCCAGCCTCA<br>GTCTCTCCAACTGAGTTCCTGCCTGCCTGCCTTTGCTCAGACTGTTTGCCC<br>CTTACTGCTCTTCTAGGCCTCATTCTAAGCCCCTTCTCCAAGTTGCCTCTC<br>CTTATTTCTCCCTGTCTGCCAAAAAATCTTTCCCAGCTCACTAAGTCAGTC<br>TCACGCAGTCACTCATTAACCCACCAATCACTGATTGTGCCGGCACATGAA<br>TGCACCAGGTGTTGAAGTGGAGGAATTAAAAAGTCAGATGAGGGGTGTGCC<br>CAGAGGAAGCACCATTCTAGTTGGGGGAGCCCATCTGTCAGCTGGGAAAAG<br>TCCAAATAACTTCAGATTGGAATGTGTTTTAACTCAGGGTTGAGAAAACAG<br>CTACCTTCAGGACAAAAGTCAGGGAAGGGCTCTCTGAAGAAATGCTACTTG<br>AAGATACCAGCCCTACCAAGGGCAGGGAGAGGACCCTATAGAGGCCTGGGA<br>CAGGAGCTCAATGAGAAAGGTAACCACGTGCGGACCGAGGCTGCAGCGTCG<br>TCCTCCCTAGGAACCCCTAGTGATGGAGTTGGCCACTCCCTCTCTGCGCGC<br>TCGCTCGCTCACTGAGGCCGGGCGACCAAAGGTCGCCCGACGCCCGGGCTT<br>TGCCCGGGCGGCCTCAGTGAGCGAGCGAGCGCGCAGCTGCCTGCAGG | |
| CD70<br>LHA to RHA<br>(CD70B scFV<br>with 41BB) | GAGATGTAAGGAGCTGCTGTGACTTGCTCAAGGCCTTATATCGAGTAAACG<br>GTAGTGCTGGGGCTTAGACGCAGGTGTTCTGATTTATAGTTCAAAACCTCT<br>ATCAATGAGAGAGCAATCTCCTGGTAATGTGATAGATTTCCCAACTTAATG<br>CCAACATACCATAAACCTCCCATTCTGCTAATGCCCAGCCTAAGTTGGGGA<br>GACCACTCCAGATTCCAAGATGTACAGTTTGCTTTGCTGGGCCTTTTTCCC<br>ATGCCTGCCTTTACTCTGCCAGAGTTATATTGCTGGGGTTTTGAAGAAGAT<br>CCTATTAAATAAAAGAATAAGCAGTATTATTAAGTAGCCCTGCATTTCAGG<br>TTTCCTTGAGTGGCAGGCCAGGCCTGGCCGTGAACGTTCACTGAAATCATG<br>GCCTCTTGGCCAAGATTGATAGCTTGTGCCTGTCCCTGAGTCCCAGTCCAT<br>CACGAGCAGCTGGTTTCTAAGATGCTATTTCCCGTATAAAGCATGAGACCG<br>TGACTTGCCAGCCCCACAGAGCCCCGCCCTTGTCCATCACTGGCATCTGGA<br>CTCCAGCCTGGGTTGGGGCAAAGAGGGAAATGAGATCATGTCCTAACCCTG<br>ATCCTCTTGTCCCACAGATATCCAGAACCCTGACCCTGCCGTGTACCAGCT<br>GAGAGACTCTAAATCCAGTGACAAGTCTGTCTGCCTATTCACCGATTTTGA<br>TTCTCAAACAAATGTGTCACAAAGTAAGGATTCTGATGTGTATATCACAGA<br>CAAAACTGTGCTAGACATGAGGTCTATGGACTTCAGGCTCCGGTGCCCGTC<br>AGTGGGCAGAGCGCACATCGCCCACAGTCCCCGAGAAGTTGGGGGGAGGGG<br>TCGGCAATTGAACCGGTGCCTAGAGAAGGTGGCGCGGGGTAAACTGGGAAA<br>GTGATGTCGTGTACTGGCTCCGCCTTTTTCCCGAGGGTGGGGGAGAACCGT<br>ATATAAGTGCAGTAGTCGCCGTGAACGTTCTTTTTCGCAACGGGTTTGCCG<br>CCAGAACACAGGTAAGTGCCGTGTGTGGTTCCCGCGGGCCTGGCCTCTTTA<br>CGGGTTATGGCCCTTGCGTGCCTTGAATTACTTCCACTGGCTGCAGTACGT<br>GATTCTTGATCCCGAGCTTCGGGTTGGAAGTGGGTGGGAGAGTTCGAGGCC<br>TTGCGCTTAAGGAGCCCCTTCGCCTCGTGCTTGAGTTGAGGCCTGGCCTGG<br>GCGCTGGGGCCGCCGCGTGCGAATCTGGTGGCACCTTCGCGCCTGTCTCGC<br>TGCTTTCGATAAGTCTCTAGCCATTTAAAATTTTTGATGACCTGCTGCGAC<br>GCTTTTTTTCTGGCAAGATAGTCTTGTAAATGCGGGCCAAGATCTGCACAC<br>TGGTATTTCGGTTTTTGGGGCCGCGGGCGGCGACGGGGCCCGTGCGTCCCA<br>GCGCACATGTTCGGCGAGGCGGGGCCTGCGAGCGCGGCCACCGAGAATCGG<br>ACGGGGGTAGTCTCAAGCTGGCCGGCCTGCTCTGGTGCCTGGCCTCGCGCC<br>GCCGTGTATCGCCCCGCCCTGGGCGGCAAGGCTGGCCCGGTCGGCACCAGT<br>TGCGTGAGCGGAAAGATGGCCGCTTCCCGGCCCTGCTGCAGGGAGCTCAAA<br>ATGGAGGACGCGGCGCTCGGGAGAGCGGGCGGGTGAGTCACCCACACAAAG<br>GAAAAGGGCCTTTCCGTCCTCAGCCGTCGCTTCATGTGACTCCACGGAGTA<br>CCGGGCGCCGTCCAGGCACCTCGATTAGTTCTCGAGCTTTTGGAGTACGTC<br>GTCTTTAGGTTGGGGGGAGGGGTTTTATGCGATGGAGTTTCCCCACACTGA<br>GTGGGTGGAGACTGAAGTTAGGCCAGCTTGGCACTTGATGTAATTCTCCTT | 44 |

TABLE 12-continued

Sequences of Anti-CD70 CAR Construct Components.

| Description | Sequence | SEQ ID NO: |
|---|---|---|
| | GGAATTTGCCCTTTTTGAGTTTGGATCTTGGTTCATTCTCAAGCCTCAGAC<br>AGTGGTTCAAAGTTTTTTTCTTCCATTTCAGGTGTCGTGACCACCATGGCG<br>CTTCCGGTGACAGCACTGCTCCTCCCCTTGGCGCTGTTGCTCCACGCAGCA<br>AGGCCGCAGGTCCAGTTGGTGCAAAGCGGGGCGGAGGTGAAAAAACCCGGC<br>GCTTCCGTGAAGGTGTCCTGTAAGGCGTCCGGTTATACGTTCACGAACTAC<br>GGGATGAATTGGGTTCGCCAAGCGCCGGGGCAGGGACTGAAATGGATGGGG<br>TGGATAAATACCTACACCGGCGAACCTACATACGCCGACGCTTTTAAAGGG<br>CGAGTCACTATGACGCGCGATACCAGCATATCCACCGCATACATGGAGCTG<br>TCCCGACTCCGGTCAGACGACACGGCTGTCTACTATTGTGCTCGGGACTAT<br>GGCGATTATGGCATGGACTACTGGGGTCAGGGTACGACTGTAACAGTTAGT<br>AGTGGTGGAGGCGGCAGTGGCGGGGGGGGAAGCGGAGGAGGGGGTTCTGGT<br>GACATAGTTATGACCCAATCCCCAGATAGTTTGGCGGTTTCTCTGGGCGAG<br>AGGGCAACGATTAATTGTCGCGCATCAAAGAGCGTTTCAACGAGCGGATAT<br>TCTTTTATGCATTGGTACCAGCAAAAACCCGGACAACCGCCGAAGCTGCTG<br>ATCTACTTGGCTTCAAATCTTGAGTCTGGGGTGCCGGACCGATTTTCTGGT<br>AGTGGAAGCGGAACTGACTTTACGCTCACGATCAGTTCACTGCAGGCTGAG<br>GATGTAGCGGTCTATTATTGCCAGCACAGTAGAGAAGTCCCCTGGACCTTC<br>GGTCAAGGCACGAAAGTAGAAATTAAAAGTGCTGCTGCCTTTGTCCCGGTA<br>TTTCTCCCAGCCAAACCGACCACGACTCCCGCCCCGCGCCCTCCGACACCC<br>GCTCCCACCATCGCCTCTCAACCTCTTAGTCTTCGCCCCGAGGCATGCCGA<br>CCCGCCGCCGGGGGTGCTGTTCATACGAGGGGCTTGGACTTCGCTTGTGAT<br>ATTTACATTTGGGCTCCGTTGGCGGGTACGTGCGGCGTCCTTTTGTTGTCA<br>CTCGTTATTACTTTGTATTGTAATCACAGGAATCGCAAACGGGGCAGAAAG<br>AAACTCCTGTATATATTCAAACAACCATTTATGAGACCAGTACAAACTACT<br>CAAGAGGAAGATGGCTGTAGCTGCCGATTTCCAGAAGAAGAAGAAGGAGGA<br>TGTGAACTGCGAGTGAAGTTTTCCCGAAGCGCAGACGCTCCGGCATATCAG<br>CAAGGACAGAATCAGCTGTATAACGAACTGAATTTGGGACGCCGCGAGGAG<br>TATGACGTGCTTGATAAACGCCGGGGGAGAGACCCGGAAATGGGGGGTAAA<br>CCCCGAAGAAAGAATCCCCAAGAAGGACTCTACAATGAACTCCAGAAGGAT<br>AAGATGGCGGAGGCCTACTCAGAAATAGGTATGAAGGGCGAACGACGACGG<br>GGAAAAGGTCACGATGGCCTCTACCAAGGGTTGAGTACGGCAACCAAAGAT<br>ACGTACGATGCACTGCATATGCAGGCCCTGCCTCCCAGATAATAATAAAAT<br>CGCTATCCATCGAAGATGGATGTGTGTTGGTTTTTTGTGTGTGGAGCAACA<br>AATCTGACTTTGCATGTGCAAACGCCTTCAACAACAGCATTATTCCAGAAG<br>ACACCTTCTTCCCCAGCCCAGGTAAGGGCAGCTTTGGTGCCTTCGCAGGCT<br>GTTTCCTTGCTTCAGGAATGGCCAGGTTCTGCCCAGAGCTCTGGTCAATGA<br>TGTCTAAAACTCCTCTGATTGGTGGTCTCGGCCTTATCCATTGCCACCAAA<br>ACCCTCTTTTTACTAAGAAACAGTGAGCCTTGTTCTGGCAGTCCAGAGAAT<br>GACACGGGAAAAAAGCAGATGAAGAGAAGGTGGCAGGAGAGGGCACGTGGC<br>CCAGCCTCAGTCTCTCCAACTGAGTTCCTGCCTGCCTGCCTTTGCTCAGAC<br>TGTTTGCCCCTTACTGCTCTTCTAGGCCTCATTCTAAGCCCCTTCTCCAAG<br>TTGCCTCTCCTTATTTCTCCCTGTCTGCCAAAAAATCTTTCCCAGCTCACT<br>AAGTCAGTCTCACGCAGTCACTCATTAACCCACCAATCACTGATTGTGCCG<br>GCACATGAATGCACCAGGTGTTGAAGTGGAGGAATTAAAAAGTCAGATGAG<br>GGGTGTGCCCAGAGGAAGCACCATTCTAGTTGGGGGAGCCCATCTGTCAGC<br>TGGGAAAAGTCCAAATAACTTCAGATTGGAATGTGTTTTAACTCAGGGTTG<br>AGAAAACAGCTACCTTCAGGACAAAAGTCAGGGAAGGGCTCTCTGAAGAAA<br>TGCTACTTGAAGATACCAGCCCTACCAAGGGCAGGGAGAGGACCCTATAGA<br>GGCCTGGGACAGGAGCTCAATGAGAAAGG | |
| CD70 CAR nucleotide sequence (CD70B scFV with 41BB) | ATGGCGCTTCCGGTGACAGCACTGCTCCTCCCCTTGGCGCTGTTGCTCCACG<br>CAGCAAGGCCGCAGGTCCAGTTGGTGCAAAGCGGGGCGGAGGTGAAAAAACC<br>CGGCGCTTCCGTGAAGGTGTCCTGTAAGGCGTCCGGTTATACGTTCACGAAC<br>TACGGGATGAATTGGGTTCGCCAAGCGCCGGGGCAGGGACTGAAATGGATGG<br>GGTGGATAAATACCTACACCGGCGAACCTACATACGCCGACGCTTTTAAAGG<br>GCGAGTCACTATGACGCGCGATACCAGCATATCCACCGCATACATGGAGCTG<br>TCCCGACTCCGGTCAGACGACACGGCTGTCTACTATTGTGCTCGGGACTATG<br>GCGATTATGGCATGGACTACTGGGGTCAGGGTACGACTGTAACAGTTAGTAG<br>TGGTGGAGGCGGCAGTGGCGGGGGGGGAAGCGGAGGAGGGGGTTCTGGTGAC<br>ATAGTTATGACCCAATCCCCAGATAGTTTGGCGGTTTCTCTGGGCGAGAGGG<br>CAACGATTAATTGTCGCGCATCAAAGAGCGTTTCAACGAGCGGATATTCTTT<br>TATGCATTGGTACCAGCAAAAACCCGGACAACCGCCGAAGCTGCTGATCTAC<br>TTGGCTTCAAATCTTGAGTCTGGGGTGCCGGACCGATTTTCTGGTAGTGGAA<br>GCGGAACTGACTTTACGCTCACGATCAGTTCACTGCAGGCTGAGGATGTAGC<br>GGTCTATTATTGCCAGCACAGTAGAGAAGTCCCCTGGACCTTCGGTCAAGGC<br>ACGAAAGTAGAAATTAAAAGTGCTGCTGCCTTTGTCCCGGTATTTCTCCCAG<br>CCAAACCGACCACGACTCCCGCCCCGCGCCCTCCGACACCCGCTCCCACCAT<br>CGCCTCTCAACCTCTTAGTCTTCGCCCCGAGGCATGCCGACCCGCCGCCGGG<br>GGTGCTGTTCATACGAGGGGCTTGGACTTCGCTTGTGATATTTACATTTGGG<br>CTCCGTTGGCGGGTACGTGCGGCGTCCTTTTGTTGTCACTCGTTATTACTTT<br>GTATTGTAATCACAGGAATCGCAAACGGGGCAGAAAGAAACTCCTGTATATA<br>TTCAAACAACCATTTATGAGACCAGTACAAACTACTCAAGAGGAAGATGGCT<br>GTAGCTGCCGATTTCCAGAAGAAGAAGAAGGAGGATGTGAACTGCGAGTGAA<br>GTTTTCCCGAAGCGCAGACGCTCCGGCATATCAGCAAGGACAGAATCAGCTG<br>TATAACGAACTGAATTTGGGACGCCGCGAGGAGTATGACGTGCTTGATAAAC | 45 |

TABLE 12-continued

| Sequences of Anti-CD70 CAR Construct Components. | | |
|---|---|---|
| Description | Sequence | SEQ ID NO: |
| | GCCGGGGGAGAGACCCGGAAATGGGGGGTAAACCCCGAAGAAAGAATCCCCA AGAAGGACTCTACAATGAACTCCAGAAGGATAAGATGGCGGAGGCCTACTCA GAAATAGGTATGAAGGGCGAACGACGACGGGGAAAAGGTCACGATGGCCTCT ACCAAGGGTTGAGTACGGCAACCAAAGATACGTACGATGCACTGCATATGCA GGCCCTGCCTCCCAGATAA | |
| CD70 CAR amino acid sequence (CD70B scFV with 41BB) | MALPVTALLLPLALLLHAARPQVQLVQSGAEVKKPGASVKVSCKASGYTFTN YGMNWVRQAPGQGLKWMGWINTYTGEPTYADAFKGRVTMTRDTSISTAYMEL SRLRSDDTAVYYCARDYGDYGMDYWGQGTTVTVSSGGGGSGGGGSGGGGSGD IVMTQSPDSLAVSLGERATINCRASKSVSTSGYSFMHWYQQKPGQPPKLLIY LASNLESGVPDRFSGSGSGTDFTLTISSLQAEDVAVYYCQHSREVPWTFGQG TKVEIKSAAAFVPVFLPAKPTTTPAPRPPTPAPTIASQPLSLRPEACRPAAG GAVHTRGLDFACDIYIWAPLAGTCGVLLLSLVITLYCNHRNRKRGRKKLLYI FKQPFMRPVQTTQEEDGCSCRFPEEEEGGCELRVKFSRSADAPAYQQGQNQL YNELNLGRREEYDVLDKRRGRDPEMGGKPRRKNPQEGLYNELQKDKMAEAYS EIGMKGERRRGKGHDGLYQGLSTATKDTYDALHMQALPPR | 46 |
| CD70B scFv nucleotide sequence | CAGGTCCAGTTGGTGCAAAGCGGGGCGGAGGTGAAAAAACCCGGCGCTTCCG TGAAGGTGTCCTGTAAGGCGTCCGGTTATACGTTCACGAACTACGGGATGAA TTGGGTTCGCCAAGCGCCGGGGCAGGGACTGAAATGGATGGGGTGGATAAAT ACCTACACCGGCGAACCTACATACGCCGACGCTTTTAAAGGGCGAGTCACTA TGACGCGCGATACCAGCATATCCACCGCATACATGGAGCTGTCCCGACTCCG GTCAGACGACACGGCTGTCTACTATTGTGCTCGGGACTATGGCGATTATGGC ATGGACTACTGGGGTCAGGGTACGACTGTAACAGTTAGTAGTGGTGGAGGCG GCAGTGGCGGGGGGGGAAGCGGAGGAGGGGGTTCTGGTGACATAGTTATGAC CCAATCCCCAGATAGTTTGGCGGTTTCTCTGGGCGAGAGGGCAACGATTAAT TGTCGCGCATCAAAGAGCGTTTCAACGAGCGGATATTCTTTTATGCATTGGT ACCAGCAAAAACCCGGACAACCGCCGAAGCTGCTGATCTACTTGGCTTCAAA TCTTGAGTCTGGGGTGCCGGACCGATTTTCTGGTAGTGGAAGCGGAACTGAC TTTACGCTCACGATCAGTTCACTGCAGGCTGAGGATGTAGCGGTCTATTATT GCCAGCACAGTAGAGAAGTCCCCTGGACCTTCGGTCAAGGCACGAAAGTAGA AATTAAA | 47 |
| CD70B scFv amino acid sequence (linker underlined) | QVQLVQSGAEVKKPGASVKVSCKASGYTFTNYGMNWVRQAPGQGLKWMGWIN TYTGEPTYADAFKGRVTMTRDTSISTAYMELSRLRSDDTAVYYCARDYGDYG MDYWGQGTTVTVSSGGGGSGGGGSGGGGSGDIVMTQSPDSLAVSLGERATIN CRASKSVSTSGYSFMHWYQQKPGQPPKLLIYLASNLESGVPDRFSGSGSGTD FTLTISSLQAEDVAVYYCQHSREVPWTFGQGTKVEIK | 48 |
| CD70 VH | QVQLVQSGAEVKKPGASVKVSCKASGYTFTNYGMNWVRQAPGQGLKWMGWIN TYTGEPTYADAFKGRVTMTRDTSISTAYMELSRLRSDDTAVYYCARDYGDYG MDYWGQGTTVTVSS | 49 |
| CD70 VL | DIVMTQSPDSLAVSLGERATINCRASKSVSTSGYSFMHWYQQKPGQPPKLLI YLASNLESGVPDRFSGSGSGTDFTLTISSLQAEDVAVYYCQHSREVPWTFGQ GTKVEIK | 50 |
| Linker | GGGGSGGGGSGGGGSG | 51 |
| signal peptide | MLLLVTSLLLCELPHPAFLLIP | 52 |
| signal peptide | MALPVTALLLPLALLLHAARP | 53 |
| CD8a transmembrane domain | FVPVFLPAKPTTTPAPRPPTPAPTIASQPLSLRPEACRPAAGG AVHTRGLDFACDIYIWAPLAGTCGVLLLSLVITLYCNHRNR | 54 |
| CD8a transmembrane | IYIWAPLAGTCGVLLLSLVITLY | 55 |
| 4-1BB nucleotide sequence | AAACGGGGCAGAAAGAAACTCCTGTATATATTCAAACAACCATTTATGAGAC CAGTACAAACTACTCAAGAGGAAGATGGCTGTAGCTGCCGATTTCCAGAAGA AGAAGAAGGAGGATGTGAACTG | 56 |
| 4-1BB amino acid sequence | KRGRKKLLYIFKQPFMRPVQTTQEEDGCSCRFPEEEEGGCEL | 57 |
| CD28 nucleotide sequence | TCAAAGCGGAGTAGGTTGTTGCATTCCGATTACATGAATATGACTCCTCGCC GGCCTGGGCCGACAAGAAAACATTACCAACCCTATGCCCCCCCACGAGACTT CGCTGCGTACAGGTCC | 58 |
| CD28 amino acid sequence | SKRSRLLHSDYMNMTPRRPGPTRKHYQPYAPPRDFAAYRS | 59 |

TABLE 12-continued

Sequences of Anti-CD70 CAR Construct Components.

| Description | Sequence | SEQ ID NO: |
|---|---|---|
| CD3ζ nucleotide sequence | CGAGTGAAGTTTTCCCGAAGCGCAGACGCTCCGGCATATCAGCAAGGACAGAATCAGCTGTATAACGAACTGAATTTGGGACGCCGCGAGGAGTATGACGTGCTTGATAAACGCCGGGGGAGAGACCCGGAAATGGGGGGTAAACCCCGAAGAAAGAATCCCCAAGAAGGACTCTACAATGAACTCCAGAAGGATAAGATGGCGGAGGCCTACTCAGAAATAGGTATGAAGGGCGAACGACGACGGGGAAAAGGTCACGATGGCCTCTACCAAGGGTTGAGTACGGCAACCAAAGATACGTACGATGCACTGCATATGCAGGCCCTGCCTCCCAGA | 60 |
| CD3ζ amino acid sequence | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 61 |
| TRAC-LHA | GAGATGTAAGGAGCTGCTGTGACTTGCTCAAGGCCTTATATCGAGTAAACGGTAGTGCTGGGGCTTAGACGCAGGTGTTCTGATTTATAGTTCAAAACCTCTATCAATGAGAGAGCAATCTCCTGGTAATGTGATAGATTTCCCAACTTAATGCCAACATACCATAAACCTCCCATTCTGCTAATGCCCAGCCTAAGTTGGGGAGACCACTCCAGATTCCAAGATGTACAGTTTGCTTTGCTGGGCCTTTTTCCCATGCCTGCCTTTACTCTGCCAGAGTTATATTGCTGGGGTTTTGAAGAAGATCCTATTAAATAAAAGAATAAGCAGTATTATTAAGTAGCCCTGCATTTCAGGTTTCCTTGAGTGGCAGGCCAGGCCTGGCCGTGAACGTTCACTGAAATCATGGCCTCTTGGCCAAGATTGATAGCTTGTGCCTGTCCCTGAGTCCCAGTCCATCACGAGCAGCTGGTTTCTAAGATGCTATTTCCCGTATAAAGCATGAGACCGTGACTTGCCAGCCCCACAGAGCCCCGCCCTTGTCCATCACTGGCATCTGGACTCCAGCCTGGGTTGGGGCAAAGAGGGAAATGAGATCATGTCCTAACCCTGATCCTCTTGTCCCACAGATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCA | 62 |
| EF1α promoter | GGCTCCGGTGCCCGTCAGTGGGCAGAGCGCACATCGCCCACAGTCCCCGAGAAGTTGGGGGGAGGGGTCGGCAATTGAACCGGTGCCTAGAGAAGGTGGCGCGGGGTAAACTGGGAAAGTGATGTCGTGTACTGGCTCCGCCTTTTTCCCGAGGGTGGGGGAGAACCGTATATAAGTGCAGTAGTCGCCGTGAACGTTCTTTTTCGCAACGGGTTTGCCGCCAGAACACAGGTAAGTGCCGTGTGTGGTTCCCGCGGGCCTGGCCTCTTTACGGGTTATGGCCCTTGCGTGCCTTGAATTACTTCCACTGGCTGCAGTACGTGATTCTTGATCCCGAGCTTCGGGTTGGAAGTGGGTGGGAGAGTTCGAGGCCTTGCGCTTAAGGAGCCCCTTCGCCTCGTGCTTGAGTTGAGGCCTGGCCTGGGCGCTGGGGCCGCCGCGTGCGAATCTGGTGGCACCTTCGCGCCTGTCTCGCTGCTTTCGATAAGTCTCTAGCCATTTAAAATTTTTGATGACCTGCTGCGACGCTTTTTTTCTGGCAAGATAGTCTTGTAAATGCGGGCCAAGATCTGCACACTGGTATTTCGGTTTTTGGGGCCGCGGGCGGCGACGGGGCCCGTGCGTCCCAGCGCACATGTTCGGCGAGGCGGGGCCTGCGAGCGCGGCCACCGAGAATCGGACGGGGGTAGTCTCAAGCTGGCCGGCCTGCTCTGGTGCCTGGCCTCGCGCCGCCGTGTATCGCCCCGCCCTGGGCGGCAAGGCTGGCCCGGTCGGCACCAGTTGCGTGAGCGGAAAGATGGCCGCTTCCCGGCCCTGCTGCAGGGAGCTCAAAATGGAGGACGCGGCGCTCGGGAGAGCGGGCGGGTGAGTCACCCACACAAAGGAAAAGGGCCTTTCCGTCCTCAGCCGTCGCTTCATGTGACTCCACGGAGTACCGGGCGCCGTCCAGGCACCTCGATTAGTTCTCGAGCTTTTGGAGTACGTCGTCTTTAGGTTGGGGGGAGGGGTTTTATGCGATGGAGTTTCCCCACACTGAGTGGGTGGAGACTGAAGTTAGGCCAGCTTGGCACTTGATGTAATTCTCCTTGGAATTTGCCCTTTTTGAGTTTGGATCTTGGTTCATTCTCAAGCCTCAGACAGTGGTTCAAAGTTTTTTTCTTCCATTTCAGGTGTCGTGA | 63 |
| Synthetic poly(A) signal | AATAAAATCGCTATCCATCGAAGATGGATGTGTGTTGGTTTTTTGTGTG | 64 |
| TRAC-RHA | TGGAGCAACAAATCTGACTTTGCATGTGCAAACGCCTTCAACAACAGCATTATTCCAGAAGACACCTTCTTCCCCAGCCCAGGTAAGGGCAGCTTTGGTGCCTTCGCAGGCTGTTTCCTTGCTTCAGGAATGGCCAGGTTCTGCCCAGAGCTCTGGTCAATGATGTCTAAAACTCCTCTGATTGGTGGTCTCGGCCTTATCCATTGCCACCAAAACCCTCTTTTTACTAAGAAACAGTGAGCCTTGTTCTGGCAGTCCAGAGAATGACACGGGAAAAAAGCAGATGAAGAGAAGGTGGCAGGAGAGGGCACGTGGCCCAGCCTCAGTCTCTCCAACTGAGTTCCTGCCTGCCTGCCTTTGCTCAGACTGTTTGCCCCTTACTGCTCTTCTAGGCCTCATTCTAAGCCCCTTCTCCAAGTTGCCTCTCCTTATTTCTCCCTGTCTGCCAAAAAATCTTTCCCAGCTCACTAAGTCAGTCTCACGCAGTCACTCATTAACCCACCAATCACTGATTGTGCCGGCACATGAATGCACCAGGTGTTGAAGTGGAGGAATTAAAAAGTCAGATGAGGGGTGTGCCCAGAGGAAGCACCATTCTAGTTGGGGGAGCCCATCTGTCAGCTGGGAAAAGTCCAAATAACTTCAGATTGGAATGTGTTTTAACTCAGGGTTGAGAAAACAGCTACCTTCAGGACAAAAGTCAGGGAAGGGCTCTCTGAAGAAATGCTACTTGAAGATACCAGCCCTACCAAGGGCAGGGAGAGGACCCTATAGAGGCCTGGGACAGGAGCTCAATGAGAAAGG | 65 |

Manufacturing Process Description of CTX130

(i) T Cell Enrichment

T cells were enriched from the leukapheresis materials (Leukopaks) via magnetic separation using a mixture of anti-CD8 and anti-CD4 antibody-coated magnetic beads using an automated cell processing system. Prior to enrichment, leukopaks were sampled for cell count and viability (≥80%).

Enriched cells were isolated in PBS/EDTA Buffer with HSA, and then sampled for cell count, viability (≥80%), T cell purity (≥70% CD3), and sterility. The cells were then centrifuged at 4±1° C. and resuspended in CryoStor CS5 at a target concentration of $50\times10^6$ viable cells/mL.

(ii) T Cell Cryopreservation

The cells were sampled for cell count, viability (≥80%) and then aliquoted into ethyl vinyl acetate cryobags at the target cell number of $2{,}500\times10^6$ cells/bag (30-70 mL of cell suspension). One Leukopak may be sufficient to produce 1-2 bags of T cells. Each bag is heat-sealed, labeled, stored at 2-8° C. until transfer to a controlled-rate freezer and subsequently transferred to vapor phase liquid nitrogen for storage.

(iii) T Cell Thawing, First Electroporation, and Activation

One frozen bag of enriched T cells was thawed, transferred into a 3 L bag and diluted into Supplemented X-VIVO™ 15 media (X-VIVO™ 15, 5% Human Serum, 100 IU/mL rhIL2, 100 IU/mL rhIL7). The cells were sampled for cell count and viability (≥70%).

The cells were centrifuged at 540 g at 20±1° C. for 15 minutes. The cell pellet was resuspended in Electroporation Buffer and centrifuged again under the same conditions. The cells were resuspended in Electroporation Buffer a second time to a target concentration of $300\times10^6$ cells/mL.

Cas9 nuclease was mixed with CD70-7 sgRNA in a microcentrifuge tube and incubated for no less than 10 minutes at room temperature to form the ribonucleoprotein (RNP) complex. The Cas9/sgRNA was then mixed with the cells, bringing Cas9 and CD70-7 sgRNA to a final concentration of 0.15 mg/mL and 0.16 mg/mL, respectively.

The mixture was aliquoted and loaded into an electroporation cassette by pipetting. Cassettes were capped and sequentially electroporated using the transfection system based on flow electroporation.

After electroporation, the cells were pooled from each cassette in a 125 mL Erlenmeyer flask and incubated at 37° C. for no less than 20 minutes. The cells were sampled for viability (≥50%) and count. Soluble colloidal polymeric nanomatrix conjugated to recombinant humanized CD3 and CD28 agonists solution was then added at the ratio of 1:12.5 (v/v) to activate the cells.

The cells were seeded to a target density $2\times10^6$ viable cells/mL in static cell culture vessels, each at a total volume of approximately 500 mL of Supplemented X-VIVO™ 15 media/colloidal polymeric nanomatrix conjugated to recombinant humanized CD3 and CD28 agonists.

The static cell culture vessels were incubated at 37±1° C. and 5±1% $CO_2$ for 72±4 hours. Throughout the process, whenever the static cell culture vessels are handled, they were inspected for tears and leaks, and the presence of clear, yellow medium.

(iv) Dilution

Three (3) days later, supplemented X-VIVO™ 15 media was added to each static cell culture vessel to a final volume of 5 L. The cells were further incubated at 37±1° C. and 5±1% $CO_2$ overnight.

(v) Second Electroporation and Transduction

The volume of Supplemented X-VIVO™ 15 media was reduced to a final volume of approximately 500 mL using a pump connected to the static cell culture vessel dip-tube.

The static cell culture vessel was gently swirled to allow the cells to resuspend in the media. The cells were sampled for cell count, viability (≥70%).

The cells were transferred to 500 mL centrifuge tubes and centrifuged at 540 g, at 20±1° C. for 15 minutes. The cell pellet was resuspended in Electroporation Buffer and centrifuged again under the same conditions. The cells were resuspended in Electroporation Buffer a second time to a target concentration of $300\times10^6$ cells/mL.

Cas9 nuclease was mixed with TA-1 sgRNA and with β2M-1 sgRNA in separate microcentrifuge tubes. Each solution was incubated for no less than 10 minutes at room temperature to form each ribonucleoprotein (RNP) complex. The two Cas9/sgRNA mixtures were combined, and mixed with the cells, bringing Cas9, TA-1 and β2M-1 to a final concentration of 0.3 mg/mL, 0.08 mg/mL, and 0.2 mg/mL, respectively.

The mixture was aliquoted and loaded into an electroporation cassette by pipetting. Cassettes were capped and sequentially electroporated using the transfection system based on flow electroporation.

After electroporation, the cells were pooled from each cassette in a 125 mL Erlenmeyer flask and incubated at 37° C. for no less than 20 minutes. The cells were sampled for viability (≥70%) and count. The cells were diluted to a target of $1\times10^7$ cells/mL with X-VIVO™ 15 media, and freshly thawed rAAV-145b was added at a MOI of 20,000-50,000 vg/cell. The cells were incubated at 37° C., 5% $CO_2$ for no less than 60 minutes.

(vi) Cell Expansion

Cells were diluted with Supplemented X-VIVO™ 15 media, sampled for cell viability (≥70%) and count, and seeded to a density between $0.2\times10^6$ viable cells/cm$^2$ to $0.5\times10^6$ viable cells/cm$^2$ into two static cell culture vessels, and one smaller static cell culture vessel that acted as a satellite culture for cell monitoring). The static cell culture vessels were incubated at 37±1° C. and 5±1% $CO_2$.

The cell cultures were incubated for up to 9 days. During this time, the cultures were supplemented every 3 to 4 days with 100 IU of rhIL2 and rhIL7 per mL of culture volume. The satellite cell culture was tested for cell count, viability, and T cell purity throughout expansion. When the cell density in the satellite culture reaches approximately $30\times10^6$/cm$^2$ the TCRαβ depletion was performed. If cell density of the satellite does not reach $30\times10^6$/cm$^2$, TCRαβ depletion on the main cultures was performed on Day 9.

(vii) TCRαβ Depletion

The medium of each static cell culture vessel was reduced to a final volume of approximately 500 mL using a pump connected to the static cell culture vessel dip-tube. After the bulk of the media was removed, the static cell culture vessels were gently swirled to resuspend the cells in the media.

The cells were transferred to 500 mL centrifuge tubes fitted with dip-tubes that connect to the static cell culture vessel. The cells were sampled for viability (≥70%), count, and % CAR. The cells were then centrifuged at 540 g at 20±1° C. for 15 minutes. The cell pellets were resuspended and pooled in less than 650 mL PBS/EDTA containing 0.5% HSA. The cell suspension was transferred to a sterile bag which is connected to the automated cell processing system. The automated cell processing system incubates the cells with a biotin-conjugated anti-TCRαβ antibody. The cells were washed and incubated with anti-biotin magnetic beads to allow for depletion of the TCRαβ$^{+}$ cells using the automated cell processing system.

The cells were tested for cell count, viability (≥70%), and % CAR cells.

(viii) Cell Recovery

The depleted cells were resuspended in Supplemented X-VIVO™ 15 media and transferred into 3 L bag(s), seeded into static cell culture vessel(s) and incubated overnight at 37±1° C. and 5±1% $CO_2$.

(ix) Cell Harvest (Drug Substance)

To harvest cells, the static cell culture vessels were removed from the incubator and allowed to rest for sedimentation of cells. The growth medium was removed from each static cell culture vessel using a pump to a final volume of approximately 500 mL. The removed media was sampled for sterility.

The static cell culture vessels were gently swirled to allow the cells to resuspend in the media. The contents of each static cell culture vessel were transferred in a 3 L transfer bag using the pump, and sampled for concentration, viability and Drug Substance lot release testing. The cells were then filtered through a 40 μm blood transfusion filter by gravity into a separate sterile 3 L bag.

Characterization of CTX130

CTX130 is a CD70-directed T cell immunotherapy comprised of allogeneic T cells that express an anti-CD70 CAR, and that have genetically disrupted CD70, TRAC, and β2M genes. Nonclinical pharmacology and toxicology studies were conducted to characterize the potential efficacy and toxicity of non-GMP development lots of CTX130.

Production and Characterization of Non-GMP Development Lots of CTX130

The objective of this study was to determine whether reproducible production of non-GMP CD70 CAR T cells was achieved using methods described herein.

Three individual human T cell donors were edited to create non-GMP development lots of CTX130 with RNPs containing Cas9 and gRNA against CD70 in an initial step followed by RNPs containing Cas9 and gRNAs against TRAC and β2M followed by transduction with AAV6 containing the donor template encoding the CAR in a second step. The cells were subsequently depleted for remaining residual TCR cells using column purification.

In brief, the T cells from 3 individual donors were thawed and electroporated with RNPs containing Cas9 and gRNA targeting the CD70 loci, then activated using a colloidal polymeric nanomatrix conjugated to recombinant humanized CD3 and CD28 agonists for 3 days. On day 4, beads were diluted and T cells were allowed to expand for an additional day. On day 5, cells were subject to electroporation with RNPs containing Cas9 and gRNAs targeting the TRAC and β2M loci, followed by incubation with an AAV6 containing an HDR template containing the CD70 CAR. Ten days following the second gene editing step cells were analyzed using a flow-cytometer to evaluate the knock-out efficiencies of TRAC, β2M and CD70, and the percentage of cells expressing the CAR. Staining was performed using antibodies against TRAC, β2M and CD70 proteins, while CAR expression was detected through staining with anti-mouse Fab2 antibody labeled with biotin, followed by incubation with fluorescent streptavidin.

Analysis of edited cells showed 99.7±0.1% TRAC negative cells, 79.4±1.1% β2M negative cells, and 98.9±0.3% CD70$^{-}$ cells (Table 13). CAR expression was detected in 80.8±8.4% of cells in the 3 tested donors (Table 13). An additional research lot of CTX130 was generated using a fourth donor (Donor 4) using the same process but the research lot was not depleted for remaining residual TCR cells.

TABLE 13

Summary of editing efficiency in CTX130 lots from 4 separate donors.

| | Sample | | | |
|---|---|---|---|---|
| | % TCR$^{-}$ | % β2M$^{-}$ | % CD70$^{-}$ | % CAR$^{+}$ |
| Donor 1 | 99.6 | 80.63 | 99.15 | 85.2 |
| Donor 2 | 99.8 | 78.81 | 98.62 | 71.1 |
| Donor 3 | 99.9 | 78.7 | 99.06 | 86.1 |
| Average | 99.7 ± 0.1 | 79.4 ± 1.1 | 98.9 ± 0.3 | 80.8 ± 8.4 |
| Donor 4* | 99.4 | 85.9 | 90.2 | 79 |

*Research lot of CTX130 produced without depletion of residual TCR$^{+}$ cells; not included in Average.

(i) Effector Cytokine Release

The objective of this study was to assess the ability of CTX130 cells to secrete interferon-gamma (IFNγ) and Interleukin 2 (IL-2) when co-cultured with CD70$^{+}$ or CD70$^{-}$ cells.

Human target cells (CD70$^{+}$ cell lines A498 and ACHN, and CD70$^{-}$ line MCF7) were co-cultured with T cells at varying ratios (from 0.125:1 to 4:1 T cells to target cells) at 50,000 target cells per well in a 96-well plate for 24 hours. Target cells were incubated with either CTX130 cells or control cells (unedited T cells). Levels of IFNγ and IL-2 in culture media supernatants were measured and demonstrated that CTX130 has the ability to secrete IFNγ and IL-2 when co-cultured with CD70+, but not when co-cultured with CD70$^{-}$ cells.

(ii) Tumor Cell Cytotoxicity

The objective of this study was to assess the ability of CTX130 cells to kill CD70$^{+}$ cells. In brief, human target CD70$^{+}$ cells (A498 and ACHN) were plated at 50,000 target cells per well in a 96-well plate overnight, and then co-cultured with either CTX130 or unedited T cells at varying ratios (from 0.125:1 to 4:1 T cells to target cells) for 24 hours Killing of the target cells was measured and demonstrated that CTX130 cells killed CD70$^{+}$ cell lines in vitro.

(iii) Other Studies

Other studies showed the ability of CTX130 cells to limit tumor cell growth in subcutaneous models of renal cell carcinoma and Sézary Syndrome and demonstrated that CTX130 treatment was well tolerated by mice with respect to each of the measured endpoints including survival, clinical signs of GvHD, and body weight.

(iv) Human Tissue Cross Reactivity

The objective of this study was to evaluate the selectivity of the anti-CD70 CAR contained in CTX130 in an immunohistochemistry-based tissue cross-reactivity study. The test article used in this study was the antibody from which the scFv portion of CTX130 was derived. A standard panel of 32 human tissues was evaluated at two concentrations of antibody: an optimal concentration (2.5 μg/mL) and a high concentration (10.0 μg/mL), in an attempt to capture any potential binding to human tissues. For each tissue tested, sections from 3 donors were evaluated. Minimal to moderate positive staining was observed in some lymphoid tissues (lymph node and tonsil), consistent with normal CD70 expression patterns. No staining was observed in the remaining tissues of the panel. Robust staining was observed in a positive control (human renal cell carcinoma tumor cells).

(v) Cytokine-Independent Growth

The objective of this study is to assess the ability of CTX130 to proliferate in the absence of serum and cytokines IL-2 and IL-7. In brief, CTX130 cells from research lots and non-GMP development lots were grown either in full T cell media, media containing serum but no IL2 or IL7 cytokines (serum only), or no serum or cytokines (basal media). Day 0 occurs 14 days post genome editing. No growth in the absence of cytokines was observed for both research lots and non-GMP development lots. These results demonstrate a lack of growth and proliferation in serum and cytokine free media post genome editing.

Example 6: Improved Cell Expansion

Optimized Electroporation for Increased CTX130 Cell Expansion Output

The methods as described in the present disclosure utilize electroporation to deliver various nucleic acids and polypeptides to recipient T-cells, including, for example, various ribonucleoprotein (RNP) complexes comprising Cas9 and guide RNA complexes. The instrumentation used in the electroporation process is not particularly limited, as any suitable electroporation instrument from various manufacturers can find use in the methods described herein. The cell seeding density used in the electroporation is not particularly limited.

The present example uses an electroporation instrument capable of electroporating increased numbers of cells in cassettes capable of retaining larger volumes while maintaining efficient editing. The larger electroporation capacity increases, for example as much as doubling, the output of any given engineered T-cell, for example the CTX130 engineered T-cell product, by providing a greater number of edited cells for transduction and expansion. This is a benefit in manufacturing, as this increased capacity comes without the need to extend the process duration and or cell doublings.

For example, additional cells are available to seed additional T-cell culture vessels (500 $cm^2$ gas permeable membrane surface area with 5000 mL media capacity), such as 2 or more additional culture vessels. For example, with the increase number of cells, up to 4× culture vessels can be seeded, where $300e6 \leq x \leq 600e6$ cells can be seeded in 2× culture vessels, $600e6 \leq x \leq 800e6$ cells can be seeded in 3× culture vessels, or ≤800e6 cells can be seeded in 4× culture vessels.

In some aspects, between about 400,000 cells/$cm^2$ and 500,000 cells/$cm^2$ are seeded per culture vessel. Alternatively, between about 250,000 cells/$cm^2$ and 500,000 cells/$cm^2$ are seeded per culture vessel, or between about 300,000 cells/$cm^2$ and 500,000 cells/$cm^2$ are seeded per culture vessel, or between about 150,000 cells/$cm^2$ and 250,000 cells/$cm^2$ are seeded per culture vessel, or between about 150,000 cells/$cm^2$ and 500,000 cells/$cm^2$ are seeded per culture vessel, or between about 150,000 cells/$cm^2$ and 600,000 cells/$cm^2$ are seeded per culture vessel.

In some aspects, a target seeding density is at least about 150,000 cells/$cm^2$, or at least about 250,000 cells/$cm^2$, or at least about 300,000 cells/$cm^2$, or at least about 400,000 cells/$cm^2$, or at least about 500,000 cells/$cm^2$.

In some aspects, a target seeding density is about 250,000 cells/$cm^2$. In other aspects, a target seeding density is about 500,000 cells/$cm^2$.

Electroporation cassettes capable of retaining volumes of up to 1 mL can be used. Using this system, $2.7\times10^9$ cells can be electroporated in up to seven G1000 cassettes. Retrieval of the cells from cassettes with a single-use blunt tip needles attached to a 3 mL syringe will also eliminate the risk of micropipette tip ejection into the Erlenmeyer.

Use of a system with larger capacity also facilitates the cell transduction step. Doubling the current maximum of 7e8 cells for transduction to 1.4e9 cells produces sufficient material to seed up to four cell culture vessels for expansion. Therefore, a fixed day 9 depletion can be maintained, effectively up to doubling the output per run in the same amount of processing time.

Other steps in the process of CTX130 production are as described in the examples above.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising"

can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for manufacturing genetically engineered T cells, the method comprising:

(i) providing a first population of T cells;

(ii) introducing into the first population of T cells by electroporation a first ribonucleoprotein (RNP) complex comprising a first Cas9 enzyme and a first guide RNA (gRNA) targeting a CD70 gene to produce a second population of T cells, wherein the second population of T cells comprises T cells having a disrupted CD70 gene;

(iii) introducing into the second population of T cells a second RNP complex comprising a second Cas9 enzyme and a second gRNA targeting a T cell receptor alpha chain constant region (TRAC) gene, and a third RNP complex comprising a third Cas9 enzyme and a third gRNA targeting a beta-2 microglobulin (β2M) gene to produce a third population of T cells, wherein the third population of T cells comprises T cells having the disrupted CD70 gene disrupted, a disrupted TRAC gene, and a disrupted β2M gene, wherein the second RNP complex and the third RNP complex are introduced into the second population of T cells in one electroporation event and wherein the second RNP complex and the third RNP complex are formed prior to the electroporation event;

(iv) incubating the third population of T cells with an adeno-associated viral (AAV) vector to produce a fourth population of T cells, wherein the AAV vector comprises a nucleic acid sequence encoding a chimeric antigen receptor (CAR) and wherein the nucleic acid sequence is flanked by homologous sequences to the TRAC gene, and wherein the fourth population of T cells comprises T cells expressing the CAR and having the disrupted CD70 gene, the disrupted TRAC gene, and the disrupted β2M gene;

(v) expanding the fourth population of T cells thereby producing an expanded T cell population;

(vi) removing TCRαβ$^+$ T cells from the expanded T cell population to produce a population of genetically engineered T cells, wherein the population of genetically engineered T cells comprises T cells expressing the CAR and having the disrupted CD70 gene, the disrupted TRAC gene, and the disrupted β2M gene; and (vii) harvesting the population of genetically engineered T cells.

2. The method of claim 1, wherein the first population of T cells is derived from cryopreserved T cells enriched from human blood cells.

3. The method of claim 1, wherein the first population of T cells is prepared by a process comprising: (a) obtaining blood cells from a human donor; and (b) enriching CD4$^+$ T cells and/or CD8$^+$ T cells from the blood cells.

4. The method of claim 3, wherein step (b) is performed using magnetic beads conjugated with anti-CD4 and/or anti-CD8 antibodies.

5. The method of claim 3, further comprising (c) cryopreserving the enriched CD4$^+$ T cells and CD8$^+$ T cells produced in step (b).

6. The method of claim 1, wherein the first population of T cells has a cell viability of at least 80% and/or a purity of at least 80% of CD4$^+$ and CD8$^+$ T cells.

7. The method of claim 1, wherein the concentration of the first Cas9 enzyme is 0.15 mg/mL and the concentration of the first gRNA targeting the CD70 gene is 0.16 mg/mL.

8. The method of claim 1, wherein the cell concentration in step (ii) is $100\times10^6$ cells/mL to $350\times10^6$ cells/mL.

9. The method of claim 8, wherein the cell concentration in step (ii) is $300\times10^6$ cells/mL.

10. The method of claim 1, wherein the expanding step comprises seeding the T cells at a density between 150,000 cells/cm$^2$ and 600,000 cells/cm$^2$, in a cell vessel.

11. The method of claim 10, wherein the expanding step comprises seeding the T cells at a density between 300,000 cells/cm$^2$ and 500,000 cells/cm$^2$ in a cell vessel.

12. The method of claim 1, the method further comprising after step (ii) and before step (iii), incubating the second population of T cells in the presence of a T cell activating agent in a cell culture vessel to produce an activated population of T cells, wherein the activated population of T cells comprises activated T cells having the disrupted CD70 gene.

13. The method of claim 12, wherein the T cell activating agent comprises a CD3 agonist and a CD28 agonist, and wherein the CD3 agonist and CD28 agonist are attached to a nanomatrix particle.

14. The method of claim 12, wherein incubating the second population of T cells in the presence of a T cell activating agent in a cell culture vessel is at a cell seeding density of $2\times10^6$/cm$^2$ and a cell concentration of $2\times10^6$ cells/mL for 72 hours.

15. The method of claim 12, wherein the ratio of the T cell activating agent to medium in the mixture is 1:12.5 (v/v).

16. The method of claim 12, further comprising diluting the T cell activating agent in the activated population of T cells after incubating the second population of T cells in the presence of a T cell activating agent to reduce activation and to allow cells to recover before step (iii).

17. The method of claim 1, wherein the amount of the second Cas9 enzyme in the second RNP complex is the same as the amount of the third Cas9 enzyme in the third RNP complex.

18. The method of claim 1, wherein the concentration of the second Cas9 enzyme is 0.15 mg/mL, the concentration of the third Cas9 enzyme is 0.15 mg/mL, the concentration of the second gRNA targeting the TRAC gene is 0.08 mg/mL, and the concentration of the third gRNA targeting the β2M gene is 0.2 mg/mL.

19. The method of claim 1, wherein the concentration of cells in the expanded T cell population in step (v) is $100\times10^6$ cells/mL to $400\times10^6$ cells/mL.

20. The method of claim 1, wherein the cell number in step (iv) is $3\times10^8$ cells.

21. The method of claim 1, wherein the AAV vector has a multiplicity of infection (MOI) value of 10,000 to 80,000.

22. The method of claim 21, wherein the MOI of the AAV vector is 20,000.

23. The method of claim 21, wherein the AAV vector is AAV serotype 6 (AAV6) vector.

24. The method of claim 1, wherein step (v) is performed by culturing the fourth population of T cells in a cell culture vessel at a seeding density of $2\times10^5$ cells/cm$^2$ to $7\times10^5$ cells/cm$^2$ for 6 days to 12 days.

25. The method of claim 24, wherein the fourth population of T cells is cultured at a seeding density of $3\times10^5$ cells/cm$^2$ to $5\times10^5$ cells/cm$^2$.

26. The method of claim 24, wherein the cell culture vessel is a static cell culture vessel allowing for cell expansion for 10 days to 12 days without medium change.

27. The method of claim 24, wherein the cell culture vessel is a static cell culture vessel allowing for cell expansion for 7 days to 9 days without medium change.

28. The method of claim 1, wherein step (v) is performed by culturing the fourth population of T cells in a cell culture vessel at a seeding density of $2\times10^5$ cells/cm$^2$ to $5\times10^5$ cells/cm$^2$ for 7 days to 9 days.

29. The method of claim 1, wherein step (vi) is performed by contacting the expanded cells to beads on which anti-TCRαβ antibodies are immobilized, and collecting unbound cells.

30. The method of claim 1, wherein the first Cas9 enzyme, the second Cas9 enzyme, and/or the third Cas9 enzyme is a *Streptococcus pyogenes* Cas9 nuclease (spCas9).

31. The method of claim 1, wherein the first Cas9 enzyme, the second Cas9 enzyme, and the third Cas9 enzyme are the same.

32. The method of claim 31, wherein the first Cas9 enzyme, the second Cas9 enzyme, and the third Cas9 enzyme comprise the amino acid sequence of SEQ ID NO: 1.

33. The method of claim 1, wherein the first gRNA targeting the CD70 gene comprises a spacer sequence of SEQ ID NO: 4.

34. The method of claim 33, wherein the first gRNA targeting the CD70 gene comprises the nucleotide sequence of SEQ ID NO: 2.

35. The method of claim 33, wherein the first gRNA, the second gRNA, the third gRNA, and/or a combination thereof, comprise one or more 2'-O-methyl phosphorothioate modification.

36. The method of claim 1, wherein the second gRNA targeting the TRAC gene comprises a spacer sequence of SEQ ID NO: 8.

37. The method of claim 36, wherein the second gRNA targeting the TRAC gene comprises the nucleotide sequence of SEQ ID NO: 6.

38. The method of claim 1, wherein the third gRNA targeting the β2M gene comprises a spacer sequence of SEQ ID NO: 12.

39. The method of claim 38, wherein the third gRNA targeting the β2M gene comprises the nucleotide sequence of SEQ ID NO: 10.

40. The method of claim 1, wherein the CAR comprises an extracellular domain targeting a cancer antigen, a transmembrane domain, a co-stimulatory domain, and a CD3ζ cytoplasmic signaling domain.

41. The method of claim 40, wherein the extracellular domain comprises a single-chain variable fragment (scFv), the transmembrane domain is derived from CD8a, and/or the co-stimulatory domain is derived from 4-1BB.

42. The method of claim 41, wherein the scFv fragment binds CD70.

43. The method of claim 42, wherein the CAR comprises the amino acid sequence of SEQ ID NO: 46.

* * * * *

```
                      SEQUENCE LISTING

<160> NUMBER OF SEQ ID NOS: 66

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
```

```
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620
```

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                 1015                1020

Lys Ser  Glu Gln Glu Ile Gly  Lys Ala Thr Ala Lys  Tyr Phe Phe
    1025                 1030                1035
```

```
Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

```
<210> SEQ ID NO 2
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
```

<222> LOCATION: (97)..(100)
<223> OTHER INFORMATION: modified with 2'-O-methyl phosphorothioate

<400> SEQUENCE: 2 gcuuugguco cauuggucgc guuuuagagc uagaaauagc aaguuaaaau aaggcuaguc 60
cguuaucaac uugaaaaagu ggcaccgagu cggugcuuuu 100

<210> SEQ ID NO 3
<211> LENGTH: 100
<212> TYPE: RNA
<213> ORGANISM: Artificial Sequence
<220> FEATURE:
<223> OTHER INFORMATION: Synthetic

<400> SEQUENCE: 3
gcuuuggucc cauuggucgc guuuuagagc uagaaauagc aaguuaaaau aaggcuaguc 60
cguuaucaac uugaaaaagu ggcaccgagu cggugcuuuu 100

<210> SEQ ID NO 4
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 4
gcuuuggucc cauuggucgc 20

<210> SEQ ID NO 5
<211> LENGTH: 20
<212> TYPE: RNA
<213> ORGANISM: Artificial Sequence
<220> FEATURE:
<223> OTHER INFORMATION: Synthetic

<400> SEQUENCE: 5
gcuuuggucc cauuggucgc 20

<210> SEQ ID NO 6
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 6
agagcaacag ugcuguggcc guuuuagagc uagaaauagc aaguuaaaau aaggcuaguc 60
cguuaucaac uugaaaaagu ggcaccgagu cggugcuuuu 100

<210> SEQ ID NO 7
<211> LENGTH: 100
<212> TYPE: RNA
<213> ORGANISM: Artificial Sequence
<220> FEATURE:

```
<223> OTHER INFORMATION: Synthetic

<400> SEQUENCE: 7

agagcaacag ugcuguggcc guuuuagagc uagaaauagc aaguuaaaau aaggcuaguc     60

cguuaucaac uugaaaaagu ggcaccgagu cggugcuuuu                          100


<210> SEQ ID NO 8
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 8

agagcaacag ugcuguggcc                                                 20


<210> SEQ ID NO 9
<211> LENGTH: 20
<212> TYPE: RNA
<213> ORGANISM: Artificial Sequence
<220> FEATURE:
<223> OTHER INFORMATION: Synthetic

<400> SEQUENCE: 9

agagcaacag ugcuguggcc                                                 20


<210> SEQ ID NO 10
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 10

gcuacucucu cuuucuggcc guuuuagagc uagaaauagc aaguuaaaau aaggcuaguc     60

cguuaucaac uugaaaaagu ggcaccgagu cggugcuuuu                          100


<210> SEQ ID NO 11
<211> LENGTH: 100
<212> TYPE: RNA
<213> ORGANISM: Artificial Sequence
<220> FEATURE:
<223> OTHER INFORMATION: Synthetic

<400> SEQUENCE: 11

gcuacucucu cuuucuggcc guuuuagagc uagaaauagc aaguuaaaau aaggcuaguc     60

cguuaucaac uugaaaaagu ggcaccgagu cggugcuuuu                          100


<210> SEQ ID NO 12
<211> LENGTH: 20
<212> TYPE: RNA
<213> ORGANISM: Artificial Sequence
<220> FEATURE:
<223> OTHER INFORMATION: Synthetic
```

<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 12
gcuacucucu cuuucuggcc 20

<210> SEQ ID NO 13
<211> LENGTH: 20
<212> TYPE: RNA
<213> ORGANISM: Artificial Sequence
<220> FEATURE:
<223> OTHER INFORMATION: Synthetic

<400> SEQUENCE: 13
gcuacucucu cuuucuggcc 20

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
gctttggtcc cattggtcgc ggg 23

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
gctttggtcc cattggtcgc 20

<210> SEQ ID NO 16
<211> LENGTH: 23
<212> TYPE: DNA
<213> ORGANISM: Artificial Sequence
<220> FEATURE:
<223> OTHER INFORMATION: Synthetic

<400> SEQUENCE: 16
agagcaacag tgctgtggcc tgg 23

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
agagcaacag tgctgtggcc 20

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18

```
gctactctct ctttctggcc tgg                                         23


<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19

gctactctct ctttctggcc                                             20


<210> SEQ ID NO 20
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 20

nnnnnnnnnn nnnnnnnnnn guuuuagagc uagaaauagc aaguuaaaau aaggcuaguc     60

cguuaucaac uugaaaaagu ggcaccgagu cggugcuuuu                          100


<210> SEQ ID NO 21
<211> LENGTH: 96
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 21

nnnnnnnnnn nnnnnnnnnn guuuuagagc uagaaauagc aaguuaaaau aaggcuaguc     60

cguuaucaac uugaaaaagu ggcaccgagu cggugc                               96


<210> SEQ ID NO 22
<211> LENGTH: 114
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: n is a, c, g, or u
<220> FEATURE:
<221> NAME/KEY: misc_feature
<222> LOCATION: (17)..(30)
<223> OTHER INFORMATION: may be absent
<220> FEATURE:
<221> NAME/KEY: misc_feature
<222> LOCATION: (108)..(114)
<223> OTHER INFORMATION: may be absent

<400> SEQUENCE: 22

nnnnnnnnnn nnnnnnnnnn nnnnnnnnnn guuuuagagc uagaaauagc aaguuaaaau     60

aaggcuaguc cguuaucaac uugaaaaagu ggcaccgagu cggugcuuuu uuuu          114


<210> SEQ ID NO 23
<211> LENGTH: 19
```

<212> TYPE: DNA
<213> ORGANISM: Artificial Sequence
<220> FEATURE:
<223> OTHER INFORMATION: Synthetic

<400> SEQUENCE: 23
aagagcaaca aatctgact 19

<210> SEQ ID NO 24
<211> LENGTH: 39
<212> TYPE: DNA
<213> ORGANISM: Artificial Sequence
<220> FEATURE:
<223> OTHER INFORMATION: Synthetic

<400> SEQUENCE: 24
aagagcaaca gtgctgtgcc tggagcaaca aatctgact 39

<210> SEQ ID NO 25
<211> LENGTH: 33
<212> TYPE: DNA
<213> ORGANISM: Artificial Sequence
<220> FEATURE:
<223> OTHER INFORMATION: Synthetic

<400> SEQUENCE: 25
aagagcaaca gtgctggagc aacaaatctg act 33

<210> SEQ ID NO 26
<211> LENGTH: 34
<212> TYPE: DNA
<213> ORGANISM: Artificial Sequence
<220> FEATURE:
<223> OTHER INFORMATION: Synthetic

<400> SEQUENCE: 26
aagagcaaca gtgcctggag caacaaatct gact 34

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
aagagcaaca gtgctgact 19

<210> SEQ ID NO 28
<211> LENGTH: 41
<212> TYPE: DNA
<213> ORGANISM: Artificial Sequence
<220> FEATURE:
<223> OTHER INFORMATION: Synthetic

<400> SEQUENCE: 28
aagagcaaca gtgctgtggg cctggagcaa caaatctgac t 41

<210> SEQ ID NO 29
<211> LENGTH: 38
<212> TYPE: DNA
<213> ORGANISM: Artificial Sequence
<220> FEATURE:
<223> OTHER INFORMATION: Synthetic

<400> SEQUENCE: 29
aagagcaaca gtgctggcct ggagcaacaa atctgact 38

<210> SEQ ID NO 30
<211> LENGTH: 41
<212> TYPE: DNA
<213> ORGANISM: Artificial Sequence
<220> FEATURE:
<223> OTHER INFORMATION: Synthetic

<400> SEQUENCE: 30
aagagcaaca gtgctgtgtg cctggagcaa caaatctgac t 41

<210> SEQ ID NO 31
<211> LENGTH: 79
<212> TYPE: DNA
<213> ORGANISM: Artificial Sequence
<220> FEATURE:
<223> OTHER INFORMATION: Synthetic

<400> SEQUENCE: 31
cgtggcctta gctgtgctcg cgctactctc tctttctgcc tggaggctat ccagcgtgag 60
tctctcctac cctcccgct 79

<210> SEQ ID NO 32
<211> LENGTH: 78
<212> TYPE: DNA
<213> ORGANISM: Artificial Sequence
<220> FEATURE:
<223> OTHER INFORMATION: Synthetic

<400> SEQUENCE: 32
cgtggcctta gctgtgctcg cgctactctc tctttcgcct ggaggctatc cagcgtgagt 60
ctctcctacc ctcccgct 78

<210> SEQ ID NO 33
<211> LENGTH: 75
<212> TYPE: DNA
<213> ORGANISM: Artificial Sequence
<220> FEATURE:
<223> OTHER INFORMATION: Synthetic

<400> SEQUENCE: 33
cgtggcctta gctgtgctcg cgctactctc tctttctgga ggctatccag cgtgagtctc 60
tcctaccctc ccgct 75

<210> SEQ ID NO 34
<211> LENGTH: 84
<212> TYPE: DNA
<213> ORGANISM: Artificial Sequence
<220> FEATURE:
<223> OTHER INFORMATION: Synthetic

<400> SEQUENCE: 34
cgtggcctta gctgtgctcg cgctactctc tctttctgga tagcctggag gctatccagc 60
gtgagtctct cctaccctcc cgct 84

<210> SEQ ID NO 35
<211> LENGTH: 55
<212> TYPE: DNA
<213> ORGANISM: Artificial Sequence
<220> FEATURE:
<223> OTHER INFORMATION: Synthetic

<400> SEQUENCE: 35
cgtggcctta gctgtgctcg cgctatccag cgtgagtctc tcctaccctc ccgct 55

<210> SEQ ID NO 36
<211> LENGTH: 82
<212> TYPE: DNA
<213> ORGANISM: Artificial Sequence
<220> FEATURE:
<223> OTHER INFORMATION: Synthetic

<400> SEQUENCE: 36
cgtggcctta gctgtgctcg cgctactctc tctttctgtg gcctggaggc tatccagcgt 60
gagtctctcc taccctcccg ct 82

<210> SEQ ID NO 37
<211> LENGTH: 58
<212> TYPE: DNA
<213> ORGANISM: Artificial Sequence
<220> FEATURE:
<223> OTHER INFORMATION: Synthetic

<400> SEQUENCE: 37
cacaccacga ggcagatcac caagcccgcg caatgggacc aaagcagccc gcaggacg 58

<210> SEQ ID NO 38
<211> LENGTH: 61
<212> TYPE: DNA
<213> ORGANISM: Artificial Sequence
<220> FEATURE:
<223> OTHER INFORMATION: Synthetic

<400> SEQUENCE: 38
cacaccacga ggcagatcac caagcccgcg aaccaatggg accaaagcag cccgcaggac 60
g 61

<210> SEQ ID NO 39
<211> LENGTH: 48
<212> TYPE: DNA
<213> ORGANISM: Artificial Sequence
<220> FEATURE:
<223> OTHER INFORMATION: Synthetic

<400> SEQUENCE: 39
cacaccacga ggcagatcac caatgggacc aaagcagccc gcaggacg 48

<210> SEQ ID NO 40
<211> LENGTH: 59
<212> TYPE: DNA
<213> ORGANISM: Artificial Sequence
<220> FEATURE:
<223> OTHER INFORMATION: Synthetic

<400> SEQUENCE: 40
cacaccacga ggcagatcac caagcccgcg ccaatgggac caaagcagcc cgcaggacg 59

<210> SEQ ID NO 41
<211> LENGTH: 59
<212> TYPE: DNA
<213> ORGANISM: Artificial Sequence
<220> FEATURE:
<223> OTHER INFORMATION: Synthetic

<400> SEQUENCE: 41
cacaccacga ggcagatcac caagcccgca ccaatgggac caaagcagcc cgcaggacg 59

<210> SEQ ID NO 42
<211> LENGTH: 35
<212> TYPE: DNA
<213> ORGANISM: Artificial Sequence
<220> FEATURE:
<223> OTHER INFORMATION: Synthetic

<400> SEQUENCE: 42
cacaccacga ggcagatcac caagcccgca ggacg 35

<210> SEQ ID NO 43
<211> LENGTH: 4688
<212> TYPE: DNA
<213> ORGANISM: Artificial Sequence
<220> FEATURE:
<223> OTHER INFORMATION: Synthetic

<400> SEQUENCE: 43
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgagatg taaggagctg ctgtgacttg ctcaaggcct 180
tatatcgagt aaacggtagt gctggggctt agacgcaggt gttctgattt atagttcaaa 240
acctctatca atgagagagc aatctcctgg taatgtgata gatttcccaa cttaatgcca 300
acataccata aacctcccat tctgctaatg cccagcctaa gttggggaga ccactccaga 360
ttccaagatg tacagtttgc tttgctgggc ctttttccca tgcctgcctt tactctgcca 420
gagttatatt gctggggttt tgaagaagat cctattaaat aaaagaataa gcagtattat 480
taagtagccc tgcatttcag gtttccttga gtggcaggcc aggcctggcc gtgaacgttc 540
actgaaatca tggcctcttg gccaagattg atagcttgtg cctgtccctg agtcccagtc 600
catcacgagc agctggtttc taagatgcta tttcccgtat aaagcatgag accgtgactt 660
gccagcccca cagagccccg cccttgtcca tcactggcat ctggactcca gcctgggttg 720
gggcaaagag ggaaatgaga tcatgtccta accctgatcc tcttgtccca cagatatcca 780
gaaccctgac cctgccgtgt accagctgag agactctaaa tccagtgaca agtctgtctg 840
cctattcacc gattttgatt ctcaaacaaa tgtgtcacaa agtaaggatt ctgatgtgta 900
tatcacagac aaaactgtgc tagacatgag gtctatggac ttcaggctcc ggtgcccgtc 960
agtgggcaga gcgcacatcg cccacagtcc ccgagaagtt ggggggaggg gtcggcaatt 1020
gaaccggtgc ctagagaagg tggcgcgggg taaactggga aagtgatgtc gtgtactggc 1080
tccgcctttt tcccgagggt gggggagaac cgtatataag tgcagtagtc gccgtgaacg 1140
ttctttttcg caacgggttt gccgccagaa cacaggtaag tgccgtgtgt ggttcccgcg 1200
ggcctggcct ctttacgggt tatggccctt gcgtgccttg aattacttcc actggctgca 1260
gtacgtgatt cttgatcccg agcttcgggt tggaagtggg tgggagagtt cgaggccttg 1320
cgcttaagga gccccttcgc ctcgtgcttg agttgaggcc tggcctgggc gctggggccg 1380
ccgcgtgcga atctggtggc accttcgcgc ctgtctcgct gctttcgata agtctctagc 1440
catttaaaat ttttgatgac ctgctgcgac gctttttttc tggcaagata gtcttgtaaa 1500
tgcgggccaa gatctgcaca ctggtatttc ggtttttggg gccgcgggcg gcgacggggc 1560
ccgtgcgtcc cagcgcacat gttcggcgag gcggggcctg cgagcgcggc caccgagaat 1620
cggacggggg tagtctcaag ctggccggcc tgctctggtg cctggcctcg cgccgccgtg 1680
tatcgccccg ccctgggcgg caaggctggc ccggtcggca ccagttgcgt gagcggaaag 1740

```
atggccgctt cccggccctg ctgcagggag ctcaaaatgg aggacgcggc gctcgggaga   1800
gcgggcgggt gagtcaccca cacaaaggaa aagggccttt ccgtcctcag ccgtcgcttc   1860
atgtgactcc acggagtacc gggcgccgtc caggcacctc gattagttct cgagcttttg   1920
gagtacgtcg tctttaggtt ggggggaggg gttttatgcg atggagtttc cccacactga   1980
gtgggtggag actgaagtta ggccagcttg gcacttgatg taattctcct tggaatttgc   2040
cctttttgag tttggatctt ggttcattct caagcctcag acagtggttc aaagtttttt   2100
tcttccattt caggtgtcgt gaccaccatg gcgcttccgg tgacagcact gctcctcccc   2160
ttggcgctgt tgctccacgc agcaaggccg caggtccagt tggtgcaaag cggggcggag   2220
gtgaaaaaac ccggcgcttc cgtgaaggtg tcctgtaagg cgtccggtta tacgttcacg   2280
aactacggga tgaattgggt tcgccaagcg ccggggcagg gactgaaatg gatggggtgg   2340
ataaatacct acaccggcga acctacatac gccgacgctt ttaaagggcg agtcactatg   2400
acgcgcgata ccagcatatc caccgcatac atggagctgt cccgactccg gtcagacgac   2460
acggctgtct actattgtgc tcgggactat ggcgattatg gcatggacta ctggggtcag   2520
ggtacgactg taacagttag tagtggtgga ggcggcagtg gcgggggggg aagcggagga   2580
gggggttctg gtgacatagt tatgacccaa tccccagata gtttggcggt ttctctgggc   2640
gagagggcaa cgattaattg tcgcgcatca aagagcgttt caacgagcgg atattctttt   2700
atgcattggt accagcaaaa acccggacaa ccgccgaagc tgctgatcta cttggcttca   2760
aatcttgagt ctggggtgcc ggaccgattt tctggtagtg gaagcggaac tgactttacg   2820
ctcacgatca gttcactgca ggctgaggat gtagcggtct attattgcca gcacagtaga   2880
gaagtcccct ggaccttcgg tcaaggcacg aaagtagaaa ttaaaagtgc tgctgccttt   2940
gtcccggtat ttctcccagc caaaccgacc acgactcccg ccccgcgccc tccgacaccc   3000
gctcccacca tcgcctctca acctcttagt cttcgccccg aggcatgccg acccgccgcc   3060
gggggtgctg ttcatacgag ggcttggac ttcgcttgtg atatttacat ttgggctccg   3120
ttggcgggta cgtgcggcgt ccttttgttg tcactcgtta ttactttgta ttgtaatcac   3180
aggaatcgca aacggggcag aaagaaactc ctgtatatat tcaaacaacc atttatgaga   3240
ccagtacaaa ctactcaaga ggaagatggc tgtagctgcc gatttccaga agaagaagaa   3300
ggaggatgtg aactgcgagt gaagttttcc cgaagcgcag acgctccggc atatcagcaa   3360
ggacagaatc agctgtataa cgaactgaat ttgggacgcc gcgaggagta tgacgtgctt   3420
gataaacgcc gggggagaga cccggaaatg gggggtaaac cccgaagaaa gaatccccaa   3480
gaaggactct acaatgaact ccagaaggat aagatggcgg aggcctactc agaaataggt   3540
atgaagggcg aacgacgacg gggaaaaggt cacgatggcc tctaccaagg gttgagtacg   3600
gcaaccaaag atacgtacga tgcactgcat atgcaggccc tgcctcccag ataataataa   3660
aatcgctatc catcgaagat ggatgtgtgt tggttttttg tgtgtggagc aacaaatctg   3720
actttgcatg tgcaaacgcc ttcaacaaca gcattattcc agaagacacc ttcttcccca   3780
gcccaggtaa gggcagcttt ggtgccttcg caggctgttt ccttgcttca ggaatggcca   3840
ggttctgccc agagctctgg tcaatgatgt ctaaaactcc tctgattggt ggtctcggcc   3900
ttatccattg ccaccaaaac cctcttttta ctaagaaaca gtgagccttg ttctggcagt   3960
ccagagaatg acacgggaaa aaagcagatg aagagaaggt ggcaggagag ggcacgtggc   4020
ccagcctcag tctctccaac tgagttcctg cctgcctgcc tttgctcaga ctgtttgccc   4080
```

```
cttactgctc ttctaggcct cattctaagc cccttctcca agttgcctct ccttatttct   4140

ccctgtctgc caaaaaatct ttcccagctc actaagtcag tctcacgcag tcactcatta   4200

acccaccaat cactgattgt gccggcacat gaatgcacca ggtgttgaag tggaggaatt   4260

aaaaagtcag atgaggggtg tgcccagagg aagcaccatt ctagttgggg gagcccatct   4320

gtcagctggg aaaagtccaa ataacttcag attggaatgt gttttaactc agggttgaga   4380

aaacagctac cttcaggaca aaagtcaggg aagggctctc tgaagaaatg ctacttgaag   4440

ataccagccc taccaagggc agggagagga ccctatagag gcctgggaca ggagctcaat   4500

gagaaaggta accacgtgcg gaccgaggct gcagcgtcgt cctccctagg aacccctagt   4560

gatggagttg gccactccct ctctgcgcgc tcgctcgctc actgaggccg ggcgaccaaa   4620

ggtcgcccga cgcccgggct ttgcccgggc ggcctcagtg agcgagcgag cgcgcagctg   4680

cctgcagg                                                            4688
```

<210> SEQ ID NO 44
<211> LENGTH: 4364
<212> TYPE: DNA
<213> ORGANISM: Artificial Sequence
<220> FEATURE:
<223> OTHER INFORMATION: Synthetic

<400> SEQUENCE: 44

```
gagatgtaag gagctgctgt gacttgctca aggccttata tcgagtaaac ggtagtgctg     60

gggcttagac gcaggtgttc tgatttatag ttcaaaacct ctatcaatga gagagcaatc    120

tcctggtaat gtgatagatt tcccaactta atgccaacat accataaacc tcccattctg    180

ctaatgccca gcctaagttg gggagaccac tccagattcc aagatgtaca gtttgctttg    240

ctgggccttt ttcccatgcc tgcctttact ctgccagagt tatattgctg gggttttgaa    300

gaagatccta ttaaataaaa gaataagcag tattattaag tagccctgca tttcaggttt    360

ccttgagtgg caggccaggc ctggccgtga acgttcactg aaatcatggc ctcttggcca    420

agattgatag cttgtgcctg tccctgagtc ccagtccatc acgagcagct ggtttctaag    480

atgctatttc ccgtataaag catgagaccg tgacttgcca gccccacaga gccccgccct    540

tgtccatcac tggcatctgg actccagcct gggttggggc aaagagggaa atgagatcat    600

gtcctaaccc tgatcctctt gtcccacaga tatccagaac cctgaccctg ccgtgtacca    660

gctgagagac tctaaatcca gtgacaagtc tgtctgccta ttcaccgatt ttgattctca    720

aacaaatgtg tcacaaagta aggattctga tgtgtatatc acagacaaaa ctgtgctaga    780

catgaggtct atggacttca ggctccggtg cccgtcagtg ggcagagcgc acatcgccca    840

cagtccccga gaagttgggg ggaggggtcg gcaattgaac cggtgcctag agaaggtggc    900

gcggggtaaa ctgggaaagt gatgtcgtgt actggctccg cctttttccc gagggtgggg    960

gagaaccgta tataagtgca gtagtcgccg tgaacgttct ttttcgcaac gggtttgccg   1020

ccagaacaca ggtaagtgcc gtgtgtggtt cccgcgggcc tggcctcttt acgggttatg   1080

gcccttgcgt gccttgaatt acttccactg gctgcagtac gtgattcttg atcccgagct   1140

tcgggttgga agtgggtggg agagttcgag gccttgcgct taaggagccc cttcgcctcg   1200

tgcttgagtt gaggcctggc ctgggcgctg gggccgccgc gtgcgaatct ggtggcacct   1260

tcgcgcctgt ctcgctgctt tcgataagtc tctagccatt taaaattttt gatgacctgc   1320

tgcgacgctt tttttctggc aagatagtct tgtaaatgcg ggccaagatc tgcacactgg   1380

tatttcggtt tttggggccg cgggcggcga cggggcccgt gcgtcccagc gcacatgttc   1440
```

```
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccgcagg tccagttggt gcaaagcggg gcggaggtga aaaaacccgg cgcttccgtg   2100
aaggtgtcct gtaaggcgtc cggttatacg ttcacgaact acgggatgaa ttgggttcgc   2160
caagcgccgg ggcagggact gaaatggatg ggtggataa atacctacac cggcgaacct    2220
acatacgccg acgcttttaa agggcgagtc actatgacgc gcgataccag catatccacc   2280
gcatacatgg agctgtcccg actccggtca gacgacacgg ctgtctacta ttgtgctcgg   2340
gactatggcg attatggcat ggactactgg ggtcagggta cgactgtaac agttagtagt   2400
ggtggaggcg gcagtggcgg ggggggaagc ggaggagggg gttctggtga catagttatg   2460
acccaatccc cagatagttt ggcggtttct ctgggcgaga gggcaacgat taattgtcgc   2520
gcatcaaaga gcgtttcaac gagcggatat tcttttatgc attggtacca gcaaaaaccc   2580
ggacaaccgc cgaagctgct gatctacttg gcttcaaatc ttgagtctgg ggtgccggac   2640
cgattttctg gtagtggaag cggaactgac tttacgctca cgatcagttc actgcaggct   2700
gaggatgtag cggtctatta ttgccagcac agtagagaag tcccctggac cttcggtcaa   2760
ggcacgaaag tagaaattaa aagtgctgct gcctttgtcc cggtatttct cccagccaaa   2820
ccgaccacga ctcccgcccc gcgccctccg acacccgctc ccaccatcgc ctctcaacct   2880
cttagtcttc gccccgaggc atgccgaccc gccgccgggg gtgctgttca tacgaggggc   2940
ttggacttcg cttgtgatat ttacatttgg gctccgttgg cgggtacgtg cggcgtcctt   3000
ttgttgtcac tcgttattac tttgtattgt aatcacagga atcgcaaacg gggcagaaag   3060
aaactcctgt atatattcaa acaaccattt atgagaccag tacaaactac tcaagaggaa   3120
gatggctgta gctgccgatt tccagaagaa gaagaaggag gatgtgaact gcgagtgaag   3180
ttttcccgaa gcgcagacgc tccggcatat cagcaaggac agaatcagct gtataacgaa   3240
ctgaatttgg gacgccgcga ggagtatgac gtgcttgata aacgccgggg gagagacccg   3300
gaaatggggg gtaaaccccg aagaaagaat ccccaagaag gactctacaa tgaactccag   3360
aaggataaga tggcggaggc ctactcagaa ataggtatga agggcgaacg acgacgggga   3420
aaaggtcacg atggcctcta ccaagggttg agtacggcaa ccaaagatac gtacgatgca   3480
ctgcatatgc aggccctgcc tcccagataa taataaaatc gctatccatc gaagatggat   3540
gtgtgttggt tttttgtgtg tggagcaaca aatctgactt tgcatgtgca aacgccttca   3600
acaacagcat tattccagaa gacaccttct tccccagccc aggtaagggc agctttggtg   3660
ccttcgcagg ctgtttcctt gcttcaggaa tggccaggtt ctgcccagag ctctggtcaa   3720
tgatgtctaa aactcctctg attggtggtc tcggccttat ccattgccac caaaaccctc   3780
```

```
tttttactaa gaaacagtga gccttgttct ggcagtccag agaatgacac gggaaaaaag   3840
cagatgaaga gaaggtggca ggagagggca cgtggcccag cctcagtctc tccaactgag   3900
ttcctgcctg cctgcctttg ctcagactgt ttgcccctta ctgctcttct aggcctcatt   3960
ctaagcccct tctccaagtt gcctctcctt atttctccct gtctgccaaa aaatctttcc   4020
cagctcacta agtcagtctc acgcagtcac tcattaaccc accaatcact gattgtgccg   4080
gcacatgaat gcaccaggtg ttgaagtgga ggaattaaaa agtcagatga ggggtgtgcc   4140
cagaggaagc accattctag ttgggggagc ccatctgtca gctgggaaaa gtccaaataa   4200
cttcagattg gaatgtgttt taactcaggg ttgagaaaac agctaccttc aggacaaaag   4260
tcagggaagg gctctctgaa gaaatgctac ttgaagatac cagccctacc aagggcaggg   4320
agaggaccct atagaggcct gggacaggag ctcaatgaga aagg                     4364
```

```
<210> SEQ ID NO 45
<211> LENGTH: 1527
<212> TYPE: DNA
<213> ORGANISM: Artificial Sequence
<220> FEATURE:
<223> OTHER INFORMATION: Synthetic

<400> SEQUENCE: 45

atggcgcttc cggtgacagc actgctcctc cccttggcgc tgttgctcca cgcagcaagg     60
ccgcaggtcc agttggtgca aagcggggcg gaggtgaaaa aacccggcgc ttccgtgaag    120
gtgtcctgta aggcgtccgg ttatacgttc acgaactacg ggatgaattg ggttcgccaa    180
gcgccggggc agggactgaa atggatgggg tggataaata cctacaccgg cgaacctaca    240
tacgccgacg cttttaaagg gcgagtcact atgacgcgcg ataccagcat atccaccgca    300
tacatggagc tgtcccgact ccggtcagac gacacggctg tctactattg tgctcgggac    360
tatggcgatt atggcatgga ctactggggt cagggtacga ctgtaacagt tagtagtggt    420
ggaggcggca gtggcggggg gggaagcgga ggaggggtt ctggtgacat agttatgacc    480
caatccccag atagtttggc ggtttctctg ggcgagaggg caacgattaa ttgtcgcgca    540
tcaaagagcg tttcaacgag cggatattct tttatgcatt ggtaccagca aaaacccgga    600
caaccgccga agctgctgat ctacttggct tcaaatcttg agtctggggt gccggaccga    660
ttttctggta gtggaagcgg aactgacttt acgctcacga tcagttcact gcaggctgag    720
gatgtagcgg tctattattg ccagcacagt agagaagtcc cctggacctt cggtcaaggc    780
acgaaagtag aaattaaaag tgctgctgcc tttgtcccgg tatttctccc agccaaaccg    840
accacgactc ccgccccgcg ccctccgaca cccgctccca ccatcgcctc tcaacctctt    900
agtcttcgcc ccgaggcatg ccgacccgcc gccgggggtg ctgttcatac gaggggcttg    960
gacttcgctt gtgatattta catttgggct ccgttggcgg gtacgtgcgg cgtccttttg   1020
ttgtcactcg ttattacttt gtattgtaat cacaggaatc gcaaacgggg cagaaagaaa   1080
ctcctgtata tattcaaaca accatttatg agaccagtac aaactactca agaggaagat   1140
ggctgtagct gccgatttcc agaagaagaa gaaggaggat gtgaactgcg agtgaagttt   1200
tcccgaagcg cagacgctcc ggcatatcag caaggacaga atcagctgta taacgaactg   1260
aatttgggac gccgcgagga gtatgacgtg cttgataaac gccgggggag agacccggaa   1320
atgggggggta aaccccgaag aaagaatccc caagaaggac tctacaatga actccagaag   1380
gataagatgg cggaggccta ctcagaaata ggtatgaagg gcgaacgacg acggggaaaa   1440
ggtcacgatg gcctctacca agggttgagt acggcaacca aagatacgta cgatgcactg   1500
```

catatgcagg ccctgcctcc cagataa 1527

<210> SEQ ID NO 46
<211> LENGTH: 508
<212> TYPE: PRT
<213> ORGANISM: Artificial Sequence
<220> FEATURE:
<223> OTHER INFORMATION: Synthetic

<400> SEQUENCE: 46

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Pro Gly Ala Ser Val Lys Val Ser Cys Lys Ala Ser Gly Tyr
35 40 45

Thr Phe Thr Asn Tyr Gly Met Asn Trp Val Arg Gln Ala Pro Gly Gln
50 55 60

Gly Leu Lys Trp Met Gly Trp Ile Asn Thr Tyr Thr Gly Glu Pro Thr
65 70 75 80

Tyr Ala Asp Ala Phe Lys Gly Arg Val Thr Met Thr Arg Asp Thr Ser
85 90 95

Ile Ser Thr Ala Tyr Met Glu Leu Ser Arg Leu Arg Ser Asp Asp Thr
100 105 110

Ala Val Tyr Tyr Cys Ala Arg Asp Tyr Gly Asp Tyr Gly Met Asp Tyr
115 120 125

Trp Gly Gln Gly Thr Thr Val Thr Val Ser Ser Gly Gly Gly Gly Ser
130 135 140

Gly Gly Gly Gly Ser Gly Gly Gly Gly Ser Gly Asp Ile Val Met Thr
145 150 155 160

Gln Ser Pro Asp Ser Leu Ala Val Ser Leu Gly Glu Arg Ala Thr Ile
165 170 175

Asn Cys Arg Ala Ser Lys Ser Val Ser Thr Ser Gly Tyr Ser Phe Met
180 185 190

His Trp Tyr Gln Gln Lys Pro Gly Gln Pro Pro Lys Leu Leu Ile Tyr
195 200 205

Leu Ala Ser Asn Leu Glu Ser Gly Val Pro Asp Arg Phe Ser Gly Ser
210 215 220

Gly Ser Gly Thr Asp Phe Thr Leu Thr Ile Ser Ser Leu Gln Ala Glu
225 230 235 240

Asp Val Ala Val Tyr Tyr Cys Gln His Ser Arg Glu Val Pro Trp Thr
245 250 255

Phe Gly Gln Gly Thr Lys Val Glu Ile Lys Ser Ala Ala Ala Phe Val
260 265 270

Pro Val Phe Leu Pro Ala Lys Pro Thr Thr Thr Pro Ala Pro Arg Pro
275 280 285

Pro Thr Pro Ala Pro Thr Ile Ala Ser Gln Pro Leu Ser Leu Arg Pro
290 295 300

Glu Ala Cys Arg Pro Ala Ala Gly Gly Ala Val His Thr Arg Gly Leu
305 310 315 320

Asp Phe Ala Cys Asp Ile Tyr Ile Trp Ala Pro Leu Ala Gly Thr Cys
325 330 335

Gly Val Leu Leu Leu Ser Leu Val Ile Thr Leu Tyr Cys Asn His Arg
340 345 350

```
Asn Arg Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505


<210> SEQ ID NO 47
<211> LENGTH: 735
<212> TYPE: PRT
<213> ORGANISM: Artificial Sequence
<220> FEATURE:
<223> OTHER INFORMATION: Synthetic

<400> SEQUENCE: 47

Cys Ala Gly Gly Thr Cys Cys Ala Gly Thr Thr Gly Gly Thr Gly Cys
1               5                   10                  15

Ala Ala Ala Gly Cys Gly Gly Gly Gly Cys Gly Gly Ala Gly Gly Thr
            20                  25                  30

Gly Ala Ala Ala Ala Ala Ala Cys Cys Cys Gly Gly Cys Gly Cys Thr
        35                  40                  45

Thr Cys Cys Gly Thr Gly Ala Ala Gly Gly Thr Gly Thr Cys Cys Thr
    50                  55                  60

Gly Thr Ala Ala Gly Gly Cys Gly Thr Cys Cys Gly Gly Thr Thr Ala
65                  70                  75                  80

Thr Ala Cys Gly Thr Thr Cys Ala Cys Gly Ala Ala Cys Thr Ala Cys
                85                  90                  95

Gly Gly Gly Ala Thr Gly Ala Ala Thr Thr Gly Gly Gly Thr Thr Cys
            100                 105                 110

Gly Cys Cys Ala Ala Gly Cys Gly Cys Cys Gly Gly Gly Gly Cys Ala
        115                 120                 125

Gly Gly Gly Ala Cys Thr Gly Ala Ala Ala Thr Gly Gly Ala Thr Gly
    130                 135                 140

Gly Gly Gly Thr Gly Gly Ala Thr Ala Ala Ala Thr Ala Cys Cys Thr
145                 150                 155                 160

Ala Cys Ala Cys Cys Gly Gly Cys Gly Ala Ala Cys Cys Thr Ala Cys
                165                 170                 175

Ala Thr Ala Cys Gly Cys Cys Gly Ala Cys Gly Cys Thr Thr Thr Thr
            180                 185                 190

Ala Ala Ala Gly Gly Gly Cys Gly Ala Gly Thr Cys Ala Cys Thr Ala
        195                 200                 205
```

-continued

```
Thr Gly Ala Cys Gly Cys Gly Cys Gly Ala Thr Ala Cys Cys Ala Gly
    210                 215                 220

Cys Ala Thr Ala Thr Cys Cys Ala Cys Cys Gly Cys Ala Thr Ala Cys
225                 230                 235                 240

Ala Thr Gly Gly Ala Gly Cys Thr Gly Thr Cys Cys Cys Gly Ala Cys
                245                 250                 255

Thr Cys Cys Gly Gly Thr Cys Ala Gly Ala Cys Gly Ala Cys Ala Cys
            260                 265                 270

Gly Gly Cys Thr Gly Thr Cys Thr Ala Cys Thr Ala Thr Thr Gly Thr
        275                 280                 285

Gly Cys Thr Cys Gly Gly Gly Ala Cys Thr Ala Thr Gly Gly Cys Gly
    290                 295                 300

Ala Thr Thr Ala Thr Gly Gly Cys Ala Thr Gly Gly Ala Cys Thr Ala
305                 310                 315                 320

Cys Thr Gly Gly Gly Gly Thr Cys Ala Gly Gly Gly Thr Ala Cys Gly
                325                 330                 335

Ala Cys Thr Gly Thr Ala Ala Cys Ala Gly Thr Thr Ala Gly Thr Ala
            340                 345                 350

Gly Thr Gly Gly Thr Gly Gly Ala Gly Gly Cys Gly Gly Cys Ala Gly
        355                 360                 365

Thr Gly Gly Cys Gly Gly Gly Gly Gly Gly Gly Gly Ala Ala Gly Cys
    370                 375                 380

Gly Gly Ala Gly Gly Ala Gly Gly Gly Gly Gly Thr Thr Cys Thr Gly
385                 390                 395                 400

Gly Thr Gly Ala Cys Ala Thr Ala Gly Thr Thr Ala Thr Gly Ala Cys
                405                 410                 415

Cys Cys Ala Ala Thr Cys Cys Cys Cys Ala Gly Ala Thr Ala Gly Thr
            420                 425                 430

Thr Thr Gly Gly Cys Gly Gly Thr Thr Thr Cys Thr Cys Thr Gly Gly
        435                 440                 445

Gly Cys Gly Ala Gly Ala Gly Gly Gly Cys Ala Ala Cys Gly Ala Thr
    450                 455                 460

Thr Ala Ala Thr Thr Gly Thr Cys Gly Cys Gly Cys Ala Thr Cys Ala
465                 470                 475                 480

Ala Ala Gly Ala Gly Cys Gly Thr Thr Thr Cys Ala Ala Cys Gly Ala
                485                 490                 495

Gly Cys Gly Gly Ala Thr Ala Thr Thr Cys Thr Thr Thr Thr Ala Thr
            500                 505                 510

Gly Cys Ala Thr Thr Gly Gly Thr Ala Cys Cys Ala Gly Cys Ala Ala
        515                 520                 525

Ala Ala Ala Cys Cys Cys Gly Gly Ala Cys Ala Ala Cys Cys Gly Cys
    530                 535                 540

Cys Gly Ala Ala Gly Cys Thr Gly Cys Thr Gly Ala Thr Cys Thr Ala
545                 550                 555                 560

Cys Thr Thr Gly Gly Cys Thr Thr Cys Ala Ala Ala Thr Cys Thr Thr
                565                 570                 575

Gly Ala Gly Thr Cys Thr Gly Gly Gly Gly Thr Gly Cys Cys Gly Gly
            580                 585                 590

Ala Cys Cys Gly Ala Thr Thr Thr Thr Cys Thr Gly Gly Thr Ala Gly
        595                 600                 605

Thr Gly Gly Ala Ala Gly Cys Gly Gly Ala Ala Cys Thr Gly Ala Cys
    610                 615                 620

Thr Thr Thr Ala Cys Gly Cys Thr Cys Ala Cys Gly Ala Thr Cys Ala
```

```
625                 630                 635                 640

Gly Thr Thr Cys Ala Cys Thr Gly Cys Ala Gly Gly Cys Thr Gly Ala
                645                 650                 655

Gly Gly Ala Thr Gly Thr Ala Gly Cys Gly Gly Thr Cys Thr Ala Thr
            660                 665                 670

Thr Ala Thr Thr Gly Cys Cys Ala Gly Cys Ala Cys Ala Gly Thr Ala
        675                 680                 685

Gly Ala Gly Ala Ala Gly Thr Cys Cys Cys Cys Thr Gly Gly Ala Cys
    690                 695                 700

Cys Thr Thr Cys Gly Gly Thr Cys Ala Ala Gly Gly Cys Ala Cys Gly
705                 710                 715                 720

Ala Ala Ala Gly Thr Ala Gly Ala Ala Ala Thr Thr Ala Ala Ala
                725                 730                 735


<210> SEQ ID NO 48
<211> LENGTH: 245
<212> TYPE: PRT
<213> ORGANISM: Artificial Sequence
<220> FEATURE:
<223> OTHER INFORMATION: Synthetic

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Asp Ile Val Met Thr Gln Ser Pro Asp Ser
    130                 135                 140

Leu Ala Val Ser Leu Gly Glu Arg Ala Thr Ile Asn Cys Arg Ala Ser
145                 150                 155                 160

Lys Ser Val Ser Thr Ser Gly Tyr Ser Phe Met His Trp Tyr Gln Gln
                165                 170                 175

Lys Pro Gly Gln Pro Pro Lys Leu Leu Ile Tyr Leu Ala Ser Asn Leu
            180                 185                 190

Glu Ser Gly Val Pro Asp Arg Phe Ser Gly Ser Gly Ser Gly Thr Asp
        195                 200                 205

Phe Thr Leu Thr Ile Ser Ser Leu Gln Ala Glu Asp Val Ala Val Tyr
    210                 215                 220

Tyr Cys Gln His Ser Arg Glu Val Pro Trp Thr Phe Gly Gln Gly Thr
225                 230                 235                 240

Lys Val Glu Ile Lys
                245
```

```
<210> SEQ ID NO 49
<211> LENGTH: 118
<212> TYPE: PRT
<213> ORGANISM: Artificial Sequence
<220> FEATURE:
<223> OTHER INFORMATION: Synthetic

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115


<210> SEQ ID NO 50
<211> LENGTH: 111
<212> TYPE: PRT
<213> ORGANISM: Artificial Sequence
<220> FEATURE:
<223> OTHER INFORMATION: Synthetic

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys
            100                 105                 110


<210> SEQ ID NO 51
<211> LENGTH: 16
<212> TYPE: PRT
<213> ORGANISM: Artificial Sequence
<220> FEATURE:
<223> OTHER INFORMATION: Synthetic

<400> SEQUENCE: 51

Gly Gly Gly Gly Ser Gly Gly Gly Gly Ser Gly Gly Gly Gly Ser Gly
1               5                   10                  15


<210> SEQ ID NO 52
```

<211> LENGTH: 22
<212> TYPE: PRT
<213> ORGANISM: Artificial Sequence
<220> FEATURE:
<223> OTHER INFORMATION: Synthetic

<400> SEQUENCE: 52

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 53
<211> LENGTH: 21
<212> TYPE: PRT
<213> ORGANISM: Artificial Sequence
<220> FEATURE:
<223> OTHER INFORMATION: Synthetic

<400> SEQUENCE: 53

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 54
<211> LENGTH: 84
<212> TYPE: PRT
<213> ORGANISM: Artificial Sequence
<220> FEATURE:
<223> OTHER INFORMATION: Synthetic

<400> SEQUENCE: 54

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg
```

<210> SEQ ID NO 55
<211> LENGTH: 23
<212> TYPE: PRT
<213> ORGANISM: Artificial Sequence
<220> FEATURE:
<223> OTHER INFORMATION: Synthetic

<400> SEQUENCE: 55

```
Ile Tyr Ile Trp Ala Pro Leu Ala Gly Thr Cys Gly Val Leu Leu Leu
1               5                   10                  15

Ser Leu Val Ile Thr Leu Tyr
            20
```

<210> SEQ ID NO 56
<211> LENGTH: 126
<212> TYPE: DNA
<213> ORGANISM: Artificial Sequence
<220> FEATURE:

<223> OTHER INFORMATION: Synthetic

<400> SEQUENCE: 56

```
aaacggggca gaaagaaact cctgtatata ttcaaacaac catttatgag accagtacaa     60

actactcaag aggaagatgg ctgtagctgc cgatttccag aagaagaaga aggaggatgt    120

gaactg                                                               126
```

<210> SEQ ID NO 57
<211> LENGTH: 42
<212> TYPE: PRT
<213> ORGANISM: Artificial Sequence
<220> FEATURE:
<223> OTHER INFORMATION: Synthetic

<400> SEQUENCE: 57

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 58
<211> LENGTH: 120
<212> TYPE: DNA
<213> ORGANISM: Artificial Sequence
<220> FEATURE:
<223> OTHER INFORMATION: Synthetic

<400> SEQUENCE: 58

```
tcaaagcgga gtaggttgtt gcattccgat tacatgaata tgactcctcg ccggcctggg     60

ccgacaagaa aacattacca accctatgcc cccccacgag acttcgctgc gtacaggtcc    120
```

<210> SEQ ID NO 59
<211> LENGTH: 40
<212> TYPE: PRT
<213> ORGANISM: Artificial Sequence
<220> FEATURE:
<223> OTHER INFORMATION: Synthetic

<400> SEQUENCE: 59

```
Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40
```

<210> SEQ ID NO 60
<211> LENGTH: 336
<212> TYPE: DNA
<213> ORGANISM: Artificial Sequence
<220> FEATURE:
<223> OTHER INFORMATION: Synthetic

<400> SEQUENCE: 60

```
cgagtgaagt tttcccgaag cgcagacgct ccggcatatc agcaaggaca gaatcagctg     60

tataacgaac tgaatttggg acgccgcgag gagtatgacg tgcttgataa acgccggggg    120

agagacccgg aaatgggggg taaaccccga agaaagaatc cccaagaagg actctacaat    180

gaactccaga aggataagat ggcggaggcc tactcagaaa taggtatgaa gggcgaacga    240
```

```
cgacggggaa aaggtcacga tggcctctac caagggttga gtacggcaac caaagatacg    300

tacgatgcac tgcatatgca ggccctgcct cccaga                              336


<210> SEQ ID NO 61
<211> LENGTH: 112
<212> TYPE: PRT
<213> ORGANISM: Artificial Sequence
<220> FEATURE:
<223> OTHER INFORMATION: Synthetic

<400> SEQUENCE: 61

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 62
<211> LENGTH: 800
<212> TYPE: DNA
<213> ORGANISM: Artificial Sequence
<220> FEATURE:
<223> OTHER INFORMATION: Synthetic

<400> SEQUENCE: 62

gagatgtaag gagctgctgt gacttgctca aggccttata tcgagtaaac ggtagtgctg     60

gggcttagac gcaggtgttc tgatttatag ttcaaaacct ctatcaatga gagagcaatc    120

tcctggtaat gtgatagatt tcccaactta atgccaacat accataaacc tcccattctg    180

ctaatgccca gcctaagttg gggagaccac tccagattcc aagatgtaca gtttgctttg    240

ctgggccttt ttcccatgcc tgcctttact ctgccagagt tatattgctg gggttttgaa    300

gaagatccta ttaaataaaa gaataagcag tattattaag tagccctgca tttcaggttt    360

ccttgagtgg caggccaggc ctggccgtga acgttcactg aaatcatggc ctcttggcca    420

agattgatag cttgtgcctg tccctgagtc ccagtccatc acgagcagct ggtttctaag    480

atgctatttc ccgtataaag catgagaccg tgacttgcca gccccacaga gccccgccct    540

tgtccatcac tggcatctgg actccagcct gggttggggc aaagagggaa atgagatcat    600

gtcctaaccc tgatcctctt gtcccacaga tatccagaac cctgaccctg ccgtgtacca    660

gctgagagac tctaaatcca gtgacaagtc tgtctgccta ttcaccgatt ttgattctca    720

aacaaatgtg tcacaaagta aggattctga tgtgtatatc acagacaaaa ctgtgctaga    780

catgaggtct atggacttca                                                800


<210> SEQ ID NO 63
<211> LENGTH: 1178
<212> TYPE: DNA
<213> ORGANISM: Artificial Sequence
```

<220> FEATURE:
<223> OTHER INFORMATION: Synthetic

<400> SEQUENCE: 63

```
ggctccggtg cccgtcagtg ggcagagcgc acatcgccca cagtccccga gaagttgggg     60
ggaggggtcg gcaattgaac cggtgcctag agaaggtggc gcggggtaaa ctgggaaagt    120
gatgtcgtgt actggctccg cctttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccactg gctgcagtac gtgattcttg atcccgagct tcgggttgga agtgggtggg    360
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaattttt gatgacctgc tgcgacgctt tttttctggc    540
aagatagtct tgtaaatgcg ggccaagatc tgcacactgg tatttcggtt tttggggccg    600
cgggcggcga cggggcccgt gcgtcccagc gcacatgttc ggcgaggcgg ggcctgcgag    660
cgcggccacc gagaatcgga cgggggtagt ctcaagctgg ccggcctgct ctggtgcctg    720
gcctcgcgcc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg gcctttccgt    900
cctcagccgt cgcttcatgt gactccacgg agtaccgggc gccgtccagg cacctcgatt    960
agttctcgag cttttggagt acgtcgtctt taggttgggg ggaggggttt tatgcgatgg   1020
agtttcccca cactgagtgg gtggagactg aagttaggcc agcttggcac ttgatgtaat   1080
tctccttgga atttgccctt tttgagtttg gatcttggtt cattctcaag cctcagacag   1140
tggttcaaag tttttttctt ccatttcagg tgtcgtga                           1178
```

<210> SEQ ID NO 64
<211> LENGTH: 49
<212> TYPE: DNA
<213> ORGANISM: Artificial Sequence
<220> FEATURE:
<223> OTHER INFORMATION: Synthetic

<400> SEQUENCE: 64

```
aataaaatcg ctatccatcg aagatggatg tgtgttggtt ttttgtgtg                 49
```

<210> SEQ ID NO 65
<211> LENGTH: 804
<212> TYPE: DNA
<213> ORGANISM: Artificial Sequence
<220> FEATURE:
<223> OTHER INFORMATION: Synthetic

<400> SEQUENCE: 65

```
tggagcaaca aatctgactt tgcatgtgca aacgccttca acaacagcat tattccagaa     60
gacaccttct tccccagccc aggtaagggc agctttggtg ccttcgcagg ctgtttcctt    120
gcttcaggaa tggccaggtt ctgcccagag ctctggtcaa tgatgtctaa aactcctctg    180
attggtggtc tcggccttat ccattgccac caaaaccctc tttttactaa gaaacagtga    240
gccttgttct ggcagtccag agaatgacac gggaaaaaag cagatgaaga gaaggtggca    300
ggagagggca cgtggcccag cctcagtctc tccaactgag ttcctgcctg cctgcctttg    360
```

-continued

```
ctcagactgt ttgcccctta ctgctcttct aggcctcatt ctaagcccct tctccaagtt    420

gcctctcctt atttctccct gtctgccaaa aaatctttcc cagctcacta agtcagtctc    480

acgcagtcac tcattaaccc accaatcact gattgtgccg gcacatgaat gcaccaggtg    540

ttgaagtgga ggaattaaaa agtcagatga ggggtgtgcc cagaggaagc accattctag    600

ttgggggagc ccatctgtca gctgggaaaa gtccaaataa cttcagattg gaatgtgttt    660

taactcaggg ttgagaaaac agctaccttc aggacaaaag tcagggaagg gctctctgaa    720

gaaatgctac ttgaagatac cagccctacc aagggcaggg agaggaccct atagaggcct    780

gggacaggag ctcaatgaga aagg                                           804


<210> SEQ ID NO 66
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 66

cugcagcuuc uccaacacau guuuuagagc uagaaauagc aaguuaaaau aaggcuaguc     60

cguuaucaac uugaaaaagu ggcaccgagu cggugcuuuu                          100
```